(12) United States Patent
Ouzounov et al.

(10) Patent No.: US 11,174,300 B2
(45) Date of Patent: Nov. 16, 2021

(54) ANIMAL-FREE DIETARY COLLAGEN

(71) Applicant: Geltor, Inc., San Leandro, CA (US)

(72) Inventors: Nikolay Ouzounov, San Ramon, CA (US); Jeffrey R. Mellin, Richmond, CA (US); Julia Co, Oakland, CA (US)

(73) Assignee: GELTOR, INC., San Leandro, CA (US)

( * ) Notice: Subject to any disclaimer, the term of this patent is extended or adjusted under 35 U.S.C. 154(b) by 0 days.

(21) Appl. No.: 17/171,874

(22) Filed: Feb. 9, 2021

(65) Prior Publication Data

US 2021/0277075 A1 Sep. 9, 2021

Related U.S. Application Data

(63) Continuation of application No. PCT/US2021/014714, filed on Jan. 22, 2021.

(60) Provisional application No. 62/965,700, filed on Jan. 24, 2020, provisional application No. 63/117,243, filed on Nov. 23, 2020.

(51) Int. Cl.
  C07K 14/78 (2006.01)
  C07K 14/47 (2006.01)
  A23L 33/18 (2016.01)

(52) U.S. Cl.
  CPC .............. *C07K 14/47* (2013.01); *A23L 33/18* (2016.08)

(58) Field of Classification Search
  CPC ... C07K 14/78; A61L 31/044; A61L 26/0033; A61K 38/39
  See application file for complete search history.

(56) References Cited

U.S. PATENT DOCUMENTS

| | | |
|---|---|---|
| 6,413,742 B1 | 7/2002 | Olsen et al. |
| 6,428,978 B1 | 8/2002 | Olsen et al. |
| 6,617,431 B1 | 9/2003 | Gruber et al. |
| 6,653,450 B1 | 11/2003 | Berg et al. |
| 6,682,760 B2 | 1/2004 | Noff et al. |
| 6,903,200 B1 | 6/2005 | Chou et al. |
| 6,992,172 B1 | 1/2006 | Chang et al. |
| 7,495,076 B2 | 2/2009 | Gu et al. |
| 7,700,126 B2 | 4/2010 | Ng et al. |
| 7,759,090 B2 | 7/2010 | Chou et al. |
| 7,803,577 B2 | 9/2010 | Weiss |
| 7,932,053 B2 | 4/2011 | Bank et al. |
| 7,932,353 B2 | 4/2011 | Van Es et al. |
| 8,252,553 B2 | 8/2012 | Hook et al. |
| 8,507,652 B2 | 8/2013 | Da Cruz |
| 8,618,250 B2 | 12/2013 | Russell et al. |
| 8,759,487 B2 | 6/2014 | Shoseyov et al. |
| 8,889,626 B2 | 11/2014 | Lin et al. |
| 8,956,632 B2 | 2/2015 | Boutros |
| 9,040,484 B2 | 5/2015 | Marinkovich et al. |
| 9,072,724 B2 | 7/2015 | Hausmanns et al. |
| 9,156,950 B2 | 10/2015 | Garralda et al. |
| 9,206,464 B2* | 12/2015 | Veidal ................ G01N 33/6893 |
| 9,328,154 B2 | 5/2016 | Chilkoti |
| 9,382,310 B2 | 7/2016 | Mirochnitchenko et al. |
| 9,591,853 B2 | 3/2017 | Belgorodsky et al. |
| 9,675,635 B2 | 6/2017 | Minatelli et al. |
| 9,676,837 B2 | 6/2017 | Viswanathan et al. |
| 10,053,501 B2 | 8/2018 | Ramshaw et al. |
| 10,155,793 B2 | 12/2018 | Ramshaw et al. |
| 10,232,008 B1 | 3/2019 | Moran |
| 10,358,464 B2 | 7/2019 | Hook et al. |
| 2013/0078209 A1 | 3/2013 | Yu et al. |
| 2015/0175969 A1 | 6/2015 | Yoshino et al. |
| 2019/0276515 A1 | 9/2019 | Bruno-Bonnet et al. |
| 2020/0009184 A1 | 1/2020 | Akthakul et al. |
| 2020/0306342 A1 | 10/2020 | Hamill et al. |
| 2020/0376091 A1 | 12/2020 | Seidensticker et al. |

FOREIGN PATENT DOCUMENTS

| | | |
|---|---|---|
| EP | 2941277 B1 | 9/2018 |
| WO | WO-9738710 A1 | 10/1997 |
| WO | WO-2004052910 A1 | 6/2004 |
| WO | WO-2017083398 A1 | 5/2017 |
| WO | WO-2017156418 A1 | 9/2017 |
| WO | WO-2017160636 A1 | 9/2017 |
| WO | WO-2017125585 A9 | 10/2017 |
| WO | WO-2017206326 A1 | 12/2017 |
| WO | WO-2018014453 A1 | 1/2018 |
| WO | WO-2018041684 A1 | 3/2018 |
| WO | WO-2018078276 A1 | 5/2018 |
| WO | WO-2018119530 A1 | 7/2018 |

(Continued)

OTHER PUBLICATIONS

Chandrakasan et al. Preparation of intact monomeric collagen from rat tail tendon and skin and the structure of the nonhelical ends in solution. J Biol Chem. Oct. 10, 1976;251(19):6062-7.

Fleischmajer et al. Rotary shadowing of collagen monomers, oligomers, and fibrils during tendon fibrillogenesis. J Histochem Cytochem. Jan. 1991;39(1):51-8.

Krapf et al. Deciphering the aggregation mechanism of bacteria (*Shewanella oneidensis* MR1) in the presence of polyethyleneimine: Effects of the exopolymeric superstructure and polymer molecular weight. Colloids Surf B Biointerfaces. Mar. 1, 2016;139:285-93. doi: 10.1016/j.colsurfb.2015.12.015. Epub Dec. 8, 2015.

Liu et al., Collagen and Gelatin. Annu. Rev. Food Sci. Technol. 6: 527-557 (2015).

(Continued)

*Primary Examiner* — Karen Cochrane Carlson
(74) *Attorney, Agent, or Firm* — Wilson Sonsini Goodrich & Rosati

(57) ABSTRACT

Provided herein are non-naturally occurring polypeptides comprising a sequence of a fragment of a collagen and recombinant cells containing heterologous nucleic acid sequences encoding the non-naturally occurring polypeptides. Further provided herein are animal-free methods of generating and purifying such non-naturally occurring polypeptides using microorganisms, preferably from bacterial cells.

30 Claims, 18 Drawing Sheets

Specification includes a Sequence Listing.

(56) References Cited

FOREIGN PATENT DOCUMENTS

| WO | WO-2019023555 A1 | 1/2019 |
| WO | WO-2019046943 A1 | 3/2019 |
| WO | WO-2019068018 A2 | 4/2019 |
| WO | WO-2019077312 A1 | 4/2019 |
| WO | WO-2019103981 A1 | 5/2019 |
| WO | WO-2019166418 A1 | 9/2019 |
| WO | WO-2021150959 A1 | 7/2021 |

OTHER PUBLICATIONS

Tomaro-Duchesneau et al. Microencapsulation for the Therapeutic Delivery of Drugs, Live Mammalian and Bacterial Cells, and Other Biopharmaceutics: Current Status and Future Directions. J Pharm (Cairo) 2013:103527 (2013). Published online Dec. 4, 2012. doi: 10.1155/2013/103527.

PCT/US2021/014714 International Search Report and Written Opinion dated Apr. 20, 2021.

* cited by examiner

ANIMAL-FREE DIETARY COLLAGEN

CROSS-REFERENCE

This application is a continuation application of International Patent Application No. PCT/US2021/014714, filed Jan. 22, 2021, which application claims the benefit of U.S. Provisional Application Nos. 62/965,700, filed Jan. 24, 2020, and 63/117,243, filed Nov. 23, 2020, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 21, 2021, is named 57607-708_601 SL.txt and is 46,248 bytes in size.

BACKGROUND

Collagen is one of the most abundant proteins found in various connective tissues in the body including tendons, ligaments, skin, and hair. Collagens or collagen supplements are popular in medical, cosmetic, and/or health purposes (e.g., stimulating skin growth, promoting wound healing, strengthening nails or joints, etc.). Collagens for most collagen supplements are derived from animals as a byproduct of the animal processing industry. Yet, such animal-derived collagens may increase the risk of illness transmission as well as allergies. Moreover, certain consumers are generally interested in animal-free products for a variety of other reasons. Thus, there remains a need for improved compositions and methods of collagens derived from non-animal sources.

SUMMARY

In one aspect, a non-naturally occurring polypeptide is provided comprising an amino acid sequence having: (i) at least 80% sequence identity to SEQ ID NO: 31 with an N-terminal truncation, a C-terminal truncation, or both; or (ii) at least 80% sequence identity to SEQ ID NO: 32 with an N-terminal truncation, a C-terminal truncation, or both. In some cases, the non-naturally occurring polypeptide comprises an amino acid sequence having: (i) at least 85% sequence identity to SEQ ID NO: 31 with an N-terminal truncation, a C-terminal truncation, or both; or (ii) at least 85% sequence identity to SEQ ID NO: 32 with an N-terminal truncation, a C-terminal truncation, or both. In some cases, the non-naturally occurring polypeptide comprises an amino acid sequence having: (i) at least 90% sequence identity to SEQ ID NO: 31 with an N-terminal truncation, a C-terminal truncation, or both; or (ii) at least 90% sequence identity to SEQ ID NO: 32 with an N-terminal truncation, a C-terminal truncation, or both. In some cases, the non-naturally occurring polypeptide comprises an amino acid sequence having: (i) at least 95% sequence identity to SEQ ID NO: 31 with an N-terminal truncation, a C-terminal truncation, or both; or (ii) at least 95% sequence identity to SEQ ID NO: 32 with an N-terminal truncation, a C-terminal truncation, or both. In some cases, the non-naturally occurring polypeptide comprises an amino acid sequence having: (i) at least 98% sequence identity to SEQ ID NO: 31 with an N-terminal truncation, a C-terminal truncation, or both; or (ii) at least 98% sequence identity to SEQ ID NO: 32 with an N-terminal truncation, a C-terminal truncation, or both. In some cases, the non-naturally occurring polypeptide comprises: (i) the amino acid sequence of SEQ ID NO: 31 with an N-terminal truncation, a C-terminal truncation, or both; or (ii) the amino acid sequence of SEQ ID NO: 32 with an N-terminal truncation, a C-terminal truncation, or both. In some cases, the non-naturally occurring polypeptide comprises an amino acid sequence having at least 80% sequence identity to SEQ ID NO: 31 with an N-terminal truncation. In some cases, the N-terminal truncation is an N-terminal truncation of 50 amino acids to 600 amino acids. In some cases, the non-naturally occurring polypeptide comprises an amino acid sequence having at least 80% sequence identity to SEQ ID NO: 31 with a C-terminal truncation. In some cases, the C-terminal truncation is a C-terminal truncation of 50 amino acids to 250 amino acids. In some cases, the non-naturally occurring polypeptide comprises an amino acid sequence having at least 80% sequence identity to SEQ ID NO: 31 with both an N-terminal truncation and a C-terminal truncation. In some cases, the N-terminal truncation is an N-terminal truncation of 50 amino acids to 600 amino acids, and the C-terminal truncation is a C-terminal truncation of 50 amino acids to 250 amino acids. In some cases, the non-naturally occurring polypeptide comprises the amino acid sequence of SEQ ID NO: 2 or SEQ ID NO: 6. In some cases, the non-naturally occurring polypeptide consists of the amino acid sequence of SEQ ID NO: 2 or SEQ ID NO: 6. In some cases, the non-naturally occurring polypeptide comprises an amino acid sequence having at least 80% sequence identity to SEQ ID NO: 32 with an N-terminal truncation. In some cases, the N-terminal truncation is an N-terminal truncation of 50 amino acids to 750 amino acids. In some cases, the non-naturally occurring polypeptide comprises an amino acid sequence having at least 80% sequence identity to SEQ ID NO: 32 with a C-terminal truncation. In some cases, the C-terminal truncation is a C-terminal truncation of 50 amino acids to 250 amino acids. In some cases, the non-naturally occurring polypeptide comprises an amino acid sequence having at least 80% sequence identity to SEQ ID NO: 32 with both an N-terminal truncation and a C-terminal truncation. In some cases, the N-terminal truncation is an N-terminal truncation of 50 amino acids to 750 amino acids, and the C-terminal truncation is a C-terminal truncation of 50 amino acids to 250 amino acids. In some cases, the non-naturally occurring polypeptide comprises the amino acid sequence of SEQ ID NO: 8. In some cases, the non-naturally occurring polypeptide consists of the amino acid sequence of SEQ ID NO: 8. In some cases, the non-naturally occurring polypeptide has a total truncation of 50 amino acids to 900 amino acids. In some cases, the non-naturally occurring polypeptide is 50 amino acids to 250 amino acids in length. In some cases, the non-naturally occurring polypeptide does not comprise one or more of: a laminin G domain, a Von Willebrand factor type A (vWA) domain, and a fibrillar collagen C-terminal domain. In some cases, the non-naturally occurring polypeptide comprises one or more collagen triple helix repeats. In some cases, the non-naturally occurring polypeptide is monomeric. In some cases, the non-naturally occurring polypeptide does not form a stable triple helix structure of a naturally occurring collagen. In some cases, the non-naturally occurring polypeptide is substantially free of other collagen chains. In some cases, the non-naturally occurring polypeptide has a non-naturally occurring level of hydroxylation relative to a naturally-occurring collagen. In some cases, fewer than 10% of prolines present in the non-naturally occurring polypeptide are hydroxylated. In some cases, the non-naturally occurring polypeptide is non-hydroxylated. In some cases, the non-naturally occurring polypeptide has a non-naturally occurring level of glycosylation relative to a naturally-occurring collagen. In some cases, the non-naturally occurring polypeptide protein comprises less than 5 wt. % glycosylation.

In another aspect, a composition is provided comprising between 0.001% and 30% w/w of the non-naturally occurring polypeptide of any one of the preceding. In some cases, the composition is formulated for consumption by an individual. In some cases, the composition is a nutraceutical. In some cases, the individual is a human.

In another aspect, a method of improving the appearance of the skin, the hair, and/or the nails of a subject, and/or improving bone, muscle, and/or joint health in the subject is provided, the method comprising: administering to the subject a composition of any one of the preceding compositions. In some cases, the administering comprises orally administering to the subject.

In yet another aspect, a recombinant cell is provided containing therein at least one copy of a heterologous nucleic acid sequence encoding a non-naturally occurring polypeptide of any one of the preceding. In some cases, the recombinant cell is a microbial cell. In some cases, the microbial cell is a bacterial cell. In some cases, the bacterial cell is of the species *Escherichia coli*. In some cases, the recombinant cell lacks an enzyme that hydroxylates one or more amino acids of the non-naturally occurring polypeptide. In some cases, the recombinant cell lacks prolyl 4-hydroxylase and/or prolyl 3-hydroxylase. In some cases, the heterologous nucleic acid sequence comprises a nucleic acid sequence having at least 80% sequence identity to any one of SEQ ID NOs: 1, 3, 5, 7, 9, 11, and 25-30. In some cases, the heterologous nucleic acid sequence comprises a nucleic acid sequence having at least 85% sequence identity to any one of SEQ ID NOs: 1, 3, 5, 7, 9, 11, and 25-30. In some cases, the heterologous nucleic acid sequence comprises a nucleic acid sequence having at least 90% sequence identity to any one of SEQ ID NOs: 1, 3, 5, 7, 9, 11, and 25-30. In some cases, the heterologous nucleic acid sequence comprises a nucleic acid sequence having at least 95% sequence identity to any one of SEQ ID NOs: 1, 3, 5, 7, 9, 11, and 25-30. In some cases, the heterologous nucleic acid sequence comprises a nucleic acid sequence having at least 98% sequence identity to any one of SEQ ID NOs: 1, 3, 5, 7, 9, 11, and 25-30. In some cases, the non-naturally occurring polypeptide further comprises a secretion signal. In some cases, the recombinant cell secretes the non-naturally occurring polypeptide into the periplasm, into a culture media, or extracellularly. In some cases, the heterologous nucleic acid sequence is codon-optimized for expression in the recombinant cell. In some cases, the heterologous nucleic acid sequence is operably linked to an inducible promoter or a constitutive promoter. In some cases, the heterologous nucleic acid is or is contained in a plasmid. In some cases, the heterologous nucleic acid sequence is stably integrated into a chromosome of the recombinant cell.

In yet another aspect, a culture medium is provided comprising a recombinant cell of any one of the preceding. In some cases, the culture medium further comprises the non-naturally occurring polypeptide of any one of the preceding secreted from the recombinant cell.

The present disclosure further provides a recombinant cell containing therein at least one copy of a heterologous nucleic acid sequence encoding collagen selected from the group consisting of: *Gallus gallus* collagen or *Acipenser schrenckii* (Japanese sturgeon) collagen. In some embodiments, the recombinant cell is a microbial cell. In some embodiments, the microbial cell is a bacterial cell. In some embodiments, the bacterial cell is of the species *Escherichia coli*. In some embodiments, the heterologous nucleic acid sequence comprises any one of SEQ ID NOs: 1, 3, 5, 7, 9, 11, and 25-30.

In some embodiments, the collagen is a *Gallus gallus* Type 21 collagen. In some embodiments, the collagen is a *Acipenser schrenckii* Type 2 alpha 1 collagen. In some embodiments, the collagen is a non-naturally occurring collagen. In some embodiments, the collagen is a truncated collagen. In some embodiments, the collagen comprises an amino acid sequence according to any one of SEQ ID NOs: 2, 4, 6, and 8.

In some embodiments, the collagen further comprises a secretion signal sequence. In some instances, the secretion signal sequence comprises an amino acid sequence according to any one of SEQ ID NOs: 10, 12, 14, 16, 18, 20, 22, and 24. In some embodiments, the recombinant cell secretes the collagen into a culture media. In some embodiments, the recombinant cell secretes to the periplasm. In some embodiments, the recombinant cell secrets the collagen to the extracellular space.

In some embodiments, the heterologous nucleic acid sequence is codon-optimized for expression in the recombinant cell. In some embodiments, the heterologous nucleic acid sequence is operably linked to an inducible promoter or a constitutive promoter. In some embodiments, the heterologous nucleic acid is or is contained within a plasmid. In some embodiments, the heterologous nucleic acid sequence is stably integrated into the chromosome of the recombinant cell.

The present disclosure also provides a culture medium comprising a recombinant cell described herein. In some embodiments, the culture medium further comprises a recombinant collagen secreted from the recombinant cell.

The present disclosure also provides a recombinant protein comprising a sequence that has at least 90% sequence identity to a fragment of a collagen selected from the group consisting of: *Gallus gallus* collagen, and *Acipenser schrenckii* collagen. In some embodiments, the collagen is a *Gallus gallus* Type 21 collagen. In some embodiments, the collagen is a *Acipenser schrenckii* Type 2 alpha 1 collagen.

In some embodiments, the collagen is a non-naturally occurring collagen or fragment thereof. In some embodiments, the protein has a non-naturally occurring level of glycosylation (e.g., relative to a corresponding natural collagen). In some embodiments, the protein comprises less than 5 wt. % glycosylation (e.g., less than 3 wt. %, less than 1 wt. %, less than 0.5 wt. %, or less than 0.1 wt. %). In some embodiments, the protein is a truncated collagen. In some embodiments, the protein comprises an amino acid sequence according to any one of SEQ ID NOs: 2, 4, 6, and 8 (or having a sequence identity of at least 90% thereof, at least 95% thereof, at least 98% thereof, or the like).

In some embodiments, the collagen further comprises a secretion signal sequence. In some embodiments, the secretion signal sequence comprises an amino acid sequence according to SEQ ID NO: 10, 12, 14, 16, 18, 20, 22, and 24.

The present disclosure also provides a composition comprising a recombinant protein as disclosed herein. In some embodiments, the composition further comprises a culture media. Additionally and/or alternatively, the composition further comprises a recombinant cell as disclosed herein. In some embodiments, the recombinant cell is a microbial cell. In some embodiments, the microbial cell is a bacterial cell. In some embodiments, the bacterial cell is of the species *Escherichia coli*. In some embodiments, the recombinant cell comprises an integrated heterologous nucleic acid sequence encoding a collagen, a truncated collagen, or fragment thereof. In some embodiments, the heterologous nucleic acid sequence comprises any one of SEQ ID NOs: 1, 3, 5, 7, and 25-30.

The present disclosure also provides a process for purifying a recombinant collagen, the process comprises incubating a recombinant cell described herein in a culture media wherein the recombinant cell secretes the recombinant collagen into the culture media, collecting the culture media comprising the recombinant collagen secreted thereto, and purifying the recombinant collagen from the culture media.

The present disclosure also provides a recombinant collagen purified from the culture medium disclosed in the process herein. In some embodiments, the recombinant collagen has a purity of at least 80%, at least 85%, at least 90%, at least 95%, or at least 99%.

The present disclosure also provides an expression vector comprising a nucleic acid sequence encoding a non-naturally occurring truncated collagen operably linked to a promoter, wherein the non-naturally occurring truncated collagen is selected from the group consisting of: *Gallus gallus* collagen and *Acipenser schrenckii* collagen. In some embodiments, the nucleic acid sequence comprises any one of SEQ ID NOs: 1, 3, 5, 7, and 25-30. In some embodiments, the *Gallus gallus* collagen is Type 21 collagen. In some embodiments, the *Acipenser schrenckii* collagen is Type 2 alpha 1 collagen.

In some embodiments, the expression vector further comprises a nucleic acid sequence encoding a secretion signal sequence. In some embodiments, the nucleic acid sequence encoding the secretion signal sequence comprises any one of SEQ ID NOs: 11, 13, 15, 17, 19, 21, and 23. In some embodiments, the nucleic acid sequence is codon optimized for expression in a cell.

The present disclosure also provides a composition comprising a recombinant collagen disclosed herein, formulated for consumption by an individual. In some embodiments, the composition is a nutraceutical. In some embodiments, the individual is a human. In some embodiments, the composition comprises from 0.1% to 10% recombinant collagen. In some embodiments, the composition comprises at least 50% of recombinant collagen. In some embodiments, the composition comprises from 70% to 99% of recombinant collagen. In some embodiments, the composition further comprises at least one of a carrier and a preservative.

The present disclosure also provides a method of improving the appearance of the skin, the hair, and/or the nails of a subject by administering to a subject the composition disclosed herein. In some embodiments, the step of administering comprises orally administering to the subject.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the subject matter disclosed herein are set forth with particularity in the appended claims. A better understanding of the features and advantages of the subject matter disclosed herein will be obtained by reference to the following detailed description that sets forth illustrative embodiments, in which the principles of the subject matter disclosed herein are utilized, and the accompanying drawings of which:

FIG. 6 discloses SEQ ID NOS: 33 and 34, respectively, in order of appearance.

DETAILED DESCRIPTION

Definitions

Figure 1:
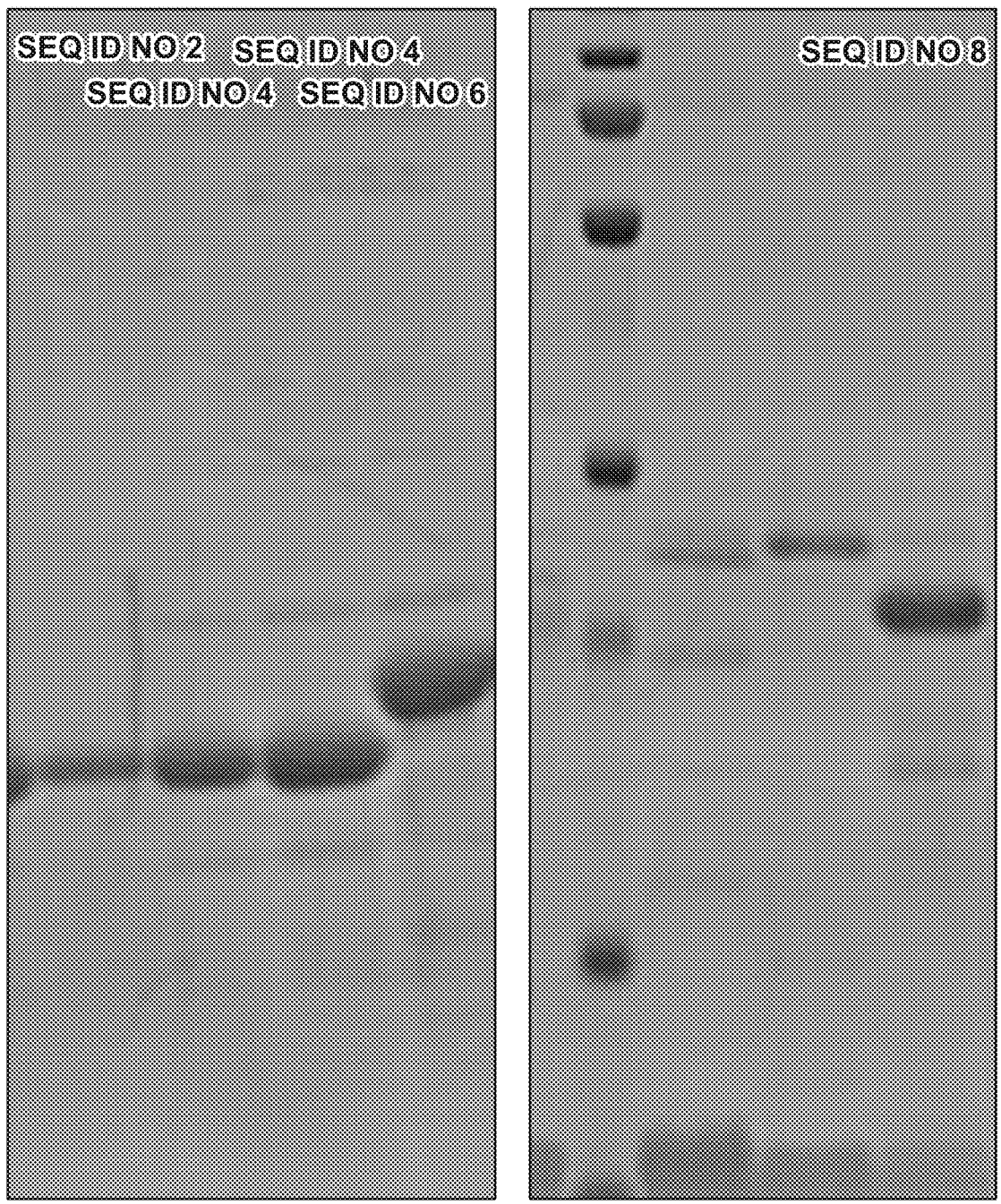
FIG. 1 shows an image of two SDS-PAGE gels showing bands of collagen proteins in supernatant samples from microbial cell cultures. The identities of each protein are indicated above each band.

The terminology used herein is for the purpose of describing particular cases only and is not intended to be limiting. As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The terms "about" or "approximately" mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual", "patient", or "subject" are used interchangeably herein. None of the terms require or are limited to a situation characterized by the supervision (e.g., constant or intermittent) of a health care worker (e.g., a doctor, a registered nurse, a nurse practitioner, a physician's assistant, an orderly, or a hospice worker).

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of". The phrase "consisting essentially of" is used herein to require the specified feature(s) as well as those which do not materially affect the character or function of the claimed disclosure. As used herein, the term "consisting" is used to indicate the presence of the recited feature alone.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as any individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as any individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terms "treatment of", "treating", "applying", "palliating" or "ameliorating" are used herein interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease or condition, or to a patient reporting one or more of the physiological symptoms of a disease, even though a diagnosis of this disease has not been made.

The terms "subject", "individual", or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "truncated collagen" as used herein generally refers to a polypeptide that is smaller than a full-length (e.g., natural) collagen wherein one or more portions of the full-length (e.g., natural) collagen is not present. The non-naturally polypeptides provided herein may be truncated at the C-terminal end, the N-terminal end, truncated by removal of internal portion(s) of the full-length collagen sequence (e.g., an internal truncation), truncated at both the C-terminal end and the N-terminal end, or may have one or both of a C-terminal truncation and an N-terminal truncation as well as an internal truncation. In a non-limiting embodiment, a truncated collagen may comprise an amino acid sequence according to SEQ ID NO: 2, or a homolog thereof. In another non-limiting embodiment, a truncated collagen may comprise an amino acid sequence according to SEQ ID NO: 8, or a homolog thereof.

When used in reference to an amino acid position, a "truncation" is inclusive of said amino acid position. For example, an N-terminal truncation at amino acid position 100 of a full-length protein means a truncation of 100 amino acids from the N-terminus of the full-length protein (i.e., the truncated protein is missing amino acid positions 1 through 100 of the full-length protein). Similarly, a C-terminal truncation at amino acid position 901 of a full-length protein (assuming a 1000 amino acid full-length protein) means a truncation of 100 amino acids from the C-terminus (i.e., the truncated protein is missing amino acid positions 901 through 1000 of the full-length protein). Similarly, an internal truncation at amino acid positions 101 and 200 means an internal truncation of 100 amino acids of the full-length protein (i.e., the truncated protein is missing amino acid positions 101 to 200 of the full-length protein).

The section headings used herein are for organizational purposes only and are not to be construed as limiting the subject matter described.

Provided in certain embodiments herein are, by way of non-limiting example, compositions, methods, and systems for manufacturing non-naturally occurring polypeptides, such as, e.g., animal-free collagen polypeptides or collagen-like polypeptides, as well as collagen fragments, and/or truncated collagens, such as that are expressed in and/or by genetically engineered microorganisms. Thus, in various aspects of the disclosure, the non-naturally occurring polypeptides provided herein include collagen or collagen-like polypeptides, recombinant collagens, collagen fragments, or truncated collagens. In certain embodiments, the non-naturally occurring polypeptides described herein (e.g., recombinant collagens, collagen fragments, or truncated collagens) are derived from any suitable source, such as from mammalian or non-mammalian sources. For example, in some embodiments, the non-naturally occurring polypeptides described herein (e.g., recombinant collagens, collagen fragments, or truncated collagens), or at least a portion thereof, are derived from (e.g., modified, truncated, fragments of, or the like) collagens of a bird or an avian animal (e.g., *Gallus gallus* collagen), a freshwater- or saltwater-fish (e.g., *Acipenser schrenckii* collagen), or any combination thereof.

The non-naturally occurring polypeptides provided herein are not normally found in nature. Generally, the non-naturally occurring polypeptides described herein exhibit one or more differences from naturally occurring collagens. In certain aspects, the non-naturally occurring polypeptides provided herein may have a different amino acid sequence from naturally occurring polypeptides (e.g., a truncated collagen). In some cases, the non-naturally occurring polypeptides may have a different structure from a naturally occurring collagen. The quaternary structure of natural collagen is a triple helix, typically composed of three polypeptides. In some aspects, the non-naturally occurring polypeptides described herein may not have or may not form a quaternary structure of natural collagen. For example, in some instances, the non-naturally occurring polypeptides described herein may not form the stable triple helical structure of naturally occurring collagen. In certain instances, of the three polypeptides that form natural collagen, two are usually identical and are designated as the alpha chain. The third polypeptide is designated as the beta chain. In certain instances, a typical natural collagen can be designated as AAB, wherein the collagen is composed of two alpha ("A") strands and one beta ("B") strand. In some aspects, the non-naturally occurring polypeptides described herein do not have the AAB structure of natural collagen. In some instances, the non-naturally occurring polypeptides described herein are free from or substantially free from different collagen chains (e.g., a non-naturally occurring polypeptide described herein may comprise an alpha chain collagen and may be free or substantially free from a beta chain collagen). In some aspects, the non-naturally occurring polypeptides described herein are monomeric (e.g., do not form multimeric structures). In other aspects, the non-naturally occurring polypeptides described herein may, in some instances, form multimeric structures with identical monomers (e.g., homodimers, homotrimers, etc.).

In some aspects, the non-naturally occurring polypeptides are recombinant polypeptides (e.g., prepared recombinantly in a host cell). The non-naturally occurring collagen is, in one embodiment, a truncated collagen. Other non-naturally occurring collagen polypeptides include chimeric collagens. A chimeric collagen is a polypeptide wherein one portion of a collagen polypeptide is contiguous with a portion of a second collagen polypeptide. For example, a collagen molecule comprising a portion of a collagen from one species contiguous with a portion of a collagen from another species is a chimeric collagen. In another embodiment, the non-naturally occurring collagen comprises a fusion polypeptide that includes additional amino acids such as a secretion tag, histidine tag, green fluorescent protein, protease cleavage site, GEK repeats, GDK repeats, and/or beta-lactamase.

In some embodiments, the non-naturally occurring polypeptides (e.g., recombinant polypeptides) provided herein have a non-naturally occurring level of glycosylation, for example, relative to a corresponding natural collagen or naturally present collagen. For example, in some embodiments, the non-naturally occurring polypeptide (e.g., recombinant polypeptide) comprises less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. %, less than 0.9 wt. %, less than 0.8 wt. %, less than 0.7 wt. %, less than 0.6 wt. %, less than 0.5 wt. %, less than 0.4 wt. %, less than 0.3 wt. %, less than 0.2 wt. %, or less than 0.1 wt. % glycosylation. Alternatively and/or additionally, the non-naturally occurring polypeptide (e.g., recombinant polypeptide) comprises less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of total glycosylation of the corresponding natural collagen or naturally present collagen. For example, where the naturally present collagen ABC from a species XYZ has 20 glycosylations (throughout the full length of the collagen ABC or a portion thereof), it is contemplated that the non-naturally occurring polypeptide (e.g., recombinant polypeptide) comprises less than 19, 18, 17, 16, 15, 14, 13, 12, 11, 10, 9, 8, 7, 6, 5, 4, 3, 2, or 1 glycosylations. In some embodiments, those lower levels of glycosylation can be specific to one or more types of glycosylation (e.g., O-glycosylation or N-glycosylation, etc.) and/or the glycosylation residues (e.g., galactosylhydroxylysine (Gal-Hyl), glucosyl galactosylhydroxylsine (GlcGal-Hyl), etc.). Non-naturally occurring polypeptides produced recombinantly (e.g., in a recombinant host cell), in some instances, may have a glycosylation level and/or a glycosylation pattern that differs from naturally occurring collagen.

In some aspects, a non-naturally occurring polypeptide provided herein has a non-naturally occurring amount of hydroxyprolines. In some cases, a non-naturally occurring polypeptide provided herein lacks hydroxyprolines. In some cases, a non-naturally occurring polypeptide provided herein comprises fewer hydroxyprolines than a naturally-occurring collagen. Hydroxyprolines include, without limitation, 3-hydroxyproline, 4-hydroxyproline, and 5-hydroxyproline. In some cases, less than about 50% (e.g., less than about 45%, less than about 40%, less than about 35%, less than about 30%, less than about 25%, less than about 20%, less than about 15%, less than about 10%, or less) of the prolines present in the amino acid sequence of a non-naturally occurring polypeptide provided herein are hydroxyprolines. In some aspects, a non-naturally occurring polypeptide produced recombinantly (e.g., in a recombinant host cell) may have fewer hydroxyprolines than a naturally occurring collagen. In some cases, a recombinant polypeptide as provided herein is recombinantly expressed in a recombinant host cell (e.g., bacterial cell) that lacks an enzyme that hydroxylates one or more amino acids (e.g., proline) of the recombinant polypeptide. In some cases, a recombinant polypeptide as provided herein is recombinantly expressed in a host cell (e.g., bacterial cell) that lacks prolyl 4-hydroxylase and/or prolyl 3-hydroxylase.

In some aspects, the non-naturally occurring polypeptides provided herein lack or substantially lack lysyl oxidation. Lysyl oxidation involves the conversion of lysine residues into highly reactive aldehydes that can form cross-links with other proteins. Naturally occurring collagens may have some level of lysyl oxidation. Thus, the non-naturally occurring polypeptides may be different from natural collagens in that they lack or substantially lack lysyl oxidation.

Generally, the non-naturally occurring polypeptides provided herein (e.g., truncated collagens) may have a function and/or provide a benefit (e.g., as provided herein) similar or substantially similar to that of a natural or a full-length collagen. In some cases, the non-naturally occurring polypeptides provided herein (e.g., truncated collagens) may have improved or increased function and/or benefit (e.g., as provided herein) as compared to a natural or a full-length collagen.

The non-naturally occurring polypeptides disclosed herein often have advantageous properties related to their monomeric structure and/or lack of amino acids capable of cross-linking with other collagen strands, e.g., the lack of hydroxyproline residues. In addition, collagen hydrolysates of the non-naturally occurring polypeptides disclosed herein are also produced with increased solubility as compared to full-length or natural collagens. Moreover, monomeric structures, as opposed to natural triple helix collagens, are more readily digestible and bioavailable, or broken down by digestive proteases. Other advantageous properties include improved physical properties in liquid compositions and in purification processes, since full-length or natural collagens or collagen strands interact to form stronger structures that can precipitate due to the presence of hydroxyproline residues.

In certain preferred embodiments, the non-naturally occurring polypeptides provided herein (e.g., truncated collagens) comprise an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to at least a portion of the naturally existing mammalian or non-mammalian collagens from which those are derived from. In some instances, a portion or portions of a natural amino acid sequence is deleted, but the remainder of the sequence is substantially similar or identical to the natural amino acid sequence. In certain exemplary embodiments, the non-naturally occurring polypeptide has an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a *Gallus gallus* Type 21 alpha 1 collagen or fragment thereof. In another example, the non-naturally occurring polypeptide has an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to a *Acipenser schrenckii* Type 2 alpha 1 collagen fragment.

In some embodiments, the recombinant protein is a truncated collagen. In certain instances, a truncated collagen is a polypeptide that is smaller than a full-length (e.g., natural) collagen wherein one or more portions (e.g., internal and/or terminal portion(s)) of the full-length (e.g., natural) collagen is not present. In various instances, the non-naturally occurring polypeptides provided herein (e.g., truncated collagens) are truncated at the C-terminal end, the N-terminal end, truncated by removal of internal portion(s) of the full-length collagen polypeptide (e.g., internal truncation), truncated at both the C-terminal end and the N-terminal end, or comprise one or both of a C-terminal truncation and an N-terminal truncation as well as an internal truncation. In some instances, the non-naturally occurring polypeptide is a fragment of a naturally occurring collagen that retains at least 50%, at least 60%, at least 70%, at least 80%, at least 90% of a function (e.g., of interest) of natural or naturally-present corresponding collagens. In some instances, the term truncated collagen is interchangeably used with the term collagen fragment. In some instances, the truncated collagen includes any contiguous collagen fragments that are at least 10%, at least 20%, at least 30%, at least 40%, at least 50%, at least 60%, at least 70%, at least 80% of full-length natural or naturally-present corresponding collagens. In some embodiments, the truncation is an internal truncation, a truncation at the N-terminal portion of the collagen, a truncation at the C-terminal portion of the collagen, a truncation of an internal portion, or a truncation at both the C-terminal end and the N-terminal end. A truncated collagen provided herein may be truncated by from 50 amino acids to 1000 amino acids, from 50 amino acids to 950 amino acids, from 50 amino acids to 900 amino acids, from 50 amino acids to 850 amino acids, from 50 amino acids to 800 amino acids, from 50 amino acids to 750 amino acids, from 50 amino acids to 700 amino acids, from 50 amino acids to 650 amino acids, from 50 amino acids to 600 amino acids, from 50 amino acids to 550 amino acids, from 50 amino acids to 500 amino acids, from 50 amino acids to 450 amino acids, from 50 amino acids to 400 amino acids, from 50 amino acids to 350 amino acids, from 50 amino acids to 300 amino acids, from 50 amino acids to 250 amino acids, from 50 amino acids to 200 amino acids, from 50 amino acids to 150 amino acids, or from 50 amino acids to 100 amino acids. In another embodiment, a truncated collagen is truncated by 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900, 950, or 1000 amino acids.

A non-naturally occurring polypeptide (e.g., truncated collagen) disclosed herein may comprise a truncation relative to a full-length (e.g., natural) collagen. In some embodiments, a truncated collagen disclosed herein may comprise a truncation relative to a full-length (e.g., natural) chicken (*Gallus gallus*) type 21 alpha 1 collagen (e.g., SEQ ID NO: 31). In some embodiments, a truncated collagen disclosed herein may comprise the amino acid sequence of SEQ ID NO: 31 with an N-terminal truncation, a C-terminal truncation, an internal truncation, or a combination thereof. In some embodiments, a truncated collagen disclosed herein may comprise a truncation relative to a full-length (e.g., natural) Japanese sturgeon (*Acipenser schrenckii*) type 2 alpha 1 collagen (e.g., SEQ ID NO: 32). In some embodiments, a truncated collagen disclosed herein may comprise the amino acid sequence of SEQ ID NO: 32 with an N-terminal truncation, a C-terminal truncation, an internal truncation, or a combination thereof. Non-limiting examples of full-length (e.g., natural) collagens are provided in Table 1 below.

In other embodiments, polypeptides may be truncated collagen polypeptides comparable to fish collagens, including from other species of sturgeon, or from other species producing roe suitable for caviar, including salmon, steelhead, trout, lumpfish, whitefish, or carp, as well as other fish such as tilapia and sharks. Suitable comparable sequences from *Acipenser schrenckii* (Japanese sturgeon) include NCBI accession numbers BA058965.1, BA058966.1, BA058967.1, BAT51012.1, BAR72360.1, BAR72359.1, BAR72358.1, BAR72357.1 and BAR72356.1. Suitable sequences from *Acipenser ruthenus* (Sterlet sturgeon) include NCBI accession numbers A0A444UGWO, A0A444TZM6, A0A444UC45, A0A444UC53, A0A662YTX1, A0A662Z270, A0A662YZ39, A0A444U1F5, A0A444UJK3, A0A444UNUO, X5HZZ7, X5IHC1, A0A444UPK8, A0A444UBS1, A0A444UYQ7, A0A444TWQ3, A0A444ULY4, A0A444TZ23, A0A662YS48, A0A444U4C8, A0A444UD64, A0A662YX10, A0A662YXI2, A0A444TXQ4, A0A444TZ42, A0A444U8N8, A0A444UJU3, A0A444UQ51, A0A444U2T2, A0A662YJ50, A0A444V1V9, A0A444V113, A0A662YWR6, A0A662YW91, A0A444U5J5, A0A662YR93, A0A444UJBO, A0A444UFS4, A0A444UVK2, A0A444UJU1, A0A444ULY9, A0A444UKA7, A0A444U5L7, A0A444V6M4, A0A444V788, A0A444UFS9, A0A444UVP7, A0A444U4D9, A0A444UHN6, A0A662YJC1, A0A444V1E8, A0A444UPM0, A0A662YU87, A0A444TZS8, A0A444U200, A0A444V2E3, A0A662YXD3, A0A662YQA4, A0A444U1H9, A0A444V715, A0A444UFX8, A0A444V7B8, A0A444U2K4, A0A444V762, A0A444UQ49, A0A662YMD3, A0A662YWF2, A0A444UE44, A0A444UAR6, A0A444UX46, A0A444U5P4, A0A662YRG8, A0A444USC3, A0A444UK09, A0A444UNQ7, A0A444UN69, A0A444V5D9, E6Y298, A0A444TZY1, A0A444TYSO, and E6Y299.

P13731, A0A1D5PFEO, A0A3Q2TXZ7, Q5FY72, A0A1D5PR16, A0A1D5PKR6, F1NDF5, Q90589, P08125, F1NRH2, P32017, A0A1D5PW49, Q90800, P12108, E1C353, Q7LZR2, P02460, A0A1L1RNI7, Q90796, P12106, F1NQ20, Q919K3, P20785, A0A1D5PWN6, P15988, P12105, F1NIL4, O93419, P02467, A0A5H1ZRJ7, A0A1D5PKQ4, A0A5H1ZRK9, Q90W37, A0A1D5NY11, A0A1D5P959, P02457, A0A1D5PYU1, A0A1D5PE57, Q9OZAO, Q90584, A0A1L1RZW7, A0A1D5NVMO, A0A1D5P8P3, F1NIP0, F1P2Q3, A0A1D5PE74, Q9IAU4, A0A3Q2TTC1, F1NHH4, P32018, A0A1D5P0F4, R4GHP9, A0A3Q2UD12, A0A3Q2UMJ2, A0A3Q2U4U7, F1NX22, A0A1D5P8I8, A0A1L1RPW4, P13944, P15989, F1P2F0, A0A1D5PGD5, and A0A3Q3AR07.

TABLE 1

Full-length collagen amino acid sequences

| Collagen | Amino Acid Sequence |
|---|---|
| Gallus gallus (chicken) type 21 alpha 1 collagen | MAQLLRLFQTLLILLLRDYISAEDGETRASCRTAPADLVFILDGSYSVGPENFEIIKSWL VNITRNEDIGPKFIQVGVVQYSDYPVLEIPLGTHESTENLIKEMESIHYLGGNIKTGRAI QFAYDHLFAKSSRFLTKIAVVLIDGKSQDEVKDVAAEARKNKITLFAIGVGSEIEEDELK AIANKPSSTYVEYVEDYIAISRIKEVIKQKLCEESVCPTRIPVAARDEKGEDILVGLGVK KRVKKRIQIPTTNAKAYEVISRVDLSELTRNVEPEGLPPSYVEVSTQRFKVKKTWDLWRV LSLDKRPQIAVTINGEEKTLSETTTSLINGTQVITFAAPRVKTLFDEGWHQIRLLVTEDF VTLYIDDQEIETKPLHPVLGIYISGLTQIGKYSGKEETVQFDIQKLRIYCDPEQNNRETV CEIPGENGECMNGPSDVGSTPAPCICPPGKGQGPPGPKGDPGQPGNHGYPGQPGPDGKPGY QGSAGTPGIPGTPGVQGPRGLPGIKGEPGKDGTKGDRGLPGFPGLHGMPAPKGERGPKGD QGVPGIYGKKGSKGEKGDTGFPGMPGRSGDPGRSGKDGLPGSPGFKGEVGQPGSPGLEGH RGEPGIPGIPGNQGAKGQKGEIGPPGLPGAKGSPGETGLMGPEGSFGLPGAPGPKGDKGE PGLQGKPGSSGAKGEPGGPGAPGEPGYPGIPGTQGIKGDKGSQGESGIQGRKGEKGRQGN PGLQGTEGLRGEQGEKGEKGDPGIRGINGQKGESGIQGLVGPPGVRGQPGDRGPPGPPGS DGKPAREFSEEFIRQVCSDVLRTQLPVILQSGRLQNCNHCQSQSASPGLPGPPGPRGPEG PRGFPGLPGNDGVPGLTGIPGRPGARGTRGLPGKNGAKGNQGIGVPGIQGPPGPPGPEGP PGMSKEGRPGERGQPGKDGDRGSPGMPGPVGPPGICDPSLCFSVIVGRDPFRKGPNY (SEQ ID NO: 31) |
| Acipenser schrenckii (Japanese sturgeon) type 2 alpha 1 collagen | MFSFVDSRTVLLLAAIQLCLLAVVKCQDVEVQQPGRKGQKGEPGDITDVVGPRGPGGPMG PPGEQGPRGERGDKGDKGGPGPRGRDGEPGTPGNPGPPGPPGPNGPPGLGGNFAAQMAGG FDEKAGGAQMGVMQGPMGPMGPRGPPGPTGAPGPQGFQGNPGEPGEPGAAGPLGPRGPPG PSGKPGEDGEAGKPGKSGERGSPGPQGARGFPGTPGLPGIKGHRGYPGLDGAKGEAGAAG SKGEAGSSGENGAPGPMGPRGLPGERGRNGPSGAAGARGNDGLPGPAGPPGPVGPAGAPG FPGSPGSKGEAGPTGARGPEGAQGPRGESGTPGSPGPSGASGNPGTDGIPGAKGSAGAPG IAGAPGFPGPRGPPGPQGATGPLGPKGQQGDPGIPGFKGEHGPKGEHGPAGPQGAPGPAG EEGKRGARGEPGAAGPLGPPGERGAPGNRGFPGQDGLAGPKGAPGERGQPGVGGPKGANG DPGRPGEPGLPGARGLTGRPGDAGPQGKGGPSGAAGEDGRPGPPGPQGARGQPGVMGFPG PKGANGEPGKAGEKGLVGPPGLRGLSGKDGETGAAGPPGPSGPAGERGEQGPPGPSGFQG LPGPPGPPGEGGKPGDQGVPGEAGAAGRAGPRGERGFPGERGSPGAQGLQGPRGLPGTPG TDGPKGATGPSGALGAQGPPGLQGMPGERGASGIAGAKGDRGDVGEKGPEGASGKDGSRG LTGPIGPPGPAGPNGEKGESGPSGPPGAAGTRGAPGDRGENGPPGPAGPAGPPGADGQPG AKGEQGEGGQKGDAGAPGPQGPSGAPGPQGPTGVSGPKGARGAQGPPGATGFPGAAGRVG PPGPNGNPGPSGPAGSAGKDGPKGVRGDAGPPGRAGDAGLQGAAGPPGEKGEPGEDGPPG PDGPSGPQGLGGNRGIVGLPGQRGERGFPGLPGPSGEPGKQGAPGGAGDRGPPGPVGPPG LSGPSGEPGREGNPGSDGPPGRDGSAGIKGDRGQTGPAGAPGAPGAPGSPGPVGPTGKQG DRGESGAQGPAGPSGPAGARGMAGPQGPRGDKGEAGETGERGQKGHRGFTGLQGLPGPPG TAGDQGAAGPAGPTGARGPPGPVGPHGKDGSNGQPGPIGPPGPRGRSGEVGPAGPPGNAG PPGPPGPPGPGIDMSAFAGLAAPEKAPDPMRYMRADEASSSLRQHDAEVDATLKSINNQI ENIRSPEGSKKNPARTCRDLKLCHPDWKSGDYWIDPNQGCAVDAIKVFCNMESGETCVYP NPASIPRKNWWTSKSADCKHVWFGETMNGGFHFSYGDDSLAPNTASIQMTFLRLLSTEAS QNLTYHCKNSIAYMDQSAGNLKKAVLLQGSNDVEIRAEGNSRFTYNVLEDGCTKHTDRWG KTVIEYKSQKTSRLPIVDIAPLDIGGSDQEFGVDIGPVCY (SEQ ID NO: 32) |

In other embodiments, polypeptides may be truncated collagen polypeptides comparable to chicken collagens, or other poultry collagens, such as from domestic fowls, including chickens, turkeys, geese, and ducks. Suitable comparable sequences from Gallus gallus (chicken) include NCBI accession numbers V9GZR2, Q9PSS5, A0A3Q2UDI3, Q90802, A0A1D5PNH7, Q4TZW6, Q90803, Q91014, A0A1D5PPIO, A0A1D5P1A5, A0A3Q2U6K2, A0A3Q2U8F9, Q90689, A0A3Q2U3U6, In some cases, a non-naturally occurring polypeptide (e.g., truncated collagen) as described herein may comprise the amino acid sequence of SEQ ID NO: 31 (or an amino acid sequence having at least 80% (e.g., at least 85%, at least 90%, at least 95%, at least 98%) sequence identity thereto) with an N-terminal truncation at any amino acid position (e.g., relative to SEQ ID NO: 31) from amino acid positions 1 to 537; from amino acid positions 1 to 542; from amino acid positions 1 to 547; from amino acid positions 1 to 552;

from amino acid positions 1 to 557; from amino acid positions 1 to 562; from amino acid positions 1 to 567; from amino acid positions 1 to 572; or from amino acid positions 1 to 577. In some cases, a non-naturally occurring polypeptide (e.g., truncated collagen) as described herein may comprise the amino acid sequence of SEQ ID NO: 31 (or an amino acid sequence having at least 80% (e.g., at least 85%, at least 90%, at least 95%, at least 98%) sequence identity thereto) with a C-terminal truncation at any amino acid position (relative to SEQ ID NO: 31) from amino acid positions 726 to 957; from amino acid positions 731 to 957; from amino acid positions 736 to 957; from amino acid positions 741 to 957; from amino acid positions 746 to 957; from amino acid positions 751 to 957; from amino acid positions 756 to 957; from amino acid positions 761 to 957; from amino acid positions 766 to 957; from amino acid positions 769 to 957; from amino acid positions 774 to 957; from amino acid positions 779 to 957; or from amino acid positions 784 to 957. In some cases, a non-naturally occurring polypeptide as described herein (e.g., a truncated collagen) may comprise both an N-terminal truncation and a C-terminal truncation. For example, a non-naturally occurring polypeptide (e.g., truncated collagen) as described herein may comprise the amino acid sequence of SEQ ID NO: 31 (or an amino acid sequence having at least 80% (e.g., at least 85%, at least 90%, at least 95%, at least 98%) sequence identity thereto) with an N-terminal truncation at any amino acid position (e.g., relative to SEQ ID NO: 31) from amino acid positions 1 to 537; from amino acid positions 1 to 542; from amino acid positions 1 to 547; from amino acid positions 1 to 552; from amino acid positions 1 to 557; from amino acid positions 1 to 562; from amino acid positions 1 to 567; from amino acid positions 1 to 572; or from amino acid positions 1 to 577; and with a C-terminal truncation at any amino acid position (relative to SEQ ID NO: 31) from amino acid positions 726 to 957; from amino acid positions 731 to 957; from amino acid positions 736 to 957; from amino acid positions 741 to 957; from amino acid positions 746 to 957; from amino acid positions 751 to 957; from amino acid positions 756 to 957; from amino acid positions 761 to 957; from amino acid positions 766 to 957; from amino acid positions 769 to 957; from amino acid positions 774 to 957; from amino acid positions 779 to 957; or from amino acid positions 784 to 957. In a specific embodiment, a non-naturally occurring polypeptide (e.g., truncated collagen) disclosed herein may comprise the amino acid sequence of SEQ ID NO: 31 (or an amino acid sequence having at least 80% (e.g., at least 85%, at least 90%, at least 95%, at least 98%) sequence identity thereto) with an N-terminal truncation at amino acid position 557 (relative to SEQ ID NO: 31); and with a C-terminal truncation at amino acid position 746 (relative to SEQ ID NO: 31). In another specific embodiment, a non-naturally occurring polypeptide (e.g., truncated collagen) disclosed herein may comprise the amino acid sequence of SEQ ID NO: 31 (or an amino acid sequence having at least 80% (e.g., at least 85%, at least 90%, at least 95%, at least 98%) sequence identity thereto) with an N-terminal truncation at amino acid position 557 (relative to SEQ ID NO: 31); and with a C-terminal truncation at amino acid position 769 (relative to SEQ ID NO: 31).

In some cases, a non-naturally occurring polypeptide (e.g., truncated collagen) as described herein may comprise the amino acid sequence of SEQ ID NO: 32 (or an amino acid sequence having at least 80% (e.g., at least 85%, at least 90%, at least 95%, at least 98%) sequence identity thereto) with an N-terminal truncation at any amino acid position (e.g., relative to SEQ ID NO: 32) from amino acid positions 1 to 660; from amino acid positions 1 to 665; from amino acid positions 1 to 670; from amino acid positions 1 to 675; from amino acid positions 1 to 680; from amino acid positions 1 to 685; from amino acid positions 1 to 690; from amino acid positions 1 to 695; or from amino acid positions 1 to 700. In some cases, a non-naturally occurring polypeptide (e.g., truncated collagen) as described herein may comprise the amino acid sequence of SEQ ID NO: 32 (or an amino acid sequence having at least 80% (e.g., at least 85%, at least 90%, at least 95%, at least 98%) sequence identity thereto) with a C-terminal truncation at any amino acid position (relative to SEQ ID NO: 32) from amino acid positions 855 to 1420; from amino acid positions 860 to 1420; from amino acid positions 865 to 1420; from amino acid positions 870 to 1420; from amino acid positions 875 to 1420; from amino acid positions 880 to 1420; from amino acid positions 885 to 1420; from amino acid positions 890 to 1420; from amino acid positions 895 to 1420; or from amino acid positions 900 to 1420. In some cases, a non-naturally occurring polypeptide as described herein (e.g., a truncated collagen) may comprise both an N-terminal truncation and a C-terminal truncation. For example, a non-naturally occurring polypeptide (e.g., truncated collagen) as described herein may comprise the amino acid sequence of SEQ ID NO: 32 (or an amino acid sequence having at least 80% (e.g., at least 85%, at least 90%, at least 95%, at least 98%) sequence identity thereto) with an N-terminal truncation at any amino acid position (e.g., relative to SEQ ID NO: 32) from amino acid positions 1 to 660; from amino acid positions 1 to 665; from amino acid positions 1 to 670; from amino acid positions 1 to 675; from amino acid positions 1 to 680; from amino acid positions 1 to 685; from amino acid positions 1 to 690; from amino acid positions 1 to 695; or from amino acid positions 1 to 700; and with a C-terminal truncation at any amino acid position (relative to SEQ ID NO: 32) from amino acid positions 855 to 1420; from amino acid positions 860 to 1420; from amino acid positions 865 to 1420; from amino acid positions 870 to 1420; from amino acid positions 875 to 1420; from amino acid positions 880 to 1420; from amino acid positions 885 to 1420; from amino acid positions 890 to 1420; from amino acid positions 895 to 1420; or from amino acid positions 900 to 1420. In a specific embodiment, a non-naturally occurring polypeptide (e.g., truncated collagen) disclosed herein may comprise the amino acid sequence of SEQ ID NO: 32 (or an amino acid sequence having at least 80% (e.g., at least 85%, at least 90%, at least 95%, at least 98%) sequence identity thereto) with an N-terminal truncation at amino acid position 680 (relative to SEQ ID NO: 32); and with a C-terminal truncation at amino acid position 880 (relative to SEQ ID NO: 32).

In some cases, a non-naturally occurring polypeptide (e.g., truncated collagen) may comprise any amino acid sequence provided herein. In some cases, a non-naturally occurring polypeptide (e.g., truncated collagen) may consist of any amino acid sequence provided herein. In some cases, a non-naturally occurring polypeptide (e.g., truncated collagen) may consist essentially of any amino acid sequence provided herein. In specific embodiments, the non-naturally occurring polypeptide has or comprises an amino acid sequence of any one of SEQ ID NO: 2, SEQ ID NO: 4, SEQ ID NO: 6, and SEQ ID NO: 8. In some embodiments, a non-naturally occurring polypeptide (e.g., truncated collagen) comprises an amino acid sequence having at least 85%, at least 90%, at least 95%, or at least 98% sequence identity to any one of SEQ ID NO: 2, SEQ ID NO: 4, SEQ ID NO:

6, and SEQ ID NO: 8. In some embodiments, the non-naturally occurring polypeptide consists of or consists essentially of an amino acid sequence of any one of SEQ ID NO: 2, SEQ ID NO: 4, SEQ ID NO: 6, and SEQ ID NO: 8.

In some aspects, the non-naturally occurring polypeptide may include any chimeric collagen that includes at least one non-continuous collagen fragment. For example, the non-naturally occurring polypeptide can be a chimeric collagen in which a portion of N-terminus collagen is contiguous with a portion of C-terminus collagen where the portion of N-terminus collagen and the portion of C-terminus collagen are not contiguous in the natural or naturally-present corresponding collagens. In another example, the non-naturally occurring polypeptide can be a chimeric collagen in which a portion of C-terminus collagen is contiguous with a portion of N-terminus collagen (e.g., in a flipped or reverse order—C terminus collagen is located in the N-terminus of the portion of N-terminus collagen) where the portion of C-terminus collagen and the portion of N-terminus collagen are contiguous or non-contiguous in the natural or naturally-present corresponding collagens. In another example, the non-naturally occurring polypeptide can be a chimeric collagen in which one portion of a collagen polypeptide is contiguous with a portion of a second collagen polypeptide (e.g., a collagen molecule comprising a portion of a collagen from a first species contiguous with a portion of a collagen from a second species is a chimeric collagen, etc.).

Exemplary amino acid sequences of or nucleic acid sequences encoding the recombinant proteins are provided below:

```
A nucleotide sequence encoding a truncated collagen type 21 alpha 1
polypeptide from Gallus gallus (chicken)
                                                        SEQ ID NO: 1
GATACCGGTTTTCCGGGTATGCCTGGTCGTAGCGGTGATCCGGGTCGTAGCGGTAAAGATGGTCTGC

CTGGTAGCCCGGGTTTTAAAGGTGAAGTTGGTCAGCCAGGTAGCCCTGGTCTGGAAGGTCATCGTGG

TGAACCGGGTATTCCAGGTATTCCGGGTAATCAGGGTGCAAAAGGTCAGAAAGGCGAAATTGGTCCT

CCGGGTCTGCCAGGTGCCAAAGGTTCTCCGGGTGAAACCGGTCTGATGGGTCCTGAAGGTAGCTTTG

GCCTGCCTGGTGCACCGGGTCCGAAAGGTGACAAAGGTGAACCTGGTCTGCAGGGTAAACCGGGTAG

CAGCGGTGCAAAAGGCGAACCAGGTGGTCCGGGTGCTCCGGGTGAACCAGGCTATCCGGGTATTCCT

GGTACTCAGGGTATTAAAGGCGATAAAGGTAGCCAGGGTGAAAGCGGTATTCAGGGTCGTAAGGGTG

AAAAAGGCCGTCAGGGTAATCCAGGCCTGCAGGGCACCGAAGGTCTGCGTGGCGAACAGGGCGAAAA

AGGTGAGAAGGGTGACCCAGGCATTCGT

Amino acid sequence of a truncated collagen type 21 alpha 1
polypeptide from Gallus gallus (chicken)
                                                        SEQ ID NO: 2
DTGFPGMPGRSGDPGRSGKDGLPGSPGFKGEVGQPGSPGLEGHRGEPGIPGIPGNQGAKGQKGEIGP

PGLPGAKGSPGETGLMGPEGSFGLPGAPGPKGDKGEPGLQGKPGSSGAKGEPGGPGAPGEPGYPGIP

GTQGIKGDKGSQGESGIQGRKGEKGRQGNPGLQGTEGLRGEQGEKGEKGDPGIR

A nucleotide sequence encoding a truncated collagen type 21 alpha 1
polypeptide from Gallus gallus (chicken)
                                                        SEQ ID NO: 3
GATACTGGTTTCCCGGGGATGCCTGGGCGCTCAGGTGATCCGGGGCGTAGTGGAAAAG

ACGGTCTGCCGGGGTCCCCGGGCTTTAAGGGTGAGGTGGGTCAGCCCGGTAGTCCAGGT

TTAGAAGGTCACCGCGGAGAGCCCGGGATTCCAGGCATTCCTGGCAACCAGGGTGCCA

AGGGACAGAAAGGCGAAATTGGTCCGCCCGGCCTACCGGGCGCGAAAGGTTCTCCTGG

TGAAACCGGTCTCATGGGTCCGGAAGGTAGCTTCGGCCTGCCCGGCGCACCTGGTCCGA

AGGGCGATAAGGGGGAGCCTGGGCTGCAAGGTAAACCGGGTAGTTCTGGCGCCAAAGG

TGAACCCGGCGGTCCCGGTGCGCCAGGGGAACCAGGTTATCCTGGTATTCCTGGAACCC

AAGGAATTAAAGGTGACAAAGGCTCACAGGGCGAAAGTGGTATACAGGGTCGCAAGG

GCGAAAAAGGACGTCAGGGCAATCCAGGCCTGCAGGGTACTGAAGGCCTGCGTGGAGA

ACAGGGTGAGAAAGGTGAAAAAGGAGATCCTGGTATTCGC

Amino acid sequence of a truncated collagen type 21 alpha 1
polypeptide from Gallus gallus (chicken)
                                                        SEQ ID NO: 4
DTGFPGMPGRSGDPGRSGKDGLPGSPGFKGEVGQPGSPGLEGHRGEPGIPGIPGNQGAKGQKGEIGP

PGLPGAKGSPGETGLMGPEGSFGLPGAPGPKGDKGEPGLQGKPGSSGAKGEPGGPGAPGEPGYPGIP

GTQGIKGDKGSQGESGIQGRKGEKGRQGNPGLQGTEGLRGEQGEKGEKGDPGIR
```

-continued

The nucleotide sequence encoding a truncated collagen type 21
alpha 1 polypeptide from *Gallus gallus* (chicken)
SEQ ID NO: 5

GATACTGGTTTCCCGGGGATGCCTGGGCGCTCAGGTGATCCGGGGCGTAGTGGAAAAGACGG

TCTGCCGGGGTCCCCGGGCTTTAAGGGTGAGGTGGGTCAGCCCGGTAGTCCAGGTTTAGAAGGTCAC

CGCGGAGAGCCCGGGATTCCAGGCATTCCTGGCAACCAGGGTGCCAAGGGACAGAAAGGCGAAATTG

GTCCGCCCGGCCTACCGGGCGCGAAAGGTTCTCCTGGTGAAACCGGTCTCATGGGTCCGGAAGGTAG

CTTCGGCCTGCCCGGCGCACCTGGTCCGAAGGGCGATAAGGGGGAGCCTGGGCTGCAAGGTAAACCG

GGTAGTTCTGGCGCCAAAGGTGAACCCGGCGGTCCCGGTGCGCCAGGGGAACCAGGTTATCCTGGTA

TTCCTGGAACCCAAGGAATTAAAGGTGACAAAGGCTCACAGGGCGAAAGTGGTATACAGGGTCGCAA

GGGCGAAAAAGGACGTCAGGGCAATCCAGGCCTGCAGGGTACTGAAGGCCTGCGTGGAGAACAGGGT

GAGAAAGGTGAAAAGGAGATCCTGGTATTCGCGGCATTAACGGTCAAAAGGGTGAAAGTGGGATAC

AAGGTCTTGTCGGTCCGCCCGGAGTTAGAGGCCAG

Amino acid sequence of a truncated collagen type 21 alpha 1
polypeptide from *Gallus gallus* (chicken)
SEQ ID NO: 6

DTGFPGMPGRSGDPGRSGKDGLPGSPGFKGEVGQPGSPGLEGHRGEPGIPGIPGNQGAKGQKGEIGP

PGLPGAKGSPGETGLMGPEGSFGLPGAPGPKGDKGEPGLQGKPGSSGAKGEPGGPGAPGEPGYPGIP

GTQGIKGDKGSQGESGIQGRKGEKGRQGNPGLQGTEGLRGEQGEKGEKGDPGIRGINGQKGESGIQG

LVGPPGVRGQ

The nucleotide sequence encoding a truncated collagen type 2 alpha 1
polypeptide from *Acipenser schrenckii* (Japanese sturgeon)
SEQ ID NO: 7

GTCTGCAGGGTATGCCTGGTGAACGTGGTGCAAGCGGTATTGCCGGTGCAAAAGGTGATCGTGGTGA

TGTTGGTGAAAAAGGTCCGGAAGGTGCCAGCGGTAAAGATGGTAGCCGTGGTCTGACCGGTCCGATT

GGTCCGCCTGGTCCGGCAGGTCCGAATGGCGAAAAAGGTGAAAGCGGTCCGAGCGGTCCTCCGGGTG

CAGCAGGTACTCGTGGTGCACCGGGTGATCGCGGTGAAAATGGTCCACCGGGTCCTGCCGGTTTTGC

AGGTCCGCCAGGTGCAGATGGTCAGCCTGGTGCCAAAGGCGAACAAGGCGAAGGTGGTCAGAAAGGT

GATGCAGGCGCTCCGGGTCCGCAGGGTCCTTCTGGTGCACCTGGTCCTCAGGGTCCGACCGGTGTTT

CTGGTCCGAAAGGCGCACGTGGTGCCCAGGGTCCACCTGGTGCGACCGGTTTTCCTGGCGCAGCAGG

TCGTGTTGGTCCTCCAGGTCCTAATGGTAATCCGGGTCCAAGCGGTCCTGCAGGTAGCGCAGGCAAA

GATGGTCCTAAAGGTGTACGCGGTGATGCTGGTCCTCCTGGCCGTGCCGGTGATGCCGGT

Amino acid sequence of a truncated collagen type 2 alpha 1
polypeptide from *Acipenser schrenckii* (Japanese sturgeon)
SEQ ID NO: 8

GLQGMPGERGASGIAGAKGDRGDVGEKGPEGASGKDGSRGLTGPIGPPGPAGPNGEKGESGPSGPPG

AAGTRGAPGDRGENGPPGPAGFAGPPGADGQPGAKGEQGEGGQKGDAGAPGPQGPSGAPGPQGPTGV

SGPKGARGAQGPPGATGFPGAAGRVGPPGPNGNPGPSGPAGSAGKDGPKGVRGDAGPPGRAGDAG

The nucleotide sequence encoding a secretion signal sequence named
Secretion Signal Sequence 1
SEQ ID NO: 9

ATGAAAAAGATTTGGCTGGCGCTGGCTGGTTTAGTTTTAGCGTTTAGCGCATCGGCG

Amino acid sequence of a Secretion Signal Sequence 1
SEQ ID NO: 10

MKKIWLALAGLVLAFSASA

The nucleotide sequence encoding a secretion signal sequence named
Secretion Signal Sequence 2
SEQ ID NO: 11

ATGAAAAAGGTTTCATGCTGTTCACCCTCCTCGCTGCGTTCTCTGGTTTCGCGCAGGCT

Amino acid sequence of a Secretion Signal Sequence 2

-continued

MKKGFMLFTLLAAFSGFAQA
SEQ ID NO: 12

The nucleotide sequence encoding a secretion signal sequence named
Secretion Signal Sequence 3
SEQ ID NO: 13
ATGATGATCACCCTGCGTAAACTGCCGCTGGCTGTTGCTGTTGCTGCTGGTGTTATGTCTGCTCAGG

CTATGGCT

Amino acid sequence of a Secretion Signal Sequence 3
SEQ ID NO: 14
MMITLRKLPLAVAVAAGVMSAQAMA The nucleotide sequence encoding a secretion signal sequence named
Secretion Signal Sequence 4
SEQ ID NO: 15
ATGAAAAAAACCGCTATCGCTATCGCTGTTGCTCTGGCTGGTTTCGCTACCGTTGCTCAGGCT Amino acid sequence of a Secretion Signal Sequence 4
SEQ ID NO: 16
MKKTAIAIAVALAGFATVAQA The nucleotide sequence encoding a secretion signal sequence named
Secretion Signal Sequence 5
SEQ ID NO: 17
ATGAAAGTTAAAGTTCTGTCTCTGCTGGTTCCGGCTCTGCTGGTTGCTGGTGCTGCTAACGCT Amino acid sequence of a Secretion Signal Sequence 5
SEQ ID NO: 18
MKVKVLSLLVPALLVAGAANA The nucleotide sequence encoding a secretion signal sequence named
Secretion Signal Sequence 6
SEQ ID NO: 19
ATGAAACATCCTGTCTCTGTCTATGGTTGCTCTGTCTCTGTCTCTGGCTCTGGGTTCTGTTT

CTGTTACCGCT

Amino acid sequence of a Secretion Signal Sequence 6
SEQ ID NO: 20
MKKNILSLSMVALSLSLALGSVSVTA The nucleotide sequence encoding a secretion signal sequence named
Secretion Signal Sequence 7
SEQ ID NO: 21
ATGCTGAACCCGAAAGTTGCTTACATGGTTTGGATGACCTGCCTGGGTCTGACCCTGCCGTCTCAGG

CT

Amino acid sequence of a Secretion Signal Sequence 7
SEQ ID NO: 22
MLNPKVAYMVWMTCLGLTLPSQA The nucleotide sequence encoding a secretion signal sequence named
Secretion Signal Sequence 8
SEQ ID NO: 23
ATGAAACAGGCTCTGCGTGTAGCGTTCGGTTTCCTGATACTGTGGGCTTCTGTTCTGCACGCT Amino acid sequence of a Secretion Signal Sequence 8
SEQ ID NO: 24
MKQALRVAFGFLILWASVLHA A codon-optimized nucleotide sequence encoding a truncated collagen
type 2 alpha 1 polypeptide from Acipenser schrenckii
(Japanese sturgeon)
SEQ ID NO: 25
GGTCTGCAGGGTATGCCGGGTGAACGTGGTGCCAGCGGTATTGCAGGTGCCAAAGGTGATCGTGGTG

ATGTTGGTGAAAAAGGTCCGGAAGGTGCAAGCGGTAAAGATGGTAGCCGTGGTCTGACCGGTCCGAT

TGGTCCGCCGGGTCCGGCCGGTCCGAATGGTGAAAAAGGTGAAAGCGGTCCGAGCGGTCCGCCGGGT

GCAGCCGGTACCCGTGGTGCACCGGGTGATCGTGGTGAAAATGGTCCGCGGGTCCGGCCGGTTTTG

CAGGTCCGCCGGGTGCCGATGGTCAGCCGGGTGCAAAAGGTGAACAGGGTGAAGGTGGTCAGAAAGG

TGATGCCGGTGCACCGGGTCCGCAGGGTCCGAGCGGTGCCCCGGGTCCGCAGGGTCCGACCGGTGTT

AGCGGTCCGAAAGGTGCACGTGGTGCCCAGGGTCCGCCGGGTGCAACCGGTTTTCCGGGTGCCGCAG

-continued

GTCGTGTTGGTCCGCCGGGTCCGAATGGTAATCCGGGTCCGAGCGGTCCGGCAGGTAGCGCCGGTAA

AGATGGTCCGAAAGGTGTTCGTGGTGATGCAGGTCCGCCGGGTCGTGCCGGTGATGCAGGTTAA

A codon-optimized nucleotide sequence encoding a truncated
collagen type 2 alpha 1 polypeptide from *Acipenser schrenckii*
(Japanese sturgeon)

SEQ ID NO: 26

GGCCTGCAAGGCATGCCAGGCGAGCGCGGCGCGTCTGGCATCGCGGGCGCGAAGGGCGACCGCGGCG

ACGTGGGCGAGAAGGGCCCTGAGGGCGCGTCCGGCAAGGACGGCTCTCGCGGCCTGACAGGCCCAAT

CGGCCCTCCAGGCCCTGCGGGCCCAAACGGCGAGAAGGGCGAGTCCGGCCCTTCTGGCCCACCTGGC

GCGGCGGGCACACGCGGCGCGCCAGGCGACCGCGGCGAGAACGGCCCTCCAGGCCCTGCGGGCTTCG

CGGGCCCACCTGGCGCGGACGGCCAACCAGGCGCGAAGGGCGAGCAAGGCGAGGGCGGCCAAAAGGG

CGACGCGGGCGCGCCTGGCCCACAAGGCCCTTCTGGCGCGCCAGGCCCTCAAGGCCCAACAGGCGTG

TCCGGCCCTAAGGGCGCGCGCGGCGCGCAAGGCCCACCTGGCGCGACAGGCTTCCCAGGCGCGGCGG

GCCGCGTGGGCCCTCCAGGCCCTAACGGCAACCCAGGCCCTTCTGGCCCAGCGGGCTCCGCGGGCAA

GGACGGCCCTAAGGGCGTGCGCGGCGACGCGGGCCCACCTGGCCGCGCGGGCGACGCGGGCTGA

A codon-optimized nucleotide sequence encoding a truncated collagen
type 2 alpha 1 polypeptide from *Acipenser schrenckii*
(Japanese sturgeon)

SEQ ID NO: 27

GGTTTGCAAGGTATGCCAGGGGAACGGGGTGCGTCCGGGATAGCCGGGGCAAAAGGTGATCGAGGCG

ATGTAGGAGAAAAAGGCCCAGAAGGGGCGTCAGGTAAGGACGGATCTCGCGGCTTGACGGGACCTAT

CGGGCCTCCAGGTCCCGCCGGCCCTAATGGGAAAAAGGCGAGAGTGGGCCGTCTGGTCCGCCCGGC

GCCGCTGGCACACGTGGAGCGCCGGGCGATCGTGGTGAGAACGGACCACCGGGTCCTGCTGGTTTTG

CGGGACCTCCGGGAGCAGACGGCCAGCCGGGCGCTAAAGGTGAACAGGGTGAAGGTGGCCAAAAAGG

CGATGCAGGCGCACCGGGTCCGCAGGGCCCTTCAGGTGCACCGGGTCCACAGGGCCCAACTGGCGTT

TCAGGGCCGAAAGGCGCAAGAGGTGCTCAGGGTCCGCCCGGGGCAACTGGGTTTCCTGGAGCGGCCG

GCCGTGTTGGACCTCCGGGGCCGAACGGAAACCCTGGACCGTCTGGACCAGCCGGTTCAGCGGGTAA

GGATGGTCCTAAGGGTGTAAGGGGTGACGCAGGTCCCCCTGGACGTGCAGGGGATGCGGGGTAG

A codon-optimized nucleotide sequence encoding a truncated collagen
type 2 alpha 1 polypeptide from *Acipenser schrenckii*
(Japanese sturgeon)

SEQ ID NO: 28

GGGTTACAAGGTATGCCGGGAGAACGTGGAGCGTCAGGAATTGCTGGGGCCAAAGGTGATCGTGGTG

ATGTTGGCGAGAAAGGGCCCGAAGGCGCATCTGGTAAAGATGGCTCACGCGGGTTAACTGGACCAAT

CGGACCACCAGGCCCCGCTGGGCCTAATGGTGAAAAGGGTGAAAGTGGCCCTTCTGGACCCCCAGGA

GCCGCCGGTACACGTGGAGCGCCAGGCGATCGTGGCGAAAACGGACCGCCCGGACCTGCAGGTTTTG

CGGGACCCCCTGGAGCAGACGGCCAACCAGGAGCAAAAGGTGAGCAAGGTGAAGGTGGACAAAAGGG

AGATGCCGGAGCGCCAGGCCCCCAAGGCCCATCAGGAGCTCCAGGACCTCAAGGTCCAACTGGTGTA

TCAGGGCCTAAGGGTGCGCGCGGCGCTCAAGGACCGCCTGGCGCAACTGGCTTTCCGGGAGCTGCTG

GTCGTGTGGGCCCGCCTGGCCCAAACGGAAATCCAGGCCCTTCAGGCCCGGCGGGCTCAGCCGGAAA

AGACGGTCCGAAGGGAGTCCGTGGAGATGCGGGACCGCCAGGACGCGCTGGCGATGCAGGCTAA

A codon-optimized nucleotide sequence encoding a truncated collagen
type 2 alpha 1 polypeptide from *Acipenser schrenckii*
(Japanese sturgeon)

SEQ ID NO: 29

GGTTTACAGGGAATGCCAGGGGAACGCGGCGCCTCAGGGATTGCCGGTGCTAAAGGAGATCGTGGCG

ACGTGGGTGAAAAGGGTCCCGAGGGAGCATCAGGTAAGGATGGTTCCCGTGGTTTGACGGGACCTAT

TGGACCTCCGGGTCCTGCAGGTCCGAACGGCGAAAAGGGGGAAAGCGGGCCTAGTGGTCCACCCGGC

GCCGCAGGTACCCGTGGTGCCCCAGGCGACCGCGGGGAGAATGGACCGCCTGGCCCTGCCGGTTTTG

-continued

```
CGGGTCCTCCAGGAGCCGATGGGCAGCCCGGTGCAAAAGGAGAGCAGGGAGAGGGAGGTCAAAAGGG

AGATGCCGGCGCCCCGGGCCCTCAGGGACCAAGCGGTGCGCCAGGCCCCCAGGGTCCTACGGGTGTT

AGCGGGCCGAAAGGCGCACGCGGAGCGCAGGGCCCACCTGGTGCAACAGGCTTCCCAGGAGCTGCGG

GGCGCGTCGGACCTCCGGGACCCAATGGAAACCCAGGTCCGTCAGGGCCGGCAGGCTCCGCAGGGAA

AGATGGTCCCAAAGGCGTGCGTGGAGACGCAGGGCCCCCCGGACGCGCCGGCGATGCGGGATAA
```

A codon-optimized nucleotide sequence encoding a truncated collagen
type 21 polypeptide from *Gallus gallus*

SEQ ID NO: 30

```
GATACTGGTTTCCCGGGGATGCCTGGGCGCTCAGGTGATCCGGGGCGTAGTGGAAAAGACGGTCTGC

CGGGGTCCCCGGGCTTTAAGGGTGAGGTGGGTCAGCCCGGTAGTCCAGGTTTAGAAGGTCACCGCGG

AGAGCCCGGGATTCCAGGCATTCCTGGCAACCAGGGTGCCAAGGGACAGAAAGGCGAAATTGGTCCG

CCCGGCCTACCGGGCGCGAAAGGTTCTCCTGGTGAAACCGGTCTCATGGGTCCGGAAGGTAGCTTCG

GCCTGCCCGGCGCACCTGGTCCGAAGGGCGATAAGGGGGAGCCTGGGCTGCAAGGTAAACCGGGTAG

TTCTGGCGCCAAAGGTGAACCCGGCGGTCCCGGTGCGCCAGGGGAACCAGGTTATCCTGGTATTCCT

GGAACCCAAGGAATTAAAGGTGACAAAGGCTCACAGGGCGAAAGTGGTATACAGGGTCGCAAGGGCG

AAAAAGGACGTCAGGGCAATCCAGGCCTGCAGGGTACTGAAGGCCTGCGTGGAGAACAGGGTGAGAA

AGGTGAAAAAGGAGATCCTGGTATTCGC
```

In some embodiments, the non-naturally occurring polypeptide comprises an amino acid sequence of any one of SEQ ID NOs: 2, 4, 6, and 8. In some embodiments, the non-naturally occurring polypeptide comprises an amino acid sequence having a sequence identity of at least 80%, at least 85%, at least 90%, at least 95%, or at least 98% thereof, or the like, to the amino acid sequence of any one of SEQ ID NOs: 2, 4, 6, and 8. Alternatively and/or additionally, the non-naturally occurring polypeptide is encoded by a nucleic acid sequence of any one of SEQ ID NOs: 1, 3, 5, 7, and 25-30. In some embodiments, the non-naturally occurring polypeptide is encoded by a nucleic acid having sequence identity of at least 65%, at least 70%, at least 75%, at least 80%, at least 85%, at least 90%, at least 95%, or at least 98% thereof, or the like, to the nucleic acid sequence of any one of SEQ ID NOs: 1, 3, 5, 7, and 25-30.

Figure 6:
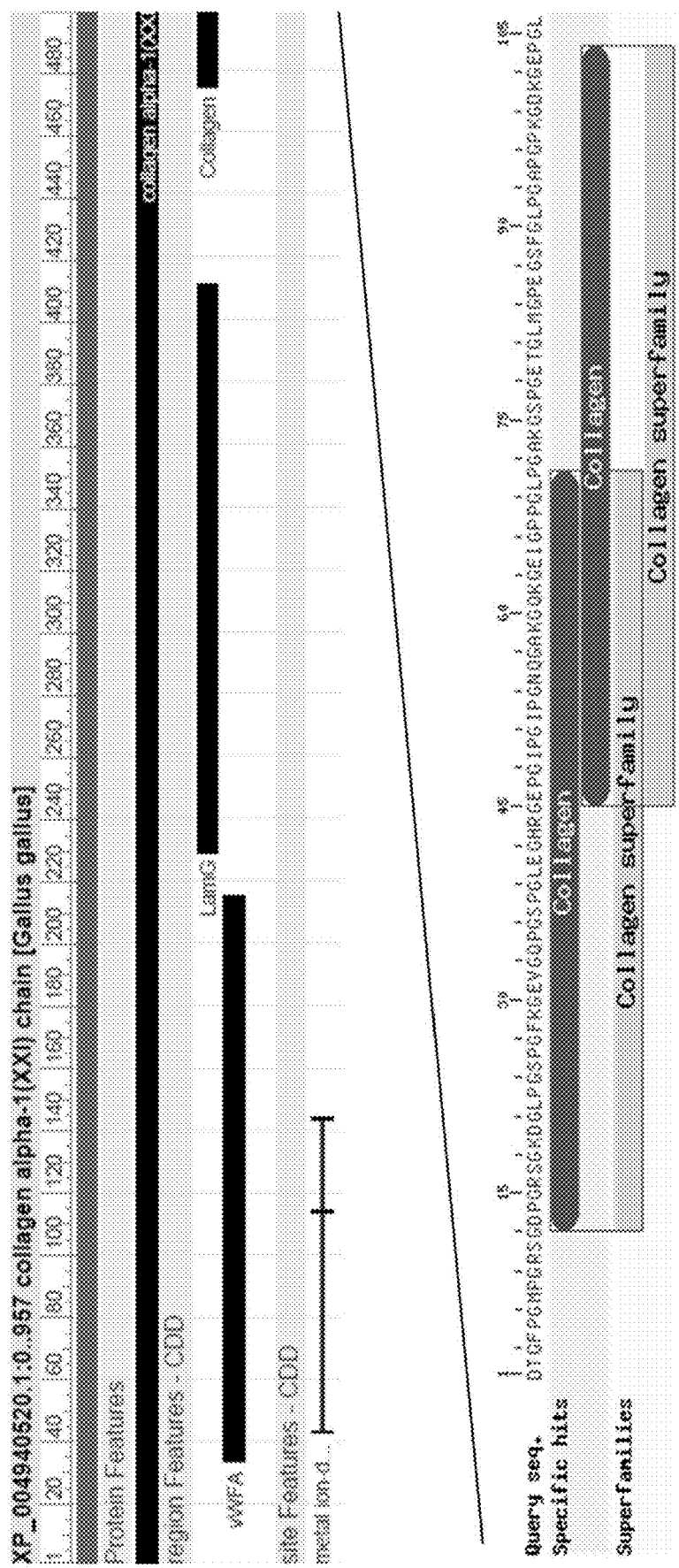
FIG. 6 depicts alignments of non-naturally occurring polypeptides of the disclosure with corresponding naturally occurring collagens.
Figure 6:
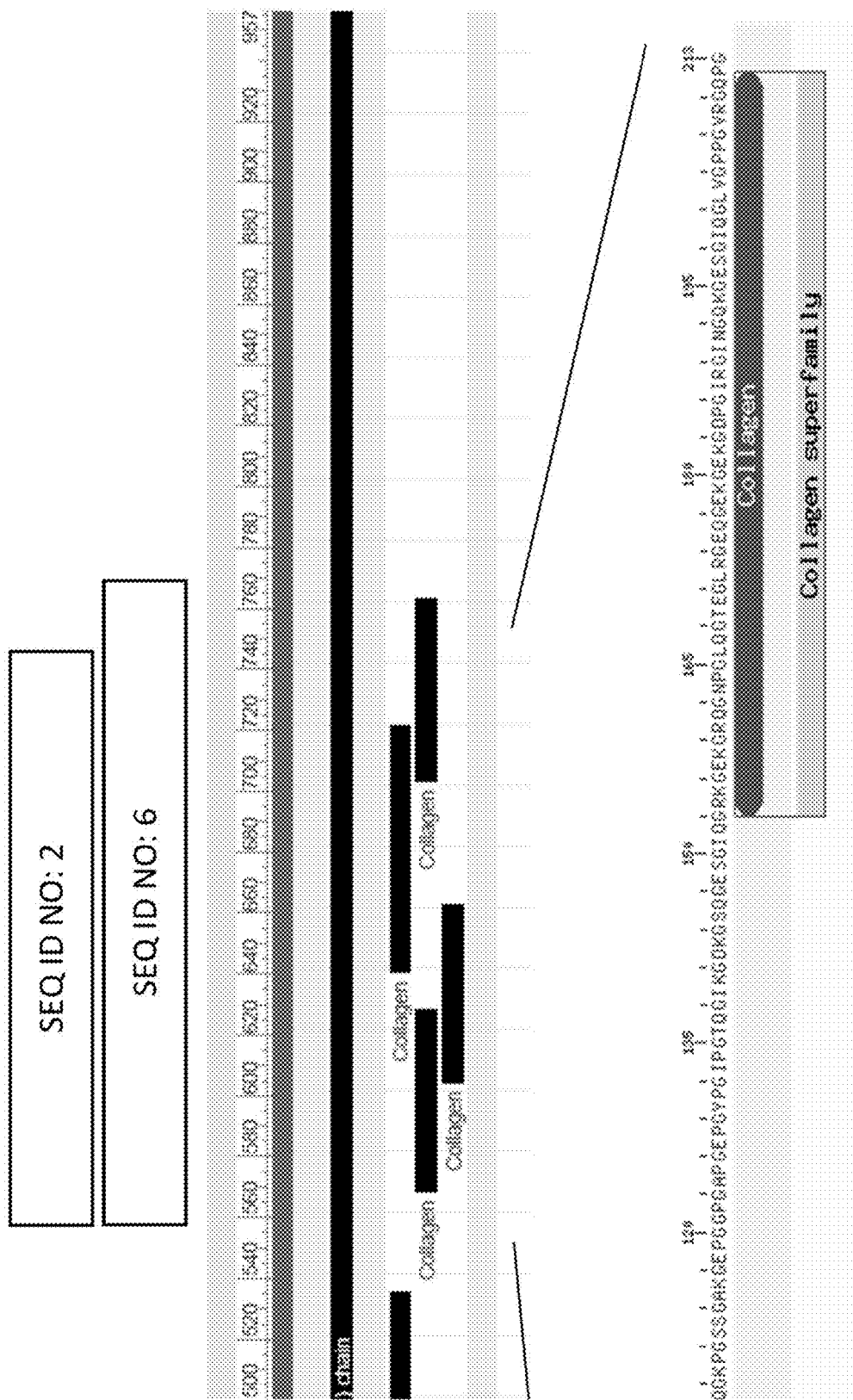
Figure 6:
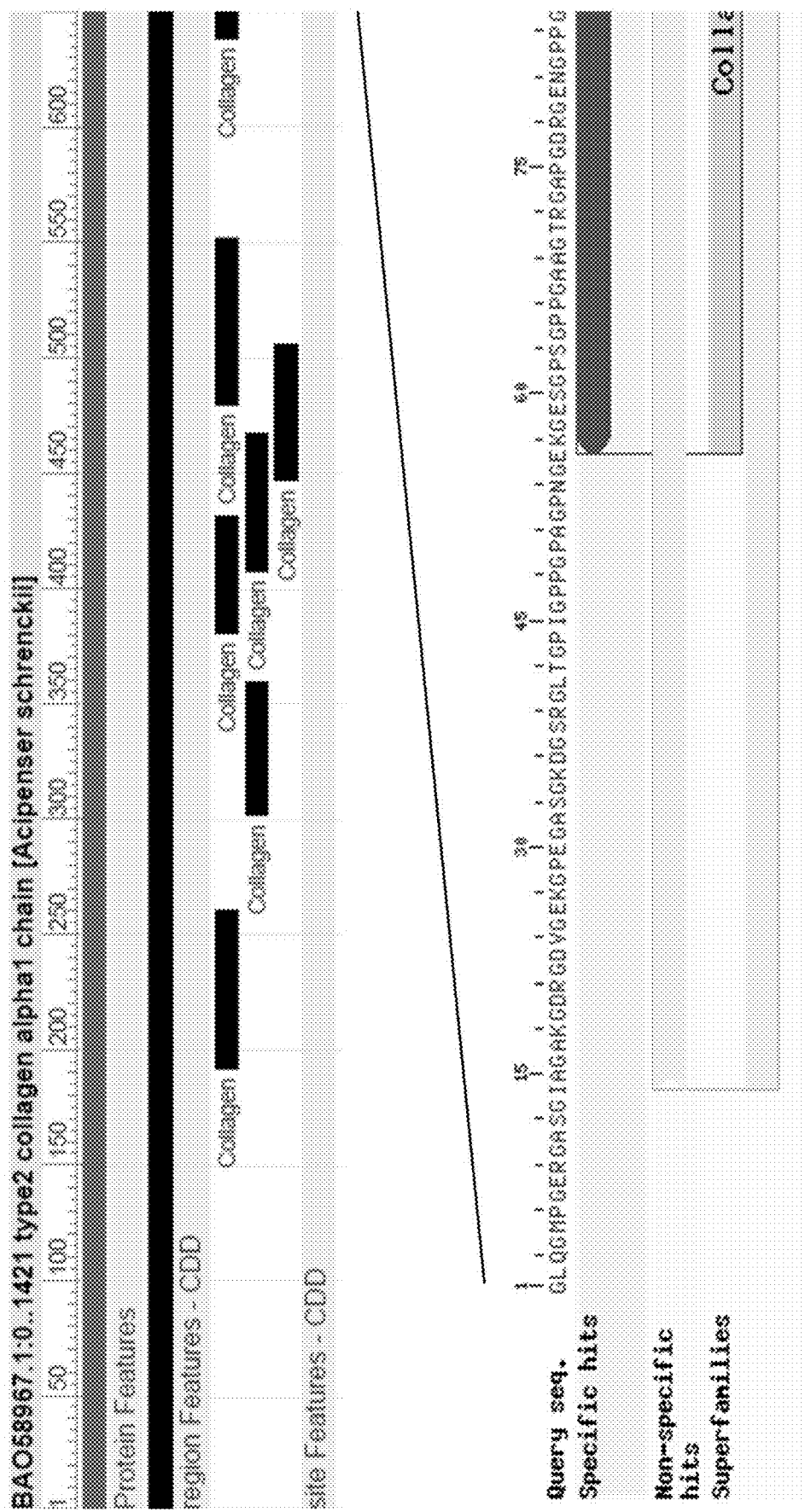
Figure 6:
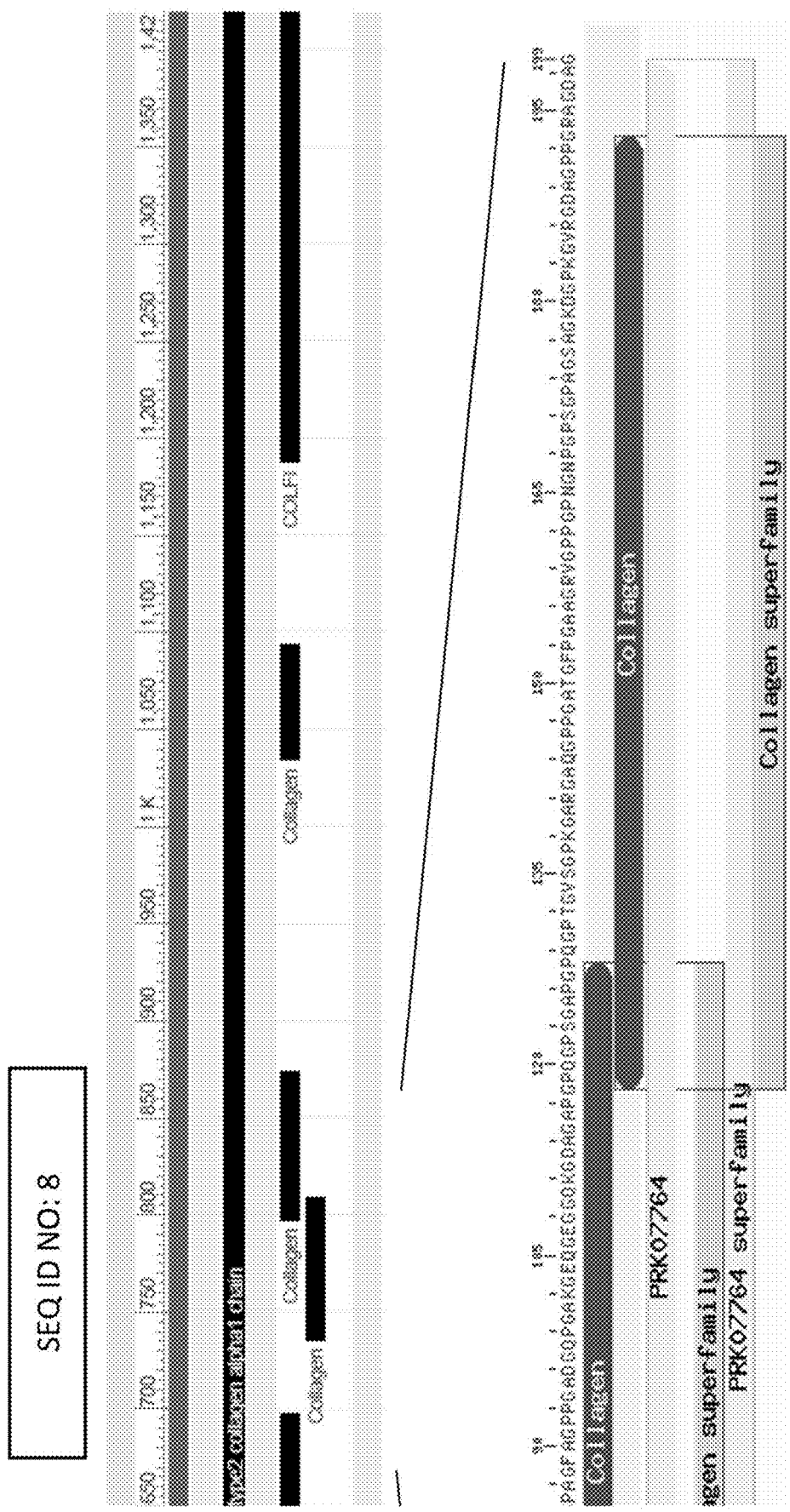

In some aspects, the non-naturally occurring polypeptides provided herein may or may not contain one or more domains from natural collagen. FIG. 6 depicts an alignment of exemplary non-naturally occurring polypeptides (e.g., truncated collagens) of the disclosure with the corresponding naturally occurring collagen. The top panel depicts an alignment of a non-naturally occurring polypeptide of SEQ ID NO: 2 and SEQ ID NO: 6 with *Gallus gallus* type 21 alpha 1 collagen (e.g., SEQ ID NO: 31). The bottom panel depicts an alignment of a non-naturally occurring polypeptide of SEQ ID NO: 8 with *Acipenser schrenckii* type 2 alpha 1 collagen. FIG. 6 demonstrates that non-naturally occurring polypeptides may have one or more domains found in natural collagen (e.g., collagen triple helix repeat domains). FIG. 6 further demonstrates that non-naturally occurring polypeptides may lack one or more domains found in natural collagen (e.g., Von Willebrand factor type A (vWA) domain, laminin G domain, fibrillar collagen C-terminal domain). In some aspects, a non-naturally occurring polypeptide provided herein may contain one or more collagen triple helix repeat domains. In some aspects, a non-naturally occurring polypeptide provided herein may lack one or more of a Von Willebrand factor type A (vWA) domain, a laminin G domain, and a fibrillar collagen C-terminal domain).

In some embodiments, the non-naturally occurring polypeptide (e.g., recombinant polypeptide) includes a secretion signal sequence. Any suitable secretion signal sequence (e.g., hydrophobic signaling peptides, Sec signal peptides, Tat signal peptides, etc.) that can induce the non-naturally occurring polypeptide (e.g., recombinant polypeptide) to be secreted to the periplasmic and/or extracellular space (e.g., when produced in a recombinant host cell). Exemplary secretion signal sequences includes a peptide having an amino acid sequence of any one of SEQ ID NOs: 10, 12, 14, 16, 18, 20, 22, and 24. Alternatively and/or additionally, the secretion signal sequence includes a peptide encoded by a nucleic acid sequence of any one of SEQ ID NOs: 9, 11, 13, 15, 17, 19, 21, and 23. The secretion signal sequence is preferably located in the N-terminus of the non-naturally occurring polypeptide (e.g., recombinant polypeptide). Yet, it is contemplated that the secretion signal sequence can be located at other than N-terminus where the secretion signal sequence remains functional.

The non-naturally occurring polypeptide (e.g., recombinant polypeptide) as described herein can be expressed or generated via a nucleic acid sequence encoding the non-naturally occurring polypeptide (e.g., recombinant polypeptide). Thus, another aspect of the disclosure includes an expression vector comprising a nucleic acid sequence encoding the non-naturally occurring polypeptide (e.g., recombinant polypeptide). In some embodiments, the expression vector is a bacterial expression vector. In some embodiments, the expression vector is a yeast expression vector. In some embodiments, the expression vector is an insect expression vector. Any suitable expression vector that can induce the protein expression from the inserted nucleic acid encoding the non-naturally occurring polypeptide (e.g., recombinant polypeptide). Exemplary bacterial expression vectors may include pGEX vectors where glutathione S-transferase is used as a fusion partner and gene expression is under the control of the tac promoter, or pET vectors (e.g., pET28 vector, etc.) which uses a T7 promoter. Exemplary yeast expression vectors may include pPIC vectors, which uses the AOX1 promoter inducible with methanol. In some embodiments, the expression vector is in a plasmid form (e.g., including bacterial artificial chromosome form, etc.) that are independently present in the host cell (e.g., cells expressing the recombinant polypeptide). In some embodiments, the expression vector is stably integrated into the chromosome of the host cell via random or targeted integration.

In some embodiments, the nucleic acid sequence encoding the non-naturally occurring polypeptide (e.g., recombinant polypeptide) is codon-optimized to be expressed in non-animal cells, preferably in bacterial cells. As used herein, "codon-optimized" means that the codon composition is improved for expression in the heterologous cells (e.g., microbial cells, bacterial cells, etc.) without altering the encoded amino acid sequences. Non-limiting examples of codon-optimized nucleic acid sequences (e.g., encoding a non-naturally occurring polypeptide as described herein) include SEQ ID NOs: 25-30.

In some embodiments, the expression vector may include one or more selection agent. The selection agents include certain sugars including galactose containing sugars or antibiotics including ampicillin, hygromycin, G418 and others. Enzymes that are used to confer resistance to the selection agent include β-galactosidase or a β-lactamase. Alternatively and/or additionally, the expression vector includes an inducible promoter or a constitutive promoter (e.g., CMV promoter, etc.) such that the nucleic acid encoding the recombinant protein is operatively linked to the inducible promoter or the constitutive promoter. For example, the expression vector may include tetracycline-inducible promoter pTET, araC-ParaBAD inducible promoter, or IPTG inducible lac promoter. As used herein, "operatively linked" promoter and nucleic acid means that the expression of the nucleic acid (e.g., transcription, translation, etc.) is at least under partial control of the promoter.

In some embodiments, the nucleic acid encoding the non-naturally occurring polypeptide (e.g., recombinant polypeptide) (e.g., a nucleic acid of any one of SEQ ID NOs: 1, 3, 5, 7, and 25-30), and the expression vector may have an overlap of from 20 to 50 bp long, from 20 to 40 bp long, from 20 to 30 bp long, or from 30 to 40 bp long. Such overlap can be added using PCR with a DNA polymerase (e.g., PRIMESTAR® GXL polymerase (www.takarabio-.com/products/per/gc-rich-per/primestar-gxl-dna-polymerase)). Opened expression vector and the insert nucleic acid encoding the non-naturally occurring polypeptide (e.g., recombinant polypeptide) can be assembled together into the final plasmid using any suitable cloning system (e.g., IN-FUSION® Cloning (www.takarabio.com/products/cloning/in-fusion-cloning) or SGI Gib son assembly (us.vwr.com/store/product/17613857/gibson-assembly-hifi-1-step-kit-synthetic-genomics-inc)).

Such prepared expression vector (or plasmid) can be used to generate genetically engineered or modified organisms, or a recombinant cell to produce the non-naturally occurring polypeptides described herein (e.g., collagens, truncated collagens, or collagen fragments). Preferably, the recombinant cells contain at least one copy of a plasmid or a stably integrated heterologous nucleic acid sequence encoding the non-naturally occurring polypeptide (e.g., collagens, truncated collagens, or collagen fragments, preferably collagens, truncated collagens, or collagen fragments of, or derived from, *Gallus gallus* collagen and/or *Acipenser schrenckii* collagen). In some embodiments, the recombinant cell is a microbial cell. For example, where the expression vector is bacterial expression vector, the expression vector can be inserted into (e.g., via any suitable transformation method) the bacterial cells for protein expression (e.g., *Escherichia coli* including BL-21 cells, etc.) to be independently present in the cytoplasm of the bacteria (e.g., as a plasmid form) or to be at least temporarily and/or stably integrated into the bacterial chromosome.

Consequently, the transformed cells can be cultivated in a suitable media. Preferably, the suitable media includes a minimal media and the cells are frozen in 1.5 aliquots with vegetable glycerin at a ratio of 50:50 of cells of cells to glycerin. For protein expression, one vial of the frozen cultured cells can be cultured in a suitable amount of bacteria culture media (e.g., minimal media, 50 ml, 100 ml, etc.) for at least 6 hours, at least 8 hours, at least 10 hours, at least 12 hours, at least overnight at at least 36° C., preferably at about 37° C. by continuously shaking the culture (e.g., at least 100 rpm, at least 200 rpm, at least 250 rpm, etc.). Table 2 and Table 3 show the exemplary formulation of the minimal media that can be used for cell cultivation and culture.

TABLE 2

Minimal Media Formulation

| | |
|---|---|
| 1) Autoclave 5 L of 550 g/kg Glucose syrup at concentration in DI water. (VWR, product #97061-170). | |
| 2) Autoclave in 3946 mL of DI water and add | 20 g (NH$_4$)$_2$HPO$_4$. (VWR, product #97061-932). |
| | 66.5 g KH$_2$PO$_4$. (VWR, product #97062-348). |
| | 22.5 g H$_3$C$_6$H$_5$O$_7$. (VWR, product #BDH9228-2.5 KG). |
| | 8.85 g MgSO$_4$.7H$_2$O. (VWR, product #97062-134). |
| | 10 mL of 1000x Trace metals formulation |
| After autoclaving, add: | |
| 118 g of (1) to (2) | |
| 5 mL of 25 mg/mL Kanamycin Sulfate (VWR-V0408) | |
| Use 28% NH$_4$OH (VWR, product #BDH3022) to adjust pH to 6.1. | |

TABLE 3

Trace metals formulation

| | |
|---|---|
| Ferrous Sulfate Heptahydrate | 27.8 g/L (Spectrum, 7782-63-0) |
| Zinc Sulfate heptahydrate | 2.88 g/L (Spectrum, 7446-20-0) |
| Calcium chloride dihydrate | 2.94 g/L (Spectrum, 2971347) |
| Sodium molybdate dihydrate | 0.48 g/L (Spectrum, 10102-40-6) |
| Manganese chloride tetrahydrate | 1.26 g/L (Spectrum, 13446-34-9) |
| Sodium selenite | 0.35 g/L (Spectrum, 10102-18-8) |
| Boric acid | 0.12 g/L (Spectrum, 10043-35-3) |

In some embodiments, transformed cells can then be transferred to a larger volume of growth media (e.g., minimal media) and grown for at least 4 hours, at least 5 hours, at least 6 hours, at least 7 hours, at least 8 hours, from 5 to 10 hours, from 5 to 9 hours, from 6 to 9 hours, and/or alternatively until the cell density in the media reaches optical density (OD) of 600.

Additionally, fermentation process can be performed at various temperature ranging from 22° C. to 33° C., from 29° C. to 33° C., from 30° C. to 32° C., from 23° C. to 29° C., or from 25° C. to 28° C. In some embodiments, the temperature of the fermentation can be maintained at a constant temperature and immediately upon completion of fermentation the non-naturally occurring polypeptide can be purified. Alternatively, the temperature of the fermentations can be maintained for a desired period of time and when cell densities of OD600 of 10-20 are reached, then the temperature can be reduced to induce protein production. In such embodiments, typically, the temperature is reduced from 28° C. to 25° C. During the fermentation, protein expression in the bacteria can be induced by adding induction reagent. For example, where the expression vector contains lac promoter and the nucleic acid encoding the non-naturally occurring polypeptide (e.g., truncated collagen, collagen fragments, or collagen) is under the control of the lac promoter, the expression of the nucleic acid can be induced by adding isopropyl β-d-1-thiogalactopyranoside (IPTG) at a concentration ranging from 0.1-1.5 mM, from 0.1-1.0 mM, or from 0.1-0.5 mM. Fermentation can be continued for 20-24 hours, or in some embodiments, for 40-60 hours.

It is contemplated that such generated recombinant cells (e.g., recombinant bacteria transformed with the expression vector) intracellularly express the non-naturally occurring polypeptides (e.g., truncated collagen, collagen fragments, or collagen) encoded by the nucleic acids in the expression vector. Such intracellularly expressed polypeptides (e.g., truncated collagen, collagen fragments, or collagen) can then be secreted (via a secretion signal sequence) to the extracellular space (e.g., into a culture media). Thus, in some embodiments, the culture media can contain secreted recombinant protein (e.g., truncated collagen, collagen fragments, or collagen) encoded by the nucleic acids.

Thus, another aspect of the disclosure includes a composition including the non-naturally occurring polypeptide (e.g., recombinant collagen, truncated collagen, collagen fragments, or collagen) encoded by the nucleic acids. In some embodiments, the composition may include the recombinant cell comprising an integrated heterologous nucleic acid sequence encoding a non-naturally occurring polypeptide (e.g., collagen, a truncated collagen, or fragment thereof), and/or the culture medium (e.g., growth media, cultivation media, etc.) for the recombinant cell.

Alternatively and/or additionally, the composition may include purified recombinant proteins from the recombinant cells and/or the culture medium. In some embodiments, the recombinant proteins are purified from the culture medium where the recombinant cells grow and secrete the recombinant proteins thereto. In some embodiments, the recombinant protein is coupled with a tag (e.g., histidine tag, etc) such that the recombinant protein can be purified using affinity purification is known as immobilized metal affinity chromatography (IMAC). Alternatively, the recombinant protein can be purified via column chromatography. For example, the recombinant protein can be purified by acid treatment of homogenized growth media. In such example, the pH of the growth media (e.g., fermentation broth) can be decreased to from 3 to 3.5 using 5-50% sulfuric Acid. The recombinant cells are then separated using centrifugation. Supernatant of the acidified broth can be tested on a polyacrylamide gel and determined whether it contains the recombinant protein in relatively high abundance compared to starting pellet. The recombinant protein slurry obtained is generally high in salts. To obtain volume and salt reduction, concentration and diafiltration steps can be performed using filtration steps. For example, the filtration step can be performed using EMD Millipore Tangential Flow Filtration system with ultrafiltration cassettes of 0.1 m² each. Total area of filtration in this example can be 0.2 m² using two cassettes in parallel. A volume reduction of 5× and a salt reduction of 19× can be achieved in the TFF stage. Final collagen slurry can be run on an SDS-PAGE gel to confirm presence of the recombinant protein. The purified recombinant protein can then be analyzed on an SDS-PAGE gel to identify a corresponding thick and clear band observed at the expected sizes for each respective protein. Quantification of titers and purity can be further conducted using reverse phase and size exclusion HPLC chromatography. It is preferred that the purity of the purified recombinant proteins is at least at least 80%, at least 85%, at least 90%, at least 95%, or at least 99%.

In some embodiments, the composition including the non-naturally occurring polypeptides provided herein (e.g., recombinant proteins and/or purified recombinant proteins) can be formulated for consumption by an individual (e.g., a human, a patient, a person, an animal, etc.). In some embodiments, the non-naturally occurring polypeptides (e.g., recombinant proteins and/or purified recombinant proteins) can be formulated for oral consumption as nutraceutical supplements. In some embodiments, the non-naturally occurring polypeptides (e.g., recombinant proteins and/or purified recombinant proteins) can be formulated for oral consumption as a food product or a food ingredient. In some embodiments, the non-naturally occurring polypeptides can be formulated as a protein supplement. Optionally, in such embodiments, the non-naturally occurring polypeptides (e.g., recombinant proteins and/or purified recombinant proteins) can be mixed with at least one of a carrier molecule, a preservative, and/or additional edible ingredients. Thus, for example, the composition may include vitamins (e.g. vitamin A, vitamin B, vitamin C, vitamin D, vitamin E, etc.), minerals (e.g., calcium, zinc, copper, manganese, chromium, molundenum, boron, etc), sugar (e.g., cellulose, dextrose, maltose, etc.), and/or natural extracts (e.g., herb, *ginseng*, *echinacea*, green tea, glucosamine, omega-3, lutein, folic acid, liver oil, fish oil, coffee extracts, etc.). Formulations suitable for consumption by an individual (e.g., a human) include, without limitation, ready-to-mix powders, ready-to-drink beverages, functional shots, supplement tablets and capsules, coffee creamers, bars, bites or baked goods, "no bone" broth, non-dairy frozen novelty, gummies (e.g., candy), chocolates, and meat snacks. Non-limiting examples of formulations containing the non-naturally occurring polypeptides are provided in Examples 4-6.

A composition, formulation, or product is "nutritional" or "nutritive" if it provides an appreciable amount of nourishment to its intended consumer, meaning the consumer assimilates all or a portion of the composition or formulation into a cell, organ, and/or tissue. Generally, such assimilation into a cell, organ, and/or tissue provides a benefit or utility to the consumer, e.g., by maintaining or improving the health and/or natural function(s) of said cell, organ, and/or tissue. A nutritional composition or formulation that is assimilated as described herein is termed "nutrition". By way of non-limiting example, a polypeptide is nutritional if it provides an appreciable amount of polypeptide nourishment to its intended consumer, meaning the consumer assimilates all or a portion of the protein, typically in the form of single amino acids or small peptides, into a cell, organ, and/or tissue. "Nutrition" also means the process of providing to a subject, such as a human or other mammal, a nutritional composition, formulation, product, or other material. A nutritional product need not be "nutritionally complete", meaning if consumed in sufficient quantity, the product provides all carbohydrates, lipids, essential fatty acids, essential amino acids, conditionally essential amino acids, vitamins, and minerals required for health of the consumer. Additionally, a "nutritionally complete protein" contains all protein nutrition required (meaning the amount required for physiological normalcy by the organism) but does not necessarily contain micronutrients such as vitamins and minerals, carbohydrates, or lipids.

In preferred embodiments, a composition or formulation is nutritional in its provision of polypeptide capable of decomposition (e.g., the breaking of a peptide bond, often termed protein digestion) to single amino acids and/or small peptides (e.g., two amino acids, three amino acids, or four amino acids, possibly up to ten amino acids) in an amount sufficient to provide a "nutritional benefit". In addition, in certain embodiments provided are nutritional polypeptides that transit across the gastrointestinal wall and are absorbed into the bloodstream as small peptides (e.g., larger than single amino acids but smaller than about ten amino acids) or larger peptides, oligopeptides, or polypeptides (e.g., >11 amino acids). A nutritional benefit in a polypeptide-containing composition can be demonstrated and, optionally, quantified, by a number of metrics. For example, a nutritional benefit is the benefit to a consuming organism equivalent to or greater than at least about 0.5% of a reference daily intake value of protein, such as about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 60%, about 65%, about 70%, about 75%, about 80%, about 85%, about 90%, about 95%, about 100% or greater than about 100% of a reference daily intake value. Alternatively, a nutritional benefit is demonstrated by the feeling and/or recognition of satiety by the consumer. In other embodiments, a nutritional benefit is demonstrated by incorporation of a substantial amount of the polypeptide component of the composition or formulation into the cells, organs, and/or tissues of the consumer, such incorporation generally meaning that single amino acids or short peptides are used to produce polypeptides de novo intracellularly. A "consumer" or a "consuming organism" means any animal capable of ingesting the product having the nutritional benefit. Typically, the consumer is a mammal such as a healthy human, e.g., a healthy infant, child, adult, or older adult. Alternatively, the consumer is a mammal such as a human (e.g., an infant, child, adult, or older adult) at risk of developing or suffering from a disease, disorder, or condition characterized by (i) the lack of adequate nutrition and/or (ii) the alleviation thereof by the nutritional products of the present disclosure. An "infant" is generally a human under about age 1 or 2, a "child" is generally a human under about age 18, and an "older adult" or "elderly" human is a human aged about 65 or older.

Herein provided are nutritive polypeptides (e.g., non-naturally occurring polypeptides described herein) capable of transforming health and treating, preventing and reducing the severity of a multitude of diseases, disorders, and conditions associated with amino acid pathophysiology, as they are selected for specific physiologic benefits to improve health and address many nutrition-related conditions, including gastrointestinal malabsorption, muscle wasting, diabetes or pre-diabetes, obesity, oncology, metabolic diseases, and other cellular and systemic diseases. Also provided are the compositions and formulations that contain the nutritive polypeptides (e.g., non-naturally occurring polypeptides described herein), as food, beverages, medical foods, supplements, and pharmaceuticals.

Nutritive polypeptides (e.g., non-naturally occurring polypeptides described herein) can be evaluated for their physicochemical and functional properties can be evaluated (see, e.g., Example 7). Such properties may include digestibility, allergenicity, thermostability, solubility, aggregation, toxicity, taste, and mouth/feel characteristics.

In some embodiments, the formulations are incorporated into food products having advantages over similar food products lacking the nutritive polypeptides (e.g., non-naturally occurring polypeptides described herein), or the formulations are incorporated into other products such as beverage products or animal feed products. For example, the food products have a reduced fat content, a reduced sugar content, and/or a reduced calorie content compared to a food product not having the nutritive polypeptide (e.g., non-naturally occurring polypeptides described herein). Preferably, the nutritive polypeptide (e.g., non-naturally occurring polypeptides described herein) is present in the food product such that consumption of a nutritional amount of the food product is satiating. In an embodiment, gelatin, an animal-derived material, is replaced by a non-animal derived product, containing one or more nutritive polypeptides (e.g., non-naturally occurring polypeptides described herein). Typically the nutritive polypeptide (e.g., non-naturally occurring polypeptides described herein) is present in an amount effective to replace gelatin in the product. The gelatin replacement is incorporated into a food product, a beverage product, or an animal feed product, and the formulation is substantially free of non-comestible products.

Also provided herein are formulations containing a nutritive polypeptide (e.g., non-naturally occurring polypeptides described herein) present in a functional and/or nutritional amount, which increases the viscosity of a food or beverage product, such as formulations containing viscosity-increasing nutritive polypeptides (e.g., non-naturally occurring polypeptides described herein) incorporated into food products having advantages over similar food products lacking the nutritive polypeptides (e.g., non-naturally occurring polypeptides described herein). For example, the food products have a reduced fat content, a reduced sugar content, and/or a reduced calorie content compared to a food product not having the nutritive polypeptide (e.g., non-naturally occurring polypeptides described herein). Viscous nutritive polypeptides (e.g., non-naturally occurring polypeptides described herein) can be used as a nutritionally favorable low calorie substitute for fat. Additionally, it may be desired to add to the compositions and products one or more polysaccharides or emulsifiers, resulting in a further improvement in the creamy mouthfeel.

In certain embodiments, the non-naturally occurring polypeptides of the disclosure may be combined with other ingredients to provide combination products. Such ingredients may include carbohydrates, lipids, supplemental minerals, supplemental vitamins, excipients or buffering agents, flavoring agents, sweeteners, or coloring agents.

A "carbohydrate" refers to a sugar or polymer of sugars. The terms "saccharide", "polysaccharide," "carbohydrate", and "oligosaccharide" can be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

As used herein a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In some embodiments the composition comprises at least one modified lipid, for example a lipid that has been modified by cooking.

Additional ingredients also include supplemental minerals or mineral sources. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

Additional ingredients also include one or more supplemental vitamins. The vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

The formulations may also include excipients or buffering agents. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, a coloring agent. Non-limiting examples of suitable buffering agents include sodium citrate, magnesium carbonate, magnesium bicarbonate, calcium carbonate, and calcium bicarbonate.

The formulations may also include a preservative. Non-limiting examples of suitable preservatives include organic acids that are naturally derived from fermentation (such as citric, ascorbic, propionic acids), antimicrobial peptides (nisin) or other suitable preservatives (such as salt, calcium sorbate, sodium sorbate).

Binding agents, lubricants, dispersion enhancers, disintegrants and the like may also be used as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments the disintegrant is an effervescent disintegrant. Non-limiting examples of suitable effervescent disintegrants include sodium bicarbonate in combination with citric acid, and sodium bicarbonate in combination with tartaric acid.

Additional ingredients may also include flavoring agents, sweeteners, or coloring agents. Flavoring agents incorporated into the outer layer can be chosen from synthetic flavor oils and flavoring aromatics; natural oils; extracts from plants, leaves, flowers, and fruits; and combinations thereof. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Non-limiting examples of suitable color agents include food, drug and cosmetic colors (FD&C), drug and cosmetic colors (D&C), and external drug and cosmetic colors (Ext. D&C).

Solid dosage forms for oral administration include capsules, tablets, caplets, pills, troches, lozenges, powders, and granules. A capsule typically comprises a core material comprising a protein or composition and a shell wall that encapsulates the core material. In some embodiments, the core material comprises at least one of a solid, a liquid, and an emulsion. In some embodiments, the shell wall material comprises at least one of a soft gelatin, a hard gelatin, and a polymer.

Powders or granules embodying the polypeptides and compositions disclosed herein can be incorporated into a food product. In some embodiments the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula, and so forth. Other suitable means for oral administration include aqueous and nonaqueous solutions, creams, pastes, emulsions, suspensions and slurries, each of which may optionally also contain at least one of suitable solvents, preservatives, emulsifying agents, suspending agents, diluents, sweeteners, coloring agents, a tastant, a flavorant, and flavoring agents.

Suitable examples of a solid foodstuff include without limitation a food bar, a snack bar, a cookie, a brownie, a muffin, a cracker, a biscuit, a cream or paste, an ice cream bar, a frozen yogurt bar, and the like.

A formulation can contain a nutritive polypeptide (e.g., non-naturally occurring polypeptides as described herein) in an amount based on the concentration of the nutritive polypeptide (e.g., non-naturally occurring polypeptides as described herein) (e.g., on a weight-to-weight basis), such that the nutritive polypeptide (e.g., non-naturally occurring polypeptides as described herein) accounts for up to 100% of the weight of the formulation, meaning that all or essentially all of the matter present in the formulation is in the form of the nutritive polypeptide (e.g., non-naturally occurring polypeptides as described herein). More typically, about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5% or less than about 5% of the weight present in the formulation is in the form of the nutritive polypeptide (e.g., non-naturally occurring polypeptides as described herein). In some embodiments, the formulation contains 10 mg, 100 mg, 500 mg, 750 mg, 1 g, 2 g, 3 g, 4 g, 5 g, 6 g, 7 g, 8 g, 9, 10 g, 15 g, 20 g, 25 g, 30 g, 35 g, 40 g, 45 g, 50 g, 60 g, 70 g, 80 g, 90 g, 100 g, or over 100 g of nutritive polypeptide.

In some embodiments, the polypeptides or compositions are provided in a dosage form. In some embodiments, the dosage form is designed for administration of at least one polypeptide disclosed herein, wherein the total amount of polypeptide administered is selected from 0.1 g to 1 g, 1 g to 5 g, from 2 g to 10 g, from 5 g to 15 g, from 10 g to 20 g, from 15 g to 25 g, from 20 g to 40 g, from 25 g to 50 g, and from 30 g to 60 g. In some embodiments, the dosage form is designed for administration of at least one protein disclosed herein, wherein the total amount of protein administered is selected from about 0.1 g, 0.1 g to 1 g, 1 g, 2 g, 3 g, 4 g, 5 g, 6 g, 7 g, 8 g, 9 g, 10 g, 15 g, 20 g, 25 g, 30 g, 35 g, 40 g, 45 g, 50 g, 55 g, 60 g, 65 g, 70 g, 75 g, 80 g, 85 g, 90 g, 95 g, and 100 g.

In some embodiments the protein or composition is consumed at a rate of from 0.1 g to 1 g a day, 1 g to 5 g a day, from 2 g to 10 g a day, from 5 g to 15 g a day, from 10 g to 20 g a day, from 15 g to 30 g a day, from 20 g to 40 g a day, from 25 g to 50 g a day, from 40 g to 80 g a day, from 50 g to 100 g a day, or more.

In another aspect, this disclosure provides methods of maintaining or increasing at least one of muscle mass, muscle strength, and functional performance in a subject. In some embodiments, the methods comprise providing to the subject a sufficient amount of a polypeptide of this disclosure, a composition of this disclosure, or a composition made by a method of this disclosure. In some embodiments, the subject is at least one of elderly, critically-medically ill, and suffering from protein-energy malnutrition. In some embodiments, the sufficient amount of a polypeptide of this disclosure, a composition of this disclosure, or a composition made by a method of this disclosure is consumed by the subject in coordination with performance of exercise. In some embodiments, the polypeptide of this disclosure, composition of this disclosure, or composition made by a method of this disclosure is consumed by the subject by an oral, enteral, or parenteral route. In some embodiments, the polypeptide of this disclosure, composition of this disclosure, or composition made by a method of this disclosure is consumed by the subject by an oral route. In some embodiments, the polypeptide of this disclosure, composition of this disclosure, or composition made by a method of this disclosure is consumed by the subject by an enteral route.

In another aspect, this disclosure provides methods of maintaining or achieving a desirable body mass index in a subject. In some embodiments, the methods comprise providing to the subject a sufficient amount of a polypeptide of this disclosure, a composition of this disclosure, or a composition made by a method of this disclosure. In some embodiments, the subject is at least one of elderly, critically-medically ill, and suffering from protein-energy malnutrition. In some embodiments, the sufficient amount of a polypeptide of this disclosure, a composition of this disclosure, or a composition made by a method of this disclosure is consumed by the subject in coordination with performance of exercise. In some embodiments, the polypeptide of this disclosure, composition of this disclosure, or composition made by a method of this disclosure is consumed by the subject by an oral, enteral, or parenteral route.

In another aspect, this disclosure provides methods of providing a polypeptide (e.g., of the disclosure) to a subject with protein-energy malnutrition. In some embodiments, the methods comprise providing to the subject a sufficient amount of a polypeptide of this disclosure, a composition of this disclosure, or a composition made by a method of this disclosure. In some embodiments, the polypeptide of this disclosure, composition of this disclosure, or composition made by a method of this disclosure is consumed by the subject by an oral, enteral, or parenteral route.

The polypeptides of this disclosure are useful for treating sarcopenia or frailty once it develops in a subject or for preventing the onset of sarcopenia or frailty in a subject who is a member of an at risk groups. In some embodiments, all of the polypeptide consumed by the subject is a polypeptide according to this disclosure. In some embodiments, polypeptides according to this disclosure are combined with other sources of protein and/or free amino acids to provide the total protein intake of the subject. In some embodiments, the subject is at least one of elderly, critically-medically ill, and suffering from protein-energy malnutrition. In some embodiments, the polypeptide according to disclosure, the composition according to disclosure, or the composition made by a method according to disclosure is consumed by the subject in coordination with performance of exercise. In some embodiments, the polypeptide according to this disclosure, the composition according to disclosure, or the composition made by a method according to disclosure is consumed by the subject by an oral, enteral, or parenteral route.

In some embodiments, incorporating at least one polypeptide or composition of this disclosure into the diet of a subject has at least one effect selected from inducing postprandial satiety (including by suppressing hunger), inducing thermogenesis, reducing glycemic response, positively affecting energy expenditure positively affecting lean body mass, reducing the weight gain caused by overeating, and decreasing energy intake. In some embodiments, incorporating at least one polypeptide or composition of this disclosure into the diet of a subject has at least one effect selected from increasing loss of body fat, reducing lean tissue loss, improving lipid profile, and improving glucose tolerance and insulin sensitivity in the subject.

In some embodiments, the composition including the non-naturally occurring polypeptides (e.g., recombinant proteins and/or purified recombinant proteins) can be formulated for topical application. The topical application can be for medical purpose or cosmetic purpose. In such embodiments, the composition may further include at least one of a carrier molecule (e.g., vehicle), a preservative, and/or additional edible ingredients. Any suitable carrier molecules are contemplated, and the exemplary carrier molecule may include water, oil, alcohol, propylene glycol, or emulsifiers. In addition, any suitable preservatives are contemplated, and the exemplary preservatives include zinc oxide, parabens, formaldehyde releasers, isothiazolinones, phenoxyethanol, or organic acids such as benzoic acid, sodium benzoate, or butylene glycol, hexanediol, or potassium sorbate.

In one aspect, the compositions that comprise non-naturally occurring polypeptides may be personal care products (e.g., a cosmetic). In some embodiments, the compositions are formulated for topical administration. The compositions can contain other cosmetic ingredients suitable for human use. The personal care products may be useful for preventing or treating ultraviolet radiation damage to human skin or hair. The personal care products may be useful for increasing the firmness, elasticity, brightness, hydration, tactile texture or visual texture of skin and/or stimulate collagen production. The personal care products may be useful for reducing redness of the skin. The personal care products may be applied to skin or hair. The compositions include, for example, masks, skin cleaners such as soap, cleansing creams, cleansing lotions, facial cleansers, cleansing milks, cleansing pads, facial washes, facial and body creams and moisturizers, facial serums, facial and body masks, facial toners and mists, eye creams and eye treatments, exfoliator formulas, lip balms and lipsticks, hair shampoo, hair conditioner and body shampoos, hair and scalp serums, hair mists and sprays, eye shadow, concealer, mascara and other color cosmetics.

The compositions that comprise the non-naturally occurring polypeptide can further comprise at least one additional ingredient comprising a topical carrier or a preservative. The topical carrier may comprise a topical carrier selected from the group consisting of liposome, biodegradable microcapsule, lotion, spray, aerosol, dusting powder, biodegradable polymer, mineral oil, triglyceride oil, silicone oil, glycerin, glycerin monostearate, alcohols, emulsifying agents, liquid petroleum, white petrolatum, propylene glycol, polyoxyethylene, polyoxypropylene, wax, sorbitan monostearate, polysorbate, cetyl ester wax, cetearyl alcohol, 2-octyldodecanol, benzyl alcohol, cyclomethicone, cyclopentasiloxane and water. The preservative may comprise a preservative selected from the group consisting of tocopherol, diiodomethyl-p-tolylsulfone, 2-Bromo-2-nitropropane-1,3-diol, cis isomer 1-(3-chloroallyl)-3,5,7-triaza-1-azoniaadamantane chloride, glutaraldehyde, 4,4-dimethyl oxazolidine, 7-Ethylbicyclooxazolidine, phenoxyethanol, butylene glycol, 1,2 Hexanediol, methyl paraben, sorbic acid, Germaben® II, rosemary extract, and EDTA Also provided in certain embodiments herein, are methods of decreasing skin damage, promoting the repair of damaged skin, protecting skin against UV damage, and/or protecting skin cells against the effects of exposure to urban dust. In another embodiment, methods of increasing the firmness, elasticity, brightness, hydration, tactile texture, or visual texture of skin and/or stimulating collagen production are provided. The methods may comprise a step of applying a composition comprising a non-naturally occurring polypeptide of the disclosure to the skin of a subject. Without being bound to a particular theory or mechanism, the non-naturally occurring polypeptide in the composition may decrease skin damage by protecting against UV damage. In some cases, the non-naturally occurring polypeptide in the composition may promote the repair of damaged skin by increasing the viability of cells. In some cases, the non-naturally occurring polypeptide in the composition may decrease skin damage and/or promote repair of cells by increasing procollagen synthesis when applied to skin, and/or promoting the viability of skin cells. In some cases, the non-naturally occurring polypeptide decreases the formation of thymine-thymine (TT) dimer formation.

The methods provided herein encompass the use of a composition for treatment indicated in the method, such as by the steps provided herein. In embodiments, the disclosure provides the use of a composition provided herein (e.g., a non-naturally occurring polypeptide or a formulation comprising a non-naturally occurring polypeptide) in a method for decreasing skin damage, promoting the repair of damaged skin, protecting skin against UV damage, and/or protecting skin cells against the effects of exposure to urban dust (e.g., such as by administering to the skin of a subject a composition provided herein). In embodiments, the disclosure provides the use of a composition provided herein (e.g., a non-naturally occurring polypeptide or a formulation comprising a non-naturally occurring polypeptide) in a method for increasing the firmness, elasticity, brightness, hydration, tactile texture, or visual texture of skin and/or stimulating collagen production.

Provided in certain embodiments herein are (e.g., topical) compositions or formulations comprising one or more non-naturally occurring polypeptide provided herein (e.g., for cosmetic use). In some embodiments, the composition provides any suitable amount of polypeptide provided herein, such as in any suitable amount (e.g., an amount suitable to provide a benefit when given or administered to an individual or cell). In some specific embodiments, the composition comprises an amount suitable to provide a beneficial effect to the skin of an individual when (e.g., topically) administered to the skin of the individual. In specific embodiments, the composition comprises between 0.001% and 30% w/w of a polypeptide (or non-naturally occurring collagen polypeptide) such as provided herein. In more specific embodiments, the composition comprises between 0.001% and 20% w/w of a polypeptide (or non-naturally occurring collagen polypeptide) such as provided herein, between 0.001% and 10% w/w of a polypeptide (or non-naturally occurring collagen polypeptide) such as provided herein, between 0.001% and 5% w/w of a polypeptide (or non-naturally occurring collagen polypeptide) such as provided herein, between 0.001% and 2% w/w of a polypeptide (or non-naturally occurring collagen polypeptide) such as provided herein, between 0.001% and 1% w/w of a polypeptide (or non-naturally occurring collagen polypeptide) such as provided herein, between 0.001% and 0.5% w/w of a polypeptide (or non-naturally occurring collagen polypeptide) such as provided herein, and between 0.001% and 0.2% w/w of a polypeptide (or non-naturally occurring collagen polypeptide) such as provided herein.

In various embodiments, the concentration or amount of a non-naturally occurring polypeptide (e.g., recombinant protein) provided herein is in a composition provided herein in any suitable amount and may, e.g., vary depending on the use or formulation (e.g., gel, capsule, liquid, powder, etc.). Exemplary concentrations of the non-naturally occurring polypeptides (e.g., recombinant proteins) in the composition can be at least about 0.01%, at least about 0.05%, at least about 0.1%, at least about 0.2%, at least about 0.5%, at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98% (w/v or w/w) in the composition. Alternatively and/or additionally, the exemplary concentration of the non-naturally occurring polypeptides (e.g., recombinant proteins) in the composition can be about 0.01%, about 0.05%, about 0.1%, about 0.2%, at least 0.5%, 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 98% (w/v or w/w) in the composition. Alternatively and/or additionally, the exemplary concentration of the non-naturally occurring polypeptides (e.g., recombinant proteins) in the composition can range from about 0.01% to about 99%, from about 0.05% to about 99%, from about 0.1% to about 99%, from about 0.1% to about 99%, from about 0.5% to about 99%, from about 0.1% to about 10%, from about 1% to about 99%, from about 5% to about 99%, from about 10% to about 99%, from about 15% to about 99%, from about 20% to about 99%, from about 25% to about 99%, from about 30% to about 99%, from about 35% to about 99%, from about 40% to about 99%, from about 45% to about 99%, from about 50% to about 99%, from about 55% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99%, from about 0.1% to about 90%, from about 1% to about 90%, from about 5% to about 90%, from about 10% to about 90%, from about 15% to about 90%, from about 20% to about 90%, from about 25% to about 90%, from about 30% to about 90%, from about 35% to about 90%, from about 40% to about 90%, from about 45% to about 90%, from about 50% to about 90%, from about 55% to about 90%, from about 60% to about 90%, from about 65% to about 90%, from about 70% to about 90%, from about 75% to about 90%, from about 80% to about 90%, from about 85% to about 90%, from about 20% to about 80%, from about 25% to about 80%, from about 30% to about 80%, from about 35% to about 80%, from about 40% to about 80%, from about 45% to about 80%, from about 50% to about 80%, from about 55% to about 80%, from about 60% to about 80%, from about 65% to about 80%, from about 70% to about 80%, from about 75% to about 80%, from about 70% to about 99%, from about 75% to about 99%, from about 80% to about 99%, etc. Alternatively and/or additionally, the exemplary concentration of the non-naturally occurring polypeptides (e.g., recombinant proteins) in the composition can be less than about 95%, about 90%, about 85%, about 80%, about 75%, about 70%, about 65%, about 60%, about 55%, about 50%, about 45%, about 40%, etc.

Certain aspects of the disclosure include methods of improving the appearance of the skin, the hair, and/or the nails of a subject by administering the composition to the subject. Additionally and/or alternatively, the disclosure includes a method of improving the joint health and/or restoring bone density in a subject. In some embodiments, the subject has or is suspected to have osteoporosis and/or osteoarthritis. Alternatively and/or additionally, the disclosure includes a method of improving gut health, altering or improving the microbiome of a subject, or altering and/or reducing inflammation or tissue repair in a subject. In some embodiments, the composition is administered orally in a dose and schedule sufficient or effective for improving the appearance of the skin, the hair, and/or the nails of a subject, improving the joint health and/or restoring bone density in a subject having osteoporosis and/or osteoarthritis, and/or improving gut health, altering or improving the microbiome of a subject, or altering and/or reducing inflammation or tissue repair in a subject. Any suitable dose is optionally used. In some embodiments, the dose used is from about 0.1 mg/kg to about 200 mg/kg, from about 0.2 mg/kg to about 150 mg/kg, from about 0.5 mg/kg to about 150 mg/kg, from about 0.5 mg/kg to about 100 mg/kg, from about 0.8 mg/kg to about 100 mg/kg, from about 1.0 mg/kg to about 100 mg/kg, from about 1.0 mg/kg to about 90 mg/kg, from about 1.0 mg/kg to about 80 mg/kg, from about 1.0 mg/kg to about 70 mg/kg, from about 1.0 mg/kg to about 60 mg/kg, from about 1.0 mg/kg to about 50 mg/kg, about 0.5 mg/kg, about 1 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, or about 5.0 mg/kg, about 10 mg/kg, about 15 mg/kg, about 20 mg/kg, about 25 mg/kg, or about 30 mg/kg. In some embodiments, the dose may increase or decrease by the schedule of the administration. For example, the dose for administering to a subject (e.g., human) can be increased or decreased for about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 1.0 mg/kg per each administration (e.g., for 3 consecutive administration, the dose can be increased from 2.0 mg/kg, 2.2 mg/kg, 2.4 mg/kg, respectively, etc.). In another example, the dose for administering to a subject (e.g., human) can be increased and then decreased, or decreased and then increased for about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 1.0 mg/kg per each administration (e.g., for 5 consecutive administration, the dose can be increased from 2.0 mg/kg, 2.2 mg/kg, 2.4 mg/kg, then 2.2 mg/kg, and 2.0 mg/kg, respectively, etc.).

In some embodiments, the schedule of administration varies depending on the purpose, gender, age, or health condition of the subject. For example, in some embodiments, the composition is administered once a day, twice a day, three times a day, up to 6 times a day, every 2 days, every 3 days, every 4 days, every 5 days, every 6 days, etc. Alternatively and/or additionally, in some embodiments, the composition is administered a plurality of times in an irregular interval, or increased interval, or decreased interval.

In certain embodiments, the composition is topically applied in a dose and/or schedule sufficient or effective for improving the appearance of the skin, the hair, and/or the nails of a subject, and/or reducing inflammation in a subject. In some instances, the dose varies depending on the target area for the topical application (e.g., hair, skin, wound, nail, etc.), and can range from about 0.1 g/inch$^2$ to about 10 g/inch$^2$, from about 0.1 g/inch$^2$ to about 9 g/inch$^2$, from about 0.1 g/inch$^2$ to about 8 g/inch$^2$, from about 0.1 g/inch$^2$ to about 7 g/inch$^2$, from about 0.1 g/inch$^2$ to about 6 g/inch$^2$, from about 0.1 g/inch$^2$ to about 5 g/inch$^2$, from about 0.1 g/inch$^2$ to about 4 g/inch$^2$, from about 0.1 g/inch$^2$ to about 3 g/inch$^2$, from about 0.5 g/inch$^2$ to about 5 g/inch$^2$, from about 0.5 g/inch$^2$ to about 4 g/inch$^2$, from about 1 g/inch$^2$ to about 4 g/inch$^2$, or from about 1 g/inch$^2$ to about 3 g/inch$^2$, of area for topical application. In certain embodiments, the dose varies depending on the purpose, gender, age, severity of damage on the area, or health condition. For example, the composition can be applied to the target area of the subject at least three times a day, at least twice a day, once a day, up to 6 times a day, every 2 days, every 3 days, every 4 days, every 5 days, every 6 days, etc.

Skin appearance and quality: In some embodiments, provided herein are methods of improving skin appearance and/or quality, such as by administering an effective amount of a product or composition (e.g., containing a non-naturally occurring polypeptide described herein) provided herein to an individual (e.g., an individual in need of such improvement). In some embodiments, administration is orally or topically. In some instances, administration results in various changes or effects on the skin of the individual. In some instances, the skin of the individual demonstrates increased proliferation and/or reduced cell death rate (e.g., when tested using a colorimetric assay for assessing cell metabolic activity (e.g., MTT assay)). In some embodiments, the skin demonstrates improved production of extracellular matrix (ECM) components such as collagen, elastin, fibronectin, fibrillin and/or decreased production of matrix-degrading proteins (e.g., matrix metalloproteinases (MMPs) and proteases). In certain instances, the skin shows resistance or improved outcome upon exposure to harmful agents like photodamage (e.g., UV irradiation), pollution (e.g., urban dust), and/or harsh skincare actives (e.g., retinoic acid, benzoyl peroxide, salicylic acid). In certain instances, such resistance or improved outcome is shown via improved cell viability or proliferation (or reduced cell death) that can be assessed using MTT viability assay, via improved DNA repair that can be assessed by thymidine-dimer ELISA detection, reduced inflammation that can be assessed by Luminex detection, reduced reactive oxidative stress (ROS) that can be assessed by CM-H$_2$DCFDA (General oxidative stress indicator) detection.

In some instances, the skin demonstrates reduction in wrinkles and/or fine lines, reduction in skin redness and/or hyperpigmentation, increase in skin brightness, decrease in pore size, decrease in skin roughness, and/or reduction in acne (e.g., when assessed using CLARITY analysis). In certain instances, the skin demonstrates improvement in skin elasticity, increase in skin firmness, increase in skin hydration, increase in skin barrier function, increase in skin collagen and elastin content, and/or increase in dermal density.

Hair Quality: In some embodiments, provided herein are methods of improving hair appearance and/or quality, such as by administering an effective amount of a product or composition provided herein (e.g., containing a non-naturally occurring polypeptide as described herein) to an individual (e.g., an individual in need of such improvement). In some embodiments, administration is orally or topically. In some instances, administration results in various changes or effects on the hair of the individual. In certain instances, the hair demonstrates improved hair fiber thickness and/or density, increases in moisture, faster growth rate, reduced split ends, reduced frizz/increased static control, improved fiber alignment/shine, increased combability, and/or stronger resistance to hair breakage. In some instances, the hair demonstrates improved hair growth, thicker hair fiber diameter, increased combability, reduced hair loss, and/or increased hair tensile strength.

Nail Quality: In some embodiments, provided herein are methods of improving nail appearance and/or quality, such as by administering an effective amount of a product or composition provided herein (e.g., containing a non-naturally occurring polypeptide as described herein) to an individual (e.g., an individual in need of such improvement). In some embodiments, administration is orally or topically. In some instances, administration results in various changes or effects on the nail of the individual. In certain instances, the nail demonstrates improved (reductions in) nail peeling, nail edge irregularities and/or nail roughness, frequency of cracked/chipped nails, and/or increases in nail growth rate.

Joint health: In some embodiments, provided herein are methods of improving joint health, such as by administering an effective amount of a product or composition provided herein (e.g., containing a non-naturally occurring polypeptide as described herein) to an individual (e.g., an individual in need of such improvement). In some embodiments, administration is orally. In some instances, administration results in various changes or effects in joint health of the individual. In certain instances, the improved joint health is demonstrated by reduction in reported joint pain and/or increase in range of joint mobility.

Inflammation: In some embodiments, provided herein are methods of improving inflammatory effects, such as by administering an effective amount of a product or composition provided herein (e.g., containing a non-naturally occurring polypeptide as described herein) to an individual (e.g., an individual in need of such improvement). In some embodiments, administration is orally or topically. In some instances, administration results in various changes or effects in inflammation in the individual. In certain instances, the improved inflammatory effect is demonstrated by lower cytokine levels in the bloodstream (e.g., assessed by Luminex detection) and/or restore healthy levels of immune cells (e.g., by blood differential counts).

Gut health: In some embodiments, provided herein are methods of improving gut health, such as by administering an effective amount of a product or composition provided herein (e.g., containing a non-naturally occurring polypeptide as described herein) to an individual (e.g., an individual in need of such improvement). In some embodiments, administration is orally. In some instances, administration results in various changes or effects in gut health of the individual. In certain instances, the improved gut health is demonstrated by improved bowel movements and/or decrease in gastrointestinal discomfort/pain.

Microbiome: In some embodiments, provided herein are methods of altering and/or improving the microbiome, such as by administering an effective amount of a product or composition provided herein (e.g., containing a non-naturally occurring polypeptide as described herein) to an individual (e.g., an individual in need of such improvement). In some embodiments, administration is orally. In some instances, administration results in various changes or effects in the microbiome of the individual. In certain instances, the improved microbiome is demonstrated by increased diversity of microbes and/or increased abundance of beneficial microbes (e.g., assessed by 16S DNA sequencing stool samples).

EXAMPLES

Example 1. Generation of Non-Naturally Occurring Polypeptides of the Disclosure

This example shows the generation of a recombinant polypeptide of the disclosure by genetically engineered microorganisms and purification process of such generated polypeptides.

The polynucleotides of SEQ ID NOs: 1, 3, 5, and 7 were synthesized and at least one of the polynucleotides were inserted into a pET vector. Overlaps between a pET vector and SEQ ID NOs: 1, 3, 5, and 7 were designed to be between 20 and 30 bp long and added using PCR with the enzyme PRIMESTAR® GXL polymerase (www.takarabio.com/products/per/gc-rich-per/primestar-gxl-dna-polymerase).

The opened pET vector and insert DNA (e.g., polynucleotide of SEQ ID NO: 1) were assembled together into the final plasmid using IN-FUSION® Cloning (www.takarabio.com/products/cloning/in-fusion-cloning). In all cases, the nucleic acid sequences were preceded by a secretion signal sequence disclosed as SEQ ID NOs: 9, 11, 13, 15, 17, 19, 21, or 23. Plasmid sequences were verified through Sanger sequencing.

Cells were transformed with final plasmids and subsequently cultivated in minimal media and frozen in 1.5 aliquots with vegetable glycerin at a ratio of 50:50 of cells to glycerin. One vial of this frozen culture was revived in 50 ml of minimal media overnight at 37° C., 200 rpm. Formulations of the minimal media in this example are shown in Table 2 and Table 3. Cells were then transferred into 300 ml of minimal media and grown for 6-9 hours to reach an optical density (OD) 600 of 5-10.

The fermentations were performed at various temperature ranging from 25° to 28° C. For some fermentations, the temperature of the fermentation was maintained at a constant temperature and immediately upon completion of fermentation the polypeptide was purified. For other fermentations, the temperature of the fermentations was maintained for a desired period of time and when cell densities of OD600 of 10-20 were reached, the temperature was reduced to induce protein production. Typically, the temperature was reduced from 28° C. to 25° C. Induction was carried out by adding IPTG to the media at concentrations ranging from 0.1-0.5 mM. Fermentations were continued for 40-60 hours.

The recombinant polypeptide was purified as follows: The pH of the fermentation broth was decreased to between 3-3.5 using 5-50% Sulfuric Acid. The cells were then separated using centrifugation or centrifugation followed by microfiltration. Supernatant of the acidified broth was tested on a polyacrylamide gel and found to contain recombinant polypeptide in relatively high abundance compared to starting pellet. To obtain volume and salt reduction, concentration and diafiltration steps were performed ultrafiltration. Final polypeptide slurry was run on an SDS-PAGE gel to confirm presence of the recombinant polypeptide.

To verify that the desired proteins were produced, supernatants from cultures of microbes carrying SEQ ID NOs: 1, 3, 5, or 7 were collected and purified by decreasing their pH as described above. The acidified broth was analyzed by SDS-PAGE, and bands corresponding to the expected size protein were detected in relative purity. As shown in FIG. 1, a thick and clear band was observed at the expected sizes for each respective protein. Samples were subsequently analyzed for quantifying recombinant polypeptide titers and purity by reverse phase and size exclusion HPLC chromatography and mass spectrometry, which confirmed the correct identity of the respective proteins of interest.

Figure 2A:
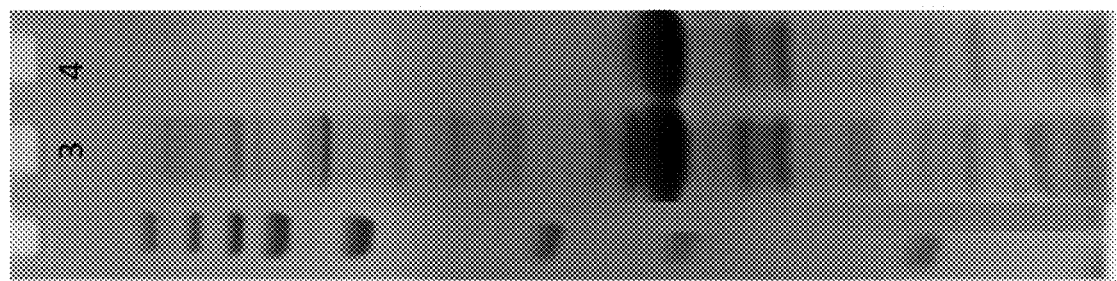
FIGS. 2A-2C depict images of SDS-PAGE gels showing bands of non-naturally occurring polypeptides of the disclosure before and after pH 3.0 treatment.
Figure 2B:
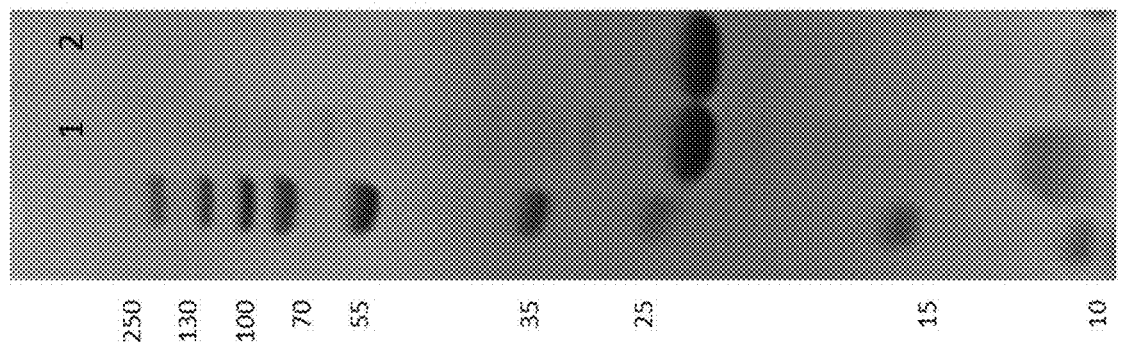
Figure 2C:
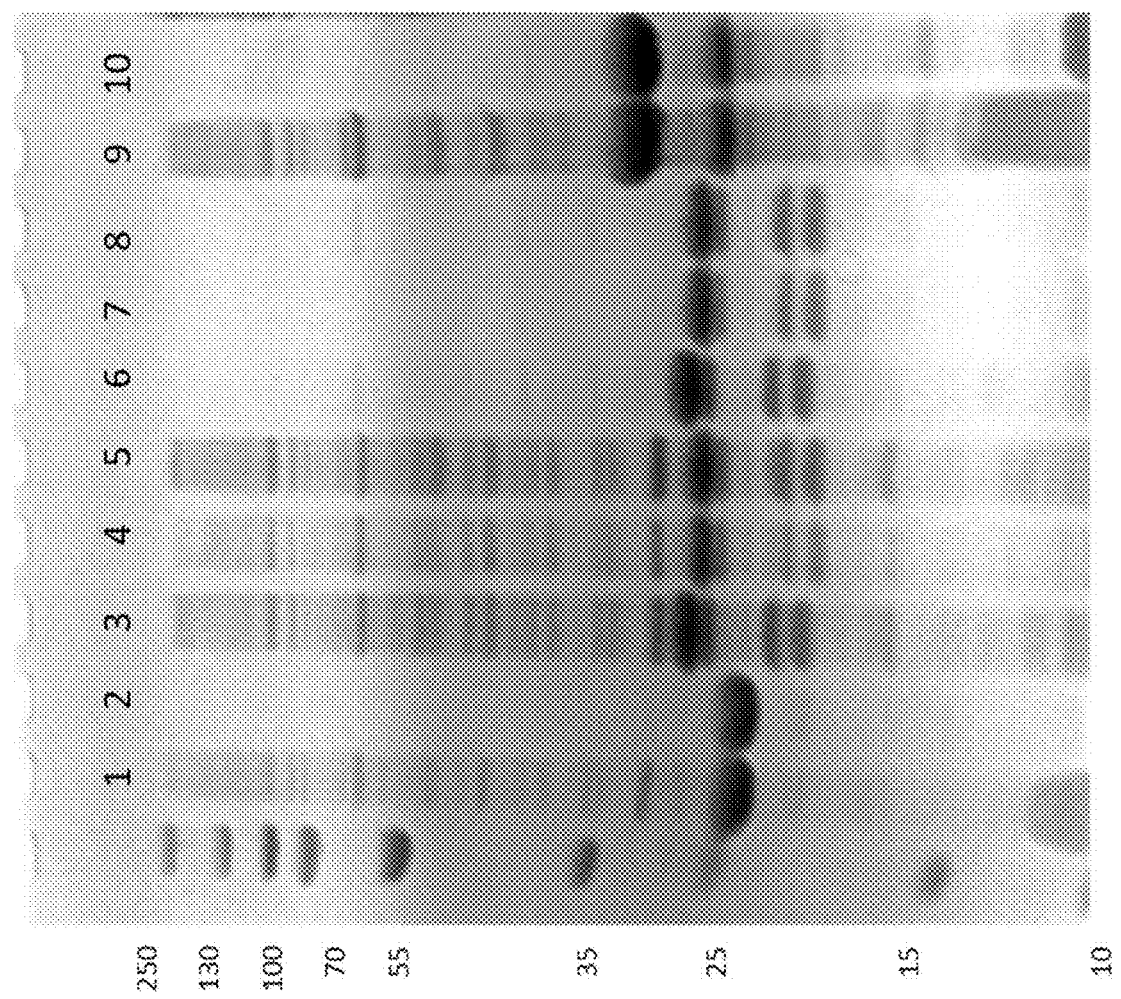

FIGS. 2A-2C depict SDS-PAGE gels of non-naturally occurring polypeptides of the disclosure before and after treatment at pH 3.0. FIG. 2A depicts an SDS-PAGE gel of fermentation supernatant containing a non-naturally occurring polypeptide having an amino acid sequence of SEQ ID NO: 2 before (Lane 1) and after (Lane 2) treatment at pH 3.0. The expected molecular weight of such polypeptide was about 17.9 kDa. The identity of the polypeptide was confirmed by mass spectrometry (data not shown). FIG. 2B depicts an SDS-PAGE gel of fermentation supernatant containing a non-naturally occurring polypeptide having an amino acid sequence of SEQ ID NO: 8 before (Lane 3) and after (Lane 4) treatment at pH 3.0. The expected molecular weight of such polypeptide was about 17.6 kDa. The identity of the polypeptide was confirmed by mass spectrometry (data not shown). FIG. 2C depicts an SDS-PAGE gel of fermentation supernatant containing a non-naturally occurring polypeptide produced in various bacterial host strains having an amino acid sequence of SEQ ID NO: 8 before (Lanes 3-5) and after (Lanes 6-8) treatment at pH 3.0.

Example 2. Human Clinical Study of the Non-Naturally Occurring Polypeptides of the Disclosure Skin appearance and quality: Patients are recruited and/or cultured human skin cells or patient-derived skin samples are provided to evaluate the benefit of recombinant polypeptides provided herein. Non-naturally occurring polypeptides as described herein (or products containing non-naturally occurring polypeptides as described herein) and control products are administered (orally or topically) to separate (in vitro or in vivo) cohorts to evaluate for various effects on skin. Skin effects are evaluated quantitatively and/or qualitatively. For example, when the composition including the non-naturally occurring polypeptide is applied to or administered to, the cultured human skin cells in vitro (either primary culture or cell line), or human skin tissue ex vivo, the cultured human skin cells or cells in the human skin tissue show increased proliferation or reduced cell death rate (e.g., when tested using a colorimetric assay for assessing cell metabolic activity (e.g., MTT assay)). In some instances, such cultured human skin cells or cells in the human skin tissue contacted or treated with the compositions including the non-naturally occurring polypeptides described herein may show, via RNA-seq transcriptomic analysis or proteomics analysis, increased production of extracellular matrix (ECM) components such as collagen, elastin, fibronectin, fibrillin, and decreased production of matrix-degrading proteins (e.g., matrix metalloproteinases (MMPs) and proteases). Such treated cultured human skin cells or cells in the human skin tissue are evaluated to demonstrate resistance or improved outcome upon exposure to harmful agents like photodamage (e.g., UV irradiation), pollution (e.g., urban dust), and harsh skincare actives (e.g., retinoic acid, benzoyl peroxide, salicylic acid). Such resistance or improved outcome is shown via improved cell viability or proliferation (or reduced cell death) that is assessed using MTT viability assay, via improved DNA repair that is assessed by thymidine-dimer ELISA detection, reduced inflammation that is assessed by Luminex detection, and/or reduced reactive oxidative stress (ROS) that is assessed by CM-H2DCFDA (General oxidative stress indicator) detection.

In another example, when the composition including a non-naturally occurring polypeptide (e.g., as described herein) is applied to, or administered to the subject orally or topically on the skin, the subject's skin is evaluated for reduction in wrinkles and fine lines, reduction in skin redness and hyperpigmentation, increase in skin brightness, decrease in pore size, decrease in skin roughness, and reduction in acne (e.g., when assessed using CLARITY analysis). The skin is also further evaluated (before and after administration) to show change in skin elasticity, change in skin firmness, change in skin hydration, change in skin barrier function, change in skin collagen and elastin content, and/or change in dermal density.

Hair Quality: Effects of products (e.g., containing a non-naturally occurring polypeptide as described herein) provided herein (e.g., relative to control products) on hair are also evaluated. For example, when the products provided herein (e.g., containing a non-naturally occurring polypeptide as described herein) are applied to hair or orally administered to a subject, hair quality is measured, such as by measuring changes in hair fiber thickness and density, changes in moisture, changes in growth rate, changes in prevalence of split ends, changes in frizz/increased static control, changes in fiber alignment/shine, changes in combability, and/or changes in resistance to hair breakage (e.g., measured by in vitro hair tress testing). In some instances, clinical testing measures changes in hair growth, hair fiber diameter, combability, hair loss, and/or hair tensile strength.

Nail Quality: Effects of products (e.g., containing a non-naturally occurring polypeptide as described herein) provided herein (e.g., relative to control products) on nails are also evaluated. For example, when the products provided herein (e.g., containing a non-naturally occurring polypeptide as described herein) are applied to nail or orally administered to a subject, nail quality is measured, such as by measuring changes in nail hardness, nail peeling, nail edge irregularities and nail roughness, frequency of cracked/chipped nails, and/or nail growth rate.

Joint health: Effects of products (e.g., containing a non-naturally occurring polypeptide as described herein) provided herein (e.g., relative to control products) on joints are also evaluated. For example, when the products provided herein (e.g., containing a non-naturally occurring polypeptide as described herein) are orally administered to a subject, joint quality is measured, such as by measuring changes in reported joint pain and/or range of joint mobility.

Inflammation: Effects of products (e.g., containing a non-naturally occurring polypeptide as described herein) provided herein (e.g., relative to control products) on inflammation are also evaluated. For example, when the products provided herein (e.g., containing a non-naturally occurring polypeptide as described herein) are orally administered to a subject, changes in inflammation are measured, cytokine levels in the bloodstream are measured (e.g., assessed by Luminex detection), and/or levels of immune cells are measured (by blood differential counts).

Gut health: Effects of products (e.g., containing a non-naturally occurring polypeptide as described herein) provided herein (e.g., relative to control products) in gut health are also evaluated. For example, when the products provided herein (e.g., containing a non-naturally occurring polypeptide as described herein) are orally administered to a subject, changes in bowel movements and/or gastrointestinal discomfort/pain are measured.

Microbiome: Effects of products (e.g., containing a non-naturally occurring polypeptide described herein) provided herein (e.g., relative to control products) in the microbiome are also evaluated. For example, when the products provided herein (e.g., containing a non-naturally occurring polypeptide described herein) are orally administered to a subject, changes in diversity of microbes or abundance of beneficial microbes is measured, which can be assessed by 16S DNA sequencing stool samples. Also, such effect can be shown in vitro as the composition supports growth of beneficial microbes in broth co-cultures.

Example 3. In Vitro Studies of Non-Naturally Occurring Polypeptides of the Disclosure This example demonstrates functional effects on cells in vitro after treatment with a non-naturally occurring polypeptide having the amino acid sequence of SEQ ID NO: 2.

A Non-Naturally Occurring Polypeptide of SEQ ID NO: 2 Increases Viability of Human Dermal Fibroblasts.

Figure 3:
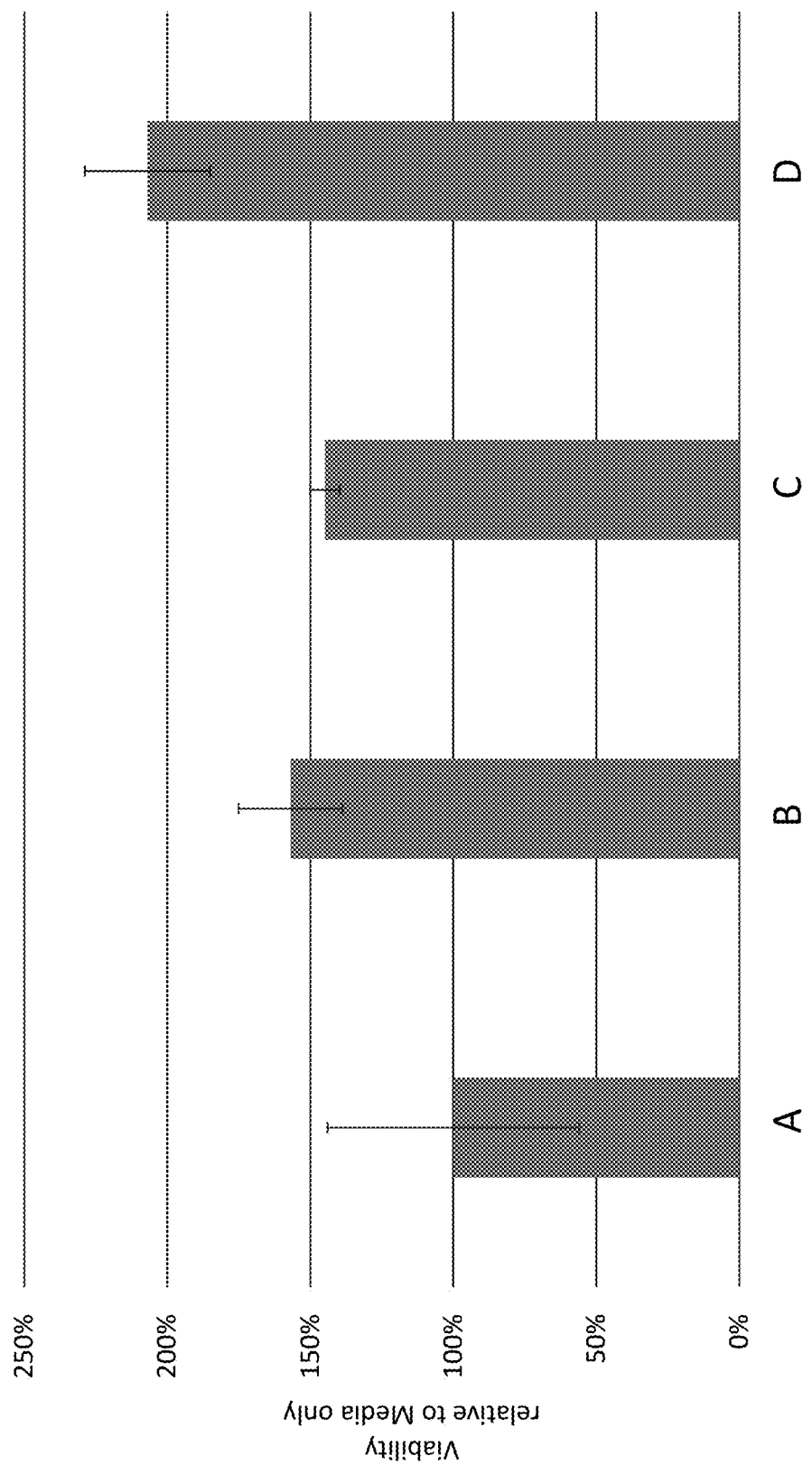
FIG. 3 depicts increased cell viability of human dermal fibroblasts when treated with a non-naturally occurring polypeptide of the disclosure (comprising an amino acid sequence according to SEQ ID NO: 2).

Human primary fibroblasts were cultured in media alone (FIG. 3; "A"), or with 0.025% w/w (FIG. 3; "B"), 0.05% w/w (FIG. 3; "C"), or 0.1% w/w (FIG. 3; "D") of a non-naturally occurring polypeptide having the amino acid sequence of SEQ ID NO: 2 for 24 hours. Cell viability was evaluated using the MTT colorimetric assay. As shown in FIG. 3, fibroblasts treated with the polypeptide of SEQ ID NO: 2 showed an increase in cell viability relative to the media only control.

A Non-Naturally Occurring Polypeptide of SEQ ID NO: 2 Increases Collagen Type I Production in Human Dermal Fibroblasts.

Figure 4:
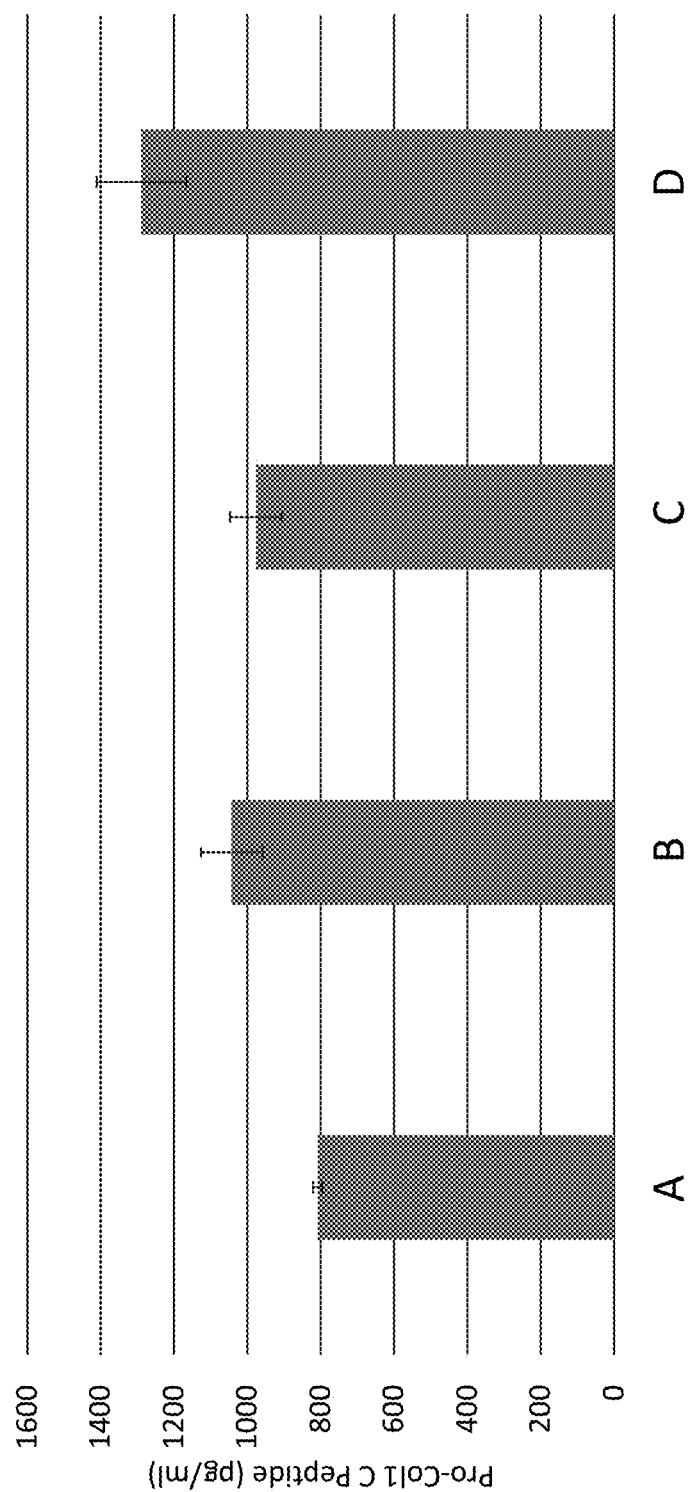
FIG. 4 depicts increased collagen type I production in human dermal fibroblasts when treated with a non-naturally occurring polypeptide of the disclosure (comprising an amino acid sequence according to SEQ ID NO: 2).

Human primary fibroblasts were cultured in media alone (FIG. 4; "A"), or with 0.025% w/w (FIG. 4; "B"), 0.05% w/w (FIG. 4; "C"), or 0.1% w/w (FIG. 4; "D") of a non-naturally occurring polypeptide having the amino acid sequence of SEQ ID NO: 2 for 24 hours. Fibroblast production of collagen type I was determined by analyzing the supernatants with an enzyme-linked immunosorbent assay (ELISA) for pro-collagen type I C-peptide, which is a readout for total secreted collagen type I. As shown in FIG. 4, fibroblasts treated with the polypeptide of SEQ ID NO: 2 secreted higher levels of collagen type I than media control-treated fibroblasts.

A Non-Naturally Occurring Polypeptide of SEQ ID NO: 2 Increases Collagen Type I Production in Human Tenocytes.

Figure 5:
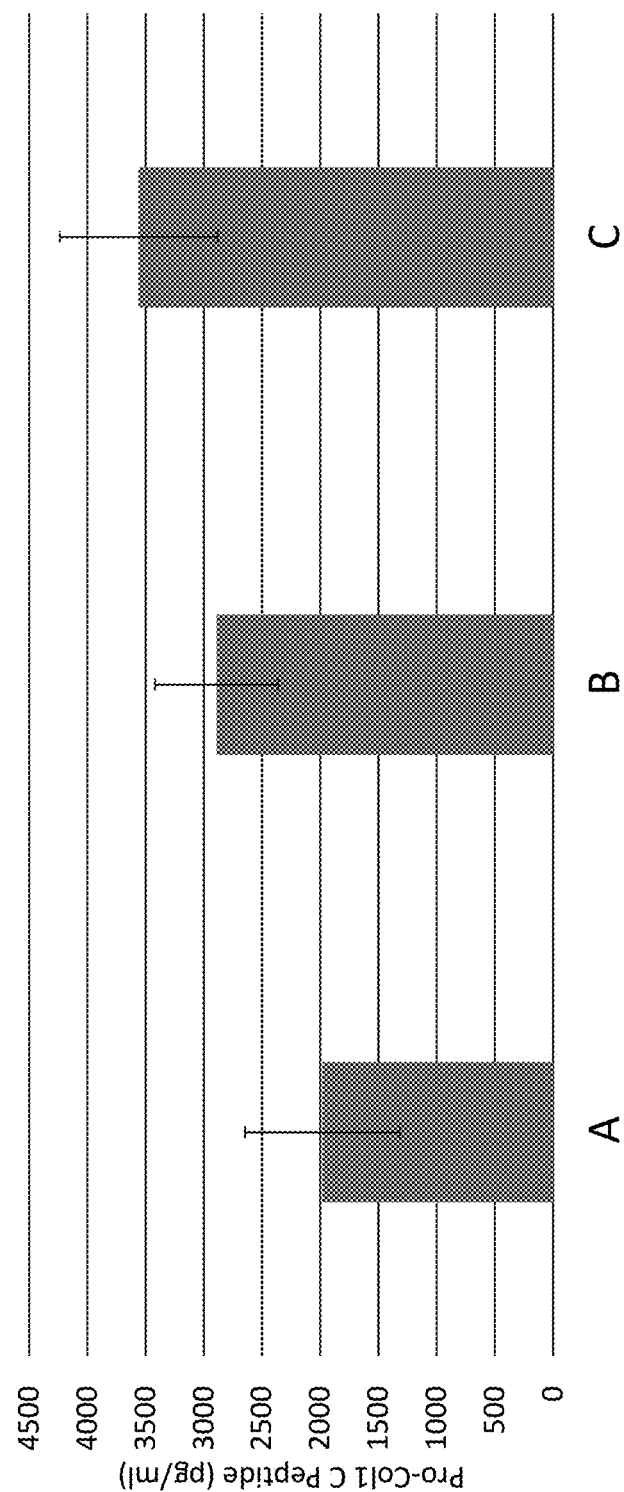
FIG. 5 depicts increased collagen type I production in tenocytes when treated with a non-naturally occurring polypeptide of the disclosure (comprising an amino acid sequence according to SEQ ID NO: 2).

Human primary tenocytes were cultured in media alone (FIG. 5; "A"), or with 0.025% w/w (FIG. 5; "B") or 0.05% w/w (FIG. 5; "C") of a non-naturally occurring polypeptide having the amino acid sequence of SEQ ID NO: 2 for 24 hours. Tenocyte production of collagen type I was determined by analyzing the supernatants with an enzyme-linked immunosorbent assay (ELISA) for pro-collagen type I C-peptide, which is a readout for total secreted collagen type I. As shown in FIG. 5, tenocytes treated with the polypeptide of SEQ ID NO: 2 secreted higher levels of collagen type I than media control-treated cells.

Example 4. Sports Drink Containing a Non-Naturally Occurring Polypeptide of the Disclosure In this example, a non-naturally occurring polypeptide of the disclosure was formulated in a sports drink.

Sports Drink Formulation:
10 g polypeptide of SEQ ID NO: 2/12 oz serving
Ingredients Listing:
Water, collagen peptides, sugar, tangerine juice concentrate, salt, citric acid, monopotassium phosphate, sodium citrate, fruit and vegetable juice [for color], natural flavor, *stevia*
Variables Tested:
1. 10 g vs. 12 g polypeptide of SEQ ID NO: 2/12 oz serving
2. 0%-15% fruit juice concentrate
3. 7 g-20 g sugar/12 oz serving
4. Sweetener systems: sucrose, monk fruit, *stevia*
5. 0.05%-0.30% citric acid Example 5. Gummies Containing a Non-Naturally Occurring Polypeptide of the Disclosure In this example, a non-naturally occurring polypeptide of the disclosure was formulated in a gummy.
2.5 g polypeptide of SEQ ID NO: 2 & 100 mg hyaluronic acid/25 g serving Ingredients Listing:

Tapioca syrup, cane sugar, water, collagen peptides, citric acid, pectin, sodium citrate, natural flavor, sodium hyaluronate, fruit and vegetable juice [for color]

Variables Tested:

1. Order of addition—polypeptide of SEQ ID NO: 2 needs to be made into a solution and added after the syrup cooking step
2. Various levels of polypeptide of SEQ ID NO: 2 (2%, 6%, 8%, 10%)
3. Polypeptide of SEQ ID NO: 2 has a buffering effect; tested different citrate/citric acid levels.

Example 6. Brownies Containing a Non-Naturally Occurring Polypeptide of the Disclosure In this example, a non-naturally occurring polypeptide of the disclosure was formulated in a brownie.

3 g polypeptide of SEQ ID NO: 2/40 g serving

Ingredients Listing:

(Bread) flour, cane sugar, cocoa powder, water, coconut oil, polypeptide of SEQ ID NO: 2, olive oil, glycerin, vanilla extract, baking soda, salt, xanthan, lecithin.

Variables Tested:

1. All-purpose flour vs. bread flour
2. Polypeptide of SEQ ID NO: 2 at 3 g, 3.75 g, 5 g, or 9 g/40 g serving
3. Reduced sugar 20%, 30%

Example 7. Properties of Non-Naturally Occurring Polypeptides of the Disclosure Related to Nutritional Use In this example, the non-naturally occurring polypeptide of SEQ ID NO: 2 was evaluated for various properties related to nutritional use.

Viscosity

Figure 7A:
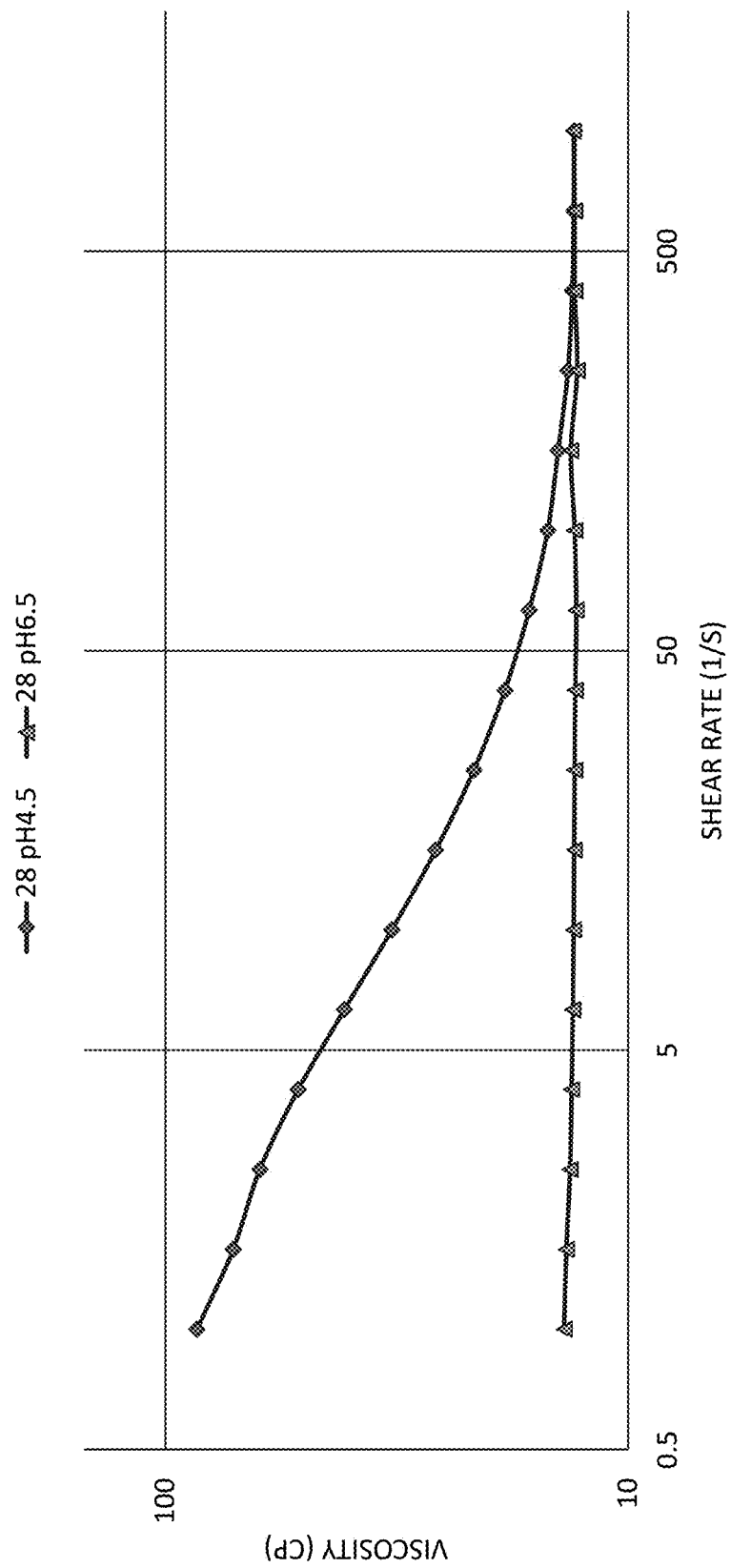
FIG. 7A depicts the effect of pH on viscosity of a solution of an exemplary non-naturally occurring polypeptide of the disclosure.
Figure 7B:
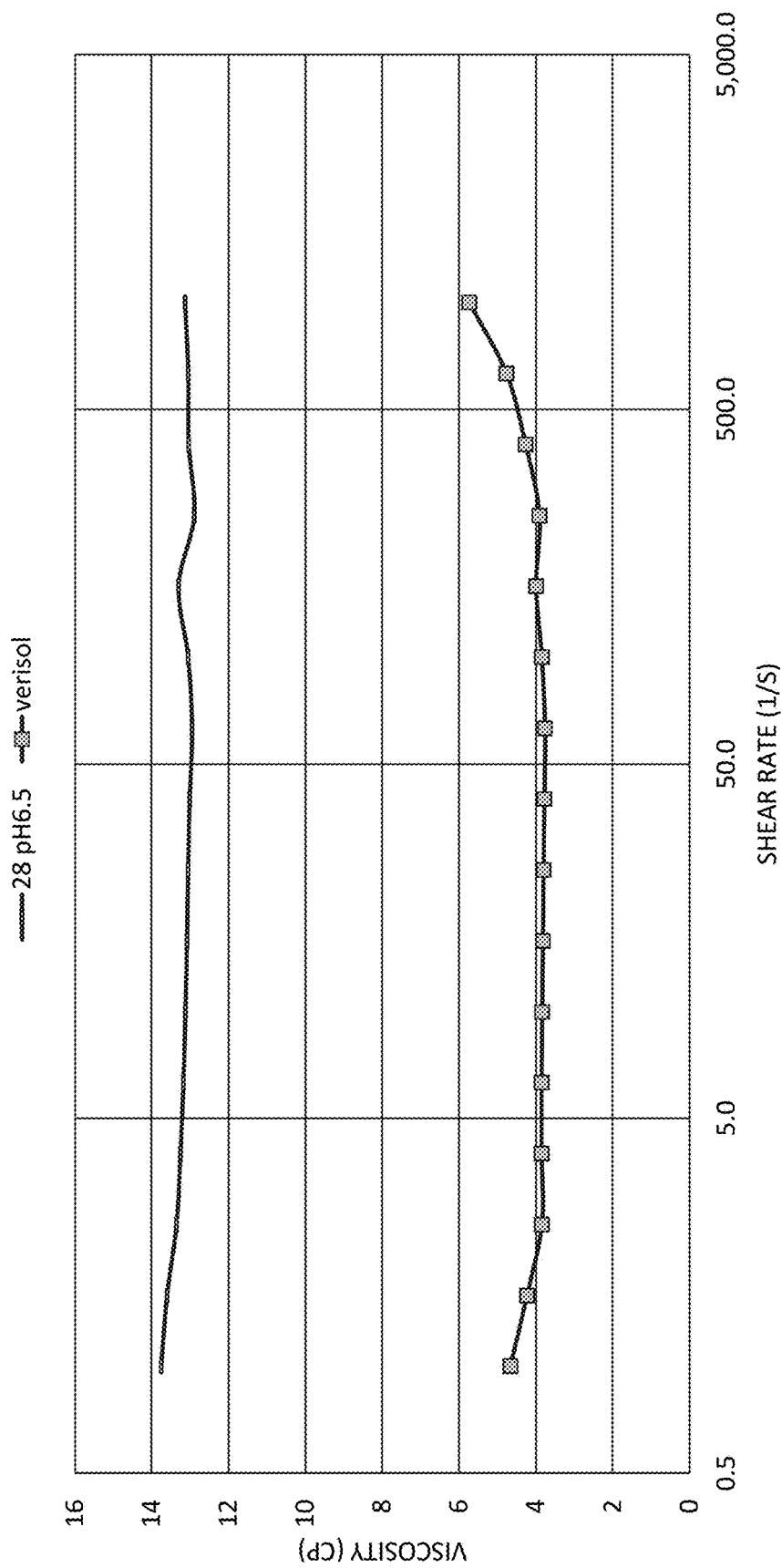
FIG. 7B depicts a comparison of the viscosity of a solution of an exemplary non-naturally occurring polypeptide of the disclosure versus a benchmark.

The non-naturally occurring polypeptides provided herein can be evaluated for viscosity in solution. In this example, a polypeptide of SEQ ID NO: 2 was shown to be soluble up to 43% w/w at pH 4.5 and 50% w/w at pH 6.5, using a flow sweep on DHR-II rheometer with 40 mm parallel plate at 25° C. A polypeptide of SEQ ID NO: 2 as a spray dried powder was found to go into solution slower in water at 50° C. or higher versus water at ambient temperature. Results are depicted in FIG. 7A and FIG. 7B.

Interactions of a polypeptide of SEQ ID NO: 2 with hydrocolloids and oils was also evaluated. Blends of a polypeptide of SEQ ID NO: 2 and gum arabic were prepared in DI water and evaluated for viscosity in the ratios according to Table 4.

TABLE 4

| Ratios of gum arabic and polypeptide blends | |
|---|---|
| Gum arabic | SEQ ID NO:2 |
| 20% | 0 |
| 20% | 10% |
| 10% | 5% |
| 10% | 0 |
| 20% | 20% |

TABLE 4-continued

| Ratios of gum arabic and polypeptide blends | |
|---|---|
| Gum arabic | SEQ ID NO:2 |
| 10% | 10% |
| 10% | 10% but pH 6.5 |

Figure 8:
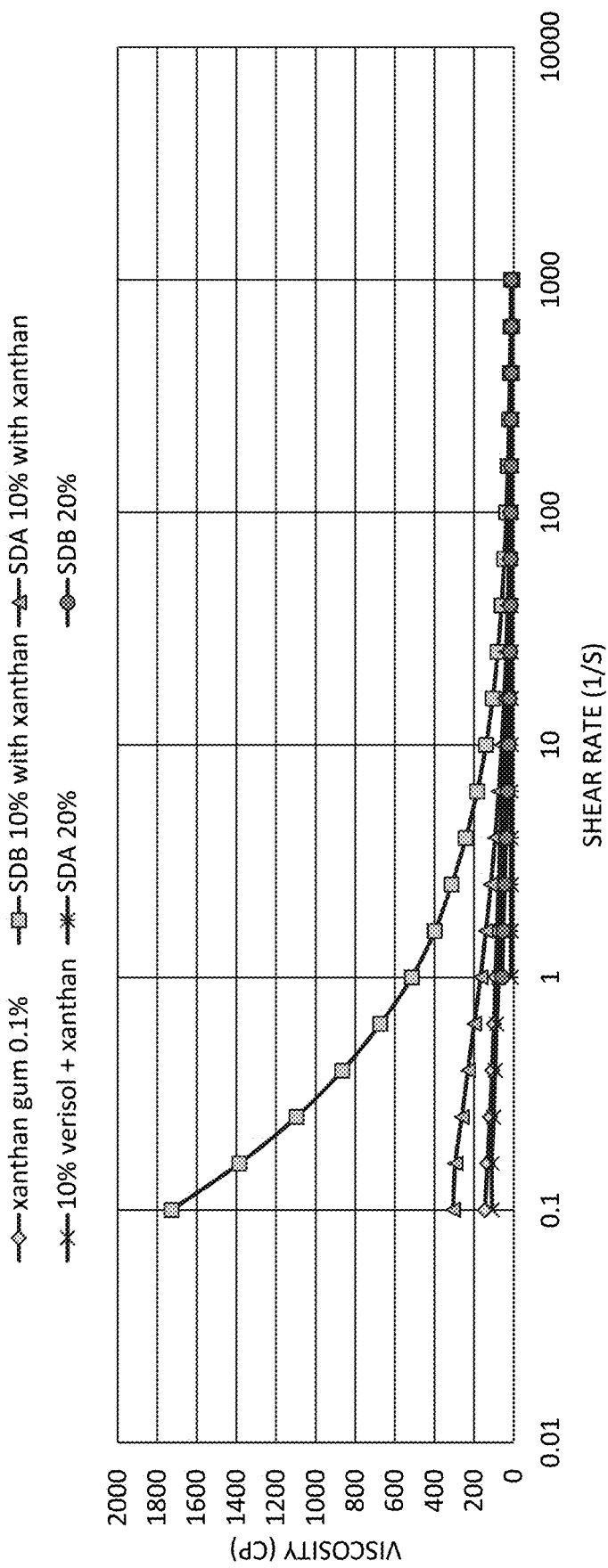
FIG. 8 depicts viscosity of various blends of an exemplary non-naturally occurring polypeptide of the disclosure and xanthan.

Blends of a polypeptide of SEQ ID NO: 2 and xanthan were prepared in DI water and evaluated for viscosity in various ratios. FIG. 8 depicts results of this study. SDA represents a polypeptide of SEQ ID NO: 2 spray dried at pH 6.5. SDB represents a polypeptide of SEQ ID NO: 2 spray dried with a feed of 20% solids at pH 4.5.

Gel Hardness

Figure 9:
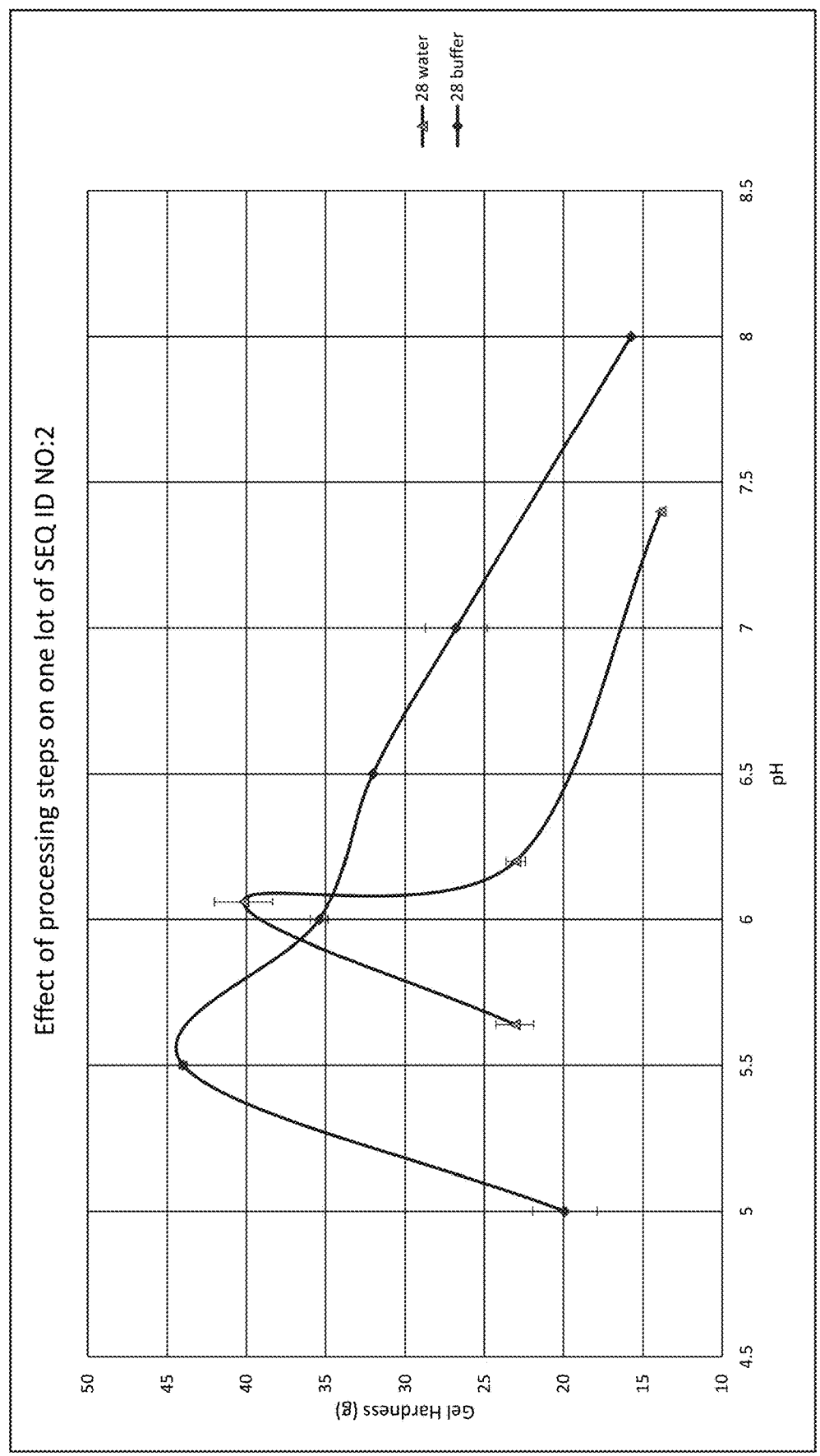
FIG. 9 depicts gel hardness of a solution of an exemplary non-naturally occurring polypeptide of the disclosure.

The non-naturally occurring polypeptides of the disclosure can be evaluated for gel hardness in solution. Briefly, 5% protein solutions (containing a polypeptide of SEQ ID NO: 2) were crosslinked with 100 u transglutaminase enzyme. Protein and enzyme mixtures were deposited in 12-well cell plates and incubated at 50° C. for 2 hours. Gels were heated to 100° C. for 10 minutes to inactivate transglutaminase enzyme. Gels were cooled at ambient temperature and stored in 4° C. overnight. Gel hardness was evaluated by molding 4 mL of gel mixture in 23 mm diameter wells. Gels were brought to ambient temperature prior to measurements, and hardness of gel was recorded as the force at which ½" stainless steel ball probe (TA-18) was depressed 2 mm into the gel at 1 mm/sec using TA.XT Plus Texture Analyzer instrument. Protein solutions were prepared in DI water or 10 mM sodium phosphate buffer, pH 7.2. Solutions were adjusted to target pH using 1M HCl or 2N NaOH prior to addition of enzyme. Results of this study are depicted in FIG. 9.

Figure 10A:
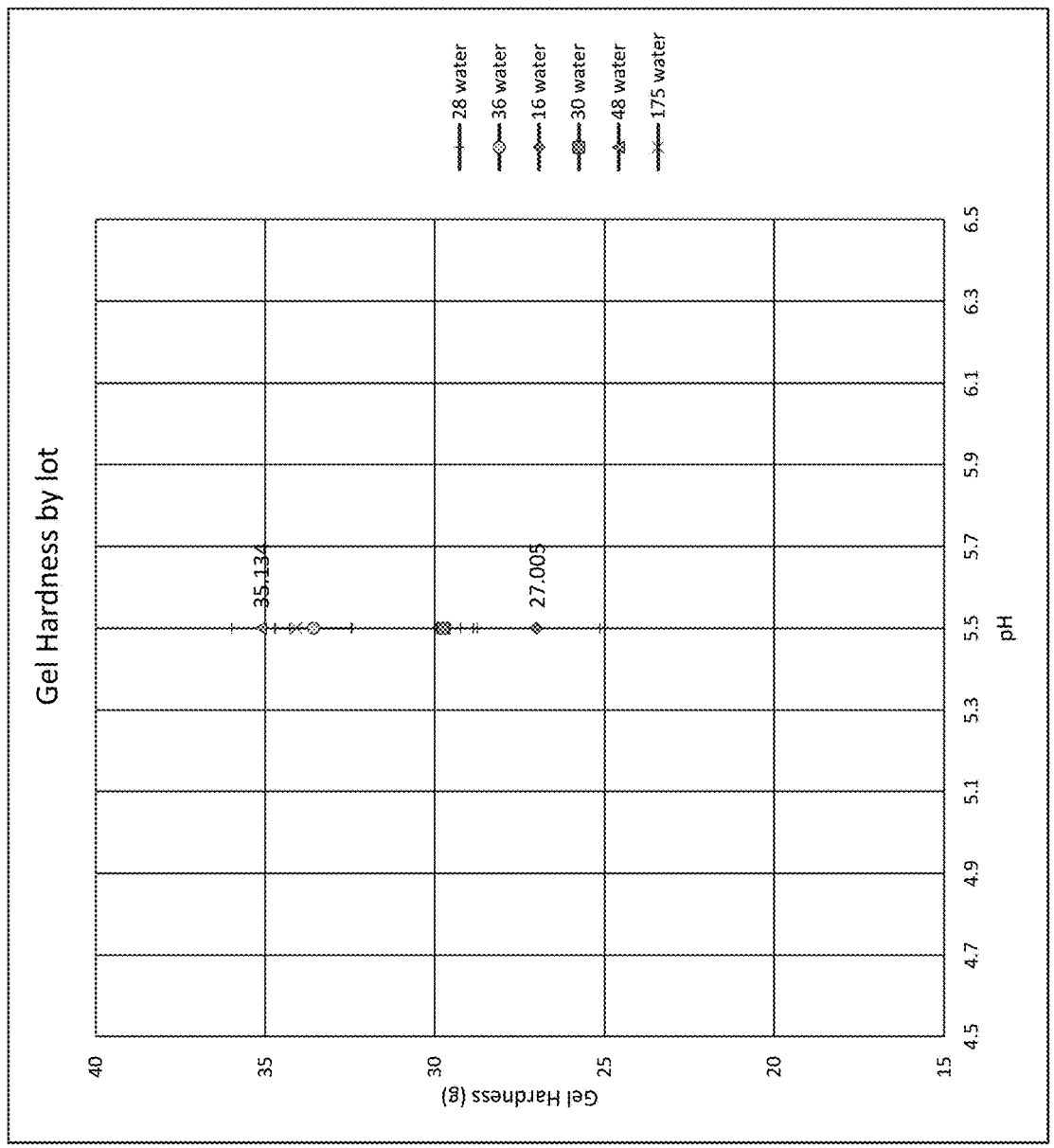
FIG. 10A and FIG. 10B depict gel hardness of solutions of various lots of an exemplary non-naturally occurring polypeptide of the disclosure.
Figure 10B:
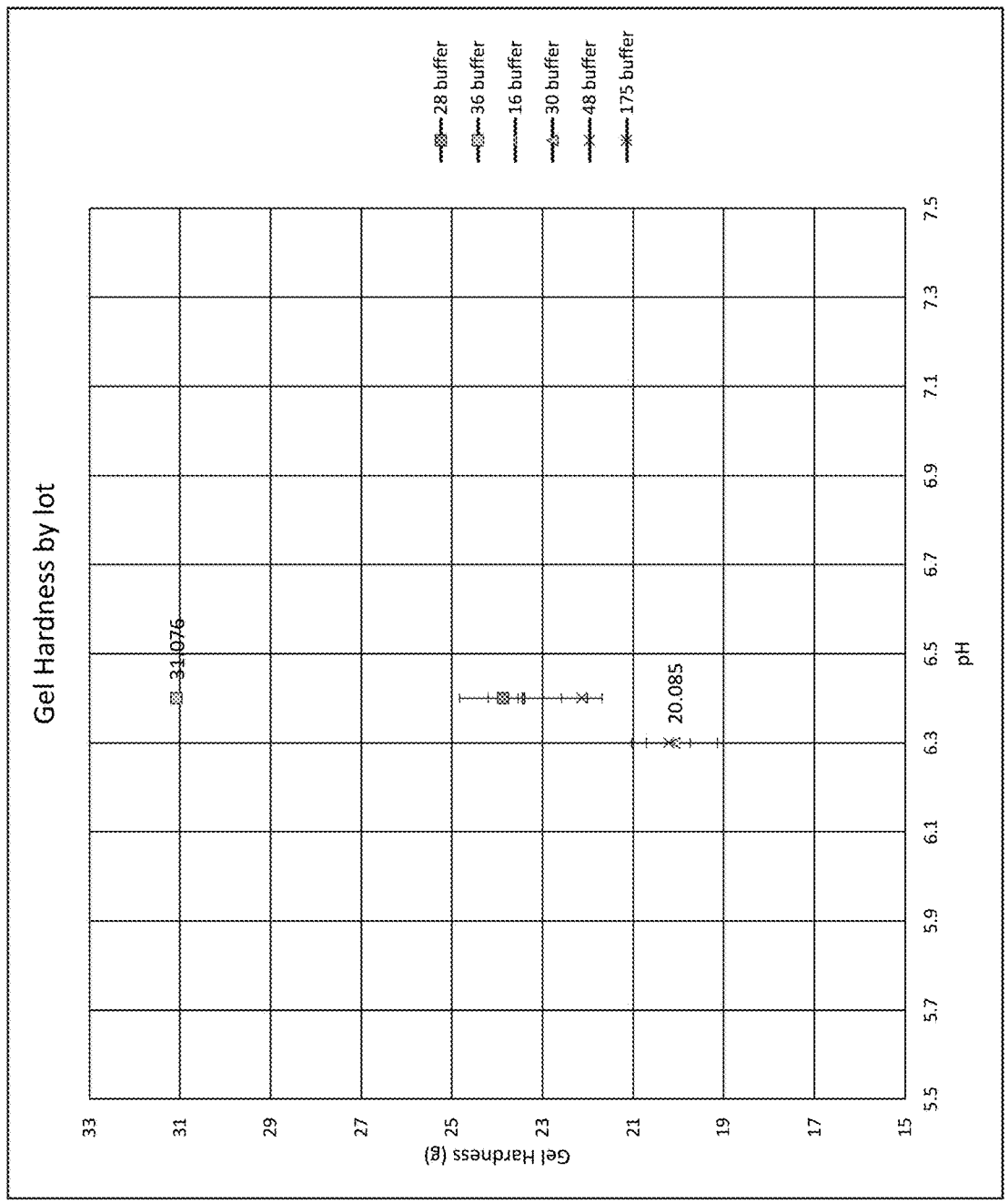

Protein solutions were prepared in DI water or 10 mM sodium phosphate buffer, pH 7.2. Solutions were adjusted to target pH using 1M HCl or 2N NaOH prior to addition of enzyme. Results are depicted in FIG. 10A and FIG. 10B. At pH 5.5, crosslinked GL21 gels range in hardness from 27-35 g. Between pH 6.3-6.4, crosslinked polypeptide gels range in hardness from 20-31 g.

Emulsion Properties

The non-naturally occurring polypeptides described herein can be evaluated for emulsion properties in solution. Protein solutions at pH 4.5 were mixed with canola oil at a 5:1 ratio and were homogenized using IKA Ultra Turrax at 10000 rpm for 10 min. Stability of emulsion was evaluated after 24 hours at ambient temperature in 12 mL conical tubes.

Foamability and Foam Stability

The non-naturally occurring polypeptides described herein can be evaluated for foaming properties in solution. 10 mL of 5% w/w of a polypeptide of SEQ ID NO: 2 solution from various lots was shaken in a conical 50 mL tube for 2 minutes. Volume of foam and time of foam collapse were recorded, and results are depicted in Table 5.

TABLE 5

Volume of foam and time of foam collapse.

| Lot number | Approximate volume foam generated (mL) | Time to foam collapse (min) |
|---|---|---|
| benchmark | 27 | 5.5 |
| PP6-GL21-20-016 | 35 | >25 |
| PP6-GL21-20-030 | 15 | 1.5 |
| PP6-GL21-20-048 | 25 | 20 |
| PP7-GL21-20-028 | 25 | >25 |
| PP7-GL21-20-036 | 30 | >25 |
| PP7-GL21-20-175 | 12 | 14 |
| PP5-GL21-20-265 | 15 | 10 |
| PP5-GL21-20-293 | 0 | — |
| PP5-GL21-20-307 | 10 | >25 |
| PP5-GL21-20-321 | 25 | 2 |

Sensory Notes

The non-naturally occurring polypeptides of the disclosure can be evaluated for sensory properties, including odor and flavor. Spray dried polypeptide of SEQ ID NO: 2 from various lots was evaluated either dried or in solution, and the results are depicted in Table 6.

TABLE 6

Sensory notes.

| Lot number | Odor powder | Odor 4.2% w/w solution | Flavor 4.2% w/w solution | Color 4.2% w/w solution |
|---|---|---|---|---|
| PP7-GL21-20-028 | Slight gelatin aroma/milk protein concentrate (MPC) | | Acidic, tart. Slightly astringent. Some dairy/grassy flavor | Clear, slight yellow hint but not as much as any of the other products |
| PP7-GL21-20-036 | Strong MPC/barnyard | Dairy/cheesy | acidic, aftertaste | Light yellow |
| PP5-GL21-20-265 | Light MPC | Dairy/cheesy | — | Clear |
| PP5-GL21-20-293 | Medium MPC | Dairy/cheesy | — | Clear |
| PP5-GL21-20-307 | Light MPC | Clean | — | Clear |
| PP5-GL21-20-321 | Sweet, light MPC | Clean, sweet | — | Clear |
| PP5-GL21-20-335 | Light MPC | Clean, faint dairy, sweet | — | Clear |
| PPS-GL21-20-337WB | Light MPC | Dairy/cheesy | — | Clear |

Solubility

Non-naturally occurring polypeptides of the disclosure can be evaluated for solubility. The effect of agglomeration with lecithin solution on compacted powder forms of a polypeptide of SEQ ID NO: 2 to increase particle size and improve solubility was evaluated. 2.5 g protein powder was dropped into 50 mL water. Wettability was evaluated by observing sinking within 20 seconds. Dissolution was evaluated with 40 seconds of slow stirring and 60 seconds of rest. Results are depicted in Table 7.

TABLE 7

Solubility of a polypeptide of SEQ ID NO: 2.

| Mesh | Particle size (um) | Compacted Yield (%) | Compacted Wet | Compacted Dissolve | Compacted with Lecithin Yield (%) | Compacted with Lecithin Wet | Compacted with Lecithin Dissolve |
|---|---|---|---|---|---|---|---|
| >18 | >1000 | 1% | — | — | 2% | — | — |
| 20-18 | 850-1000 | 13% | Y | N | 22% | Y | N |
| 25-20 | 710-850 | 22% | Y | N | 18% | Y | N |
| 30-25 | 600-710 | 12% | Y | N | 13% | Y | N |
| 35-30 | 500-600 | 12% | Y | N | 11% | Y | N |
| 40-35 | 425-500 | 7% | Y | Y | 7% | Y | Y |
| 60-40 | 250-425 | 23% | N | Y | 16% | Y | Y |
| 80-60 | 180-250 | 8% | N | N | 7% | Y | Y |
| 140-80 | 106-180 | 1% | — | — | 4% | N | Y |
| <140 | <106 | 3% | — | — | — | — | — |

Figure 11:
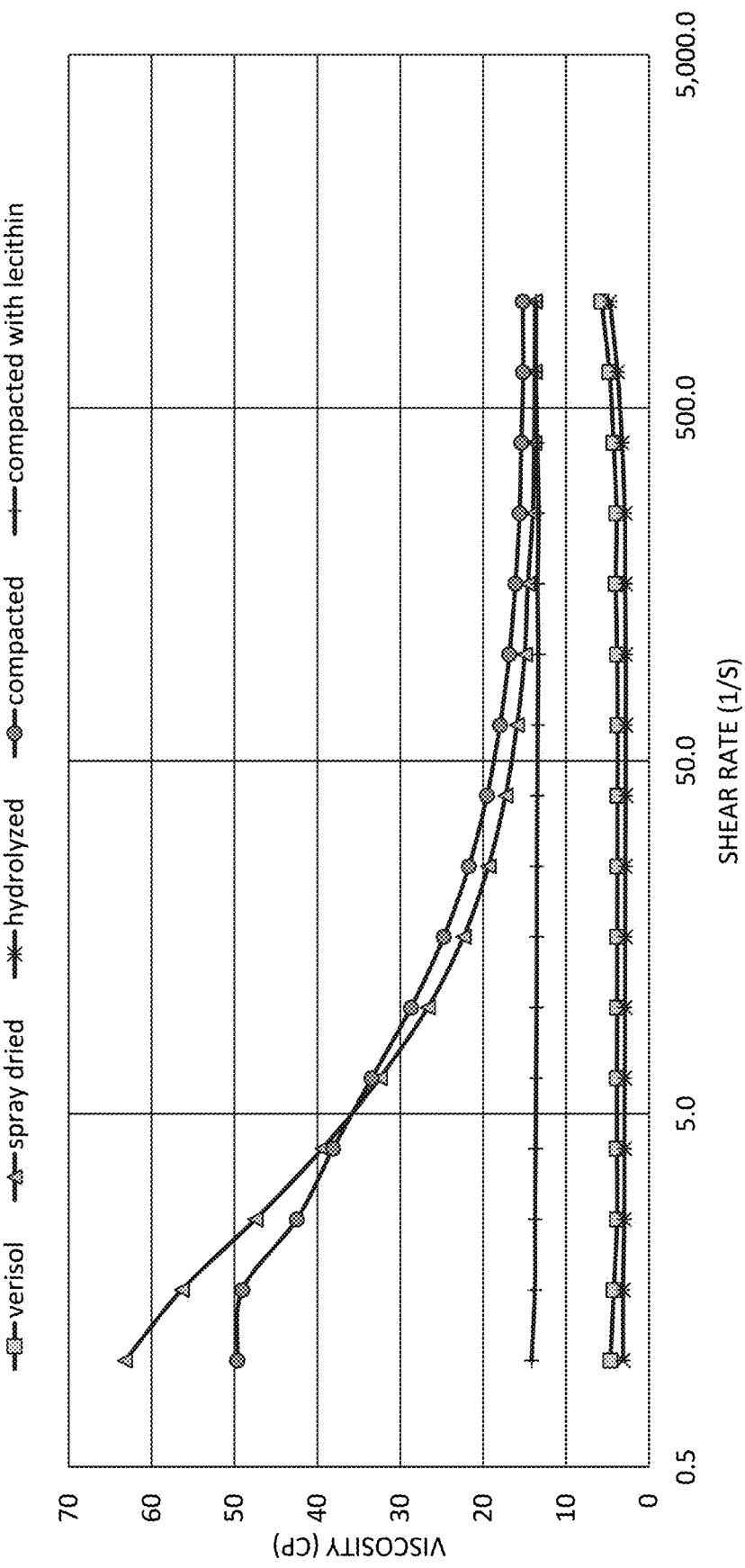
FIG. 11 depicts the effect of compaction and lecithin agglomeration on an exemplary non-naturally occurring polypeptide of the disclosure.
Figure 12:
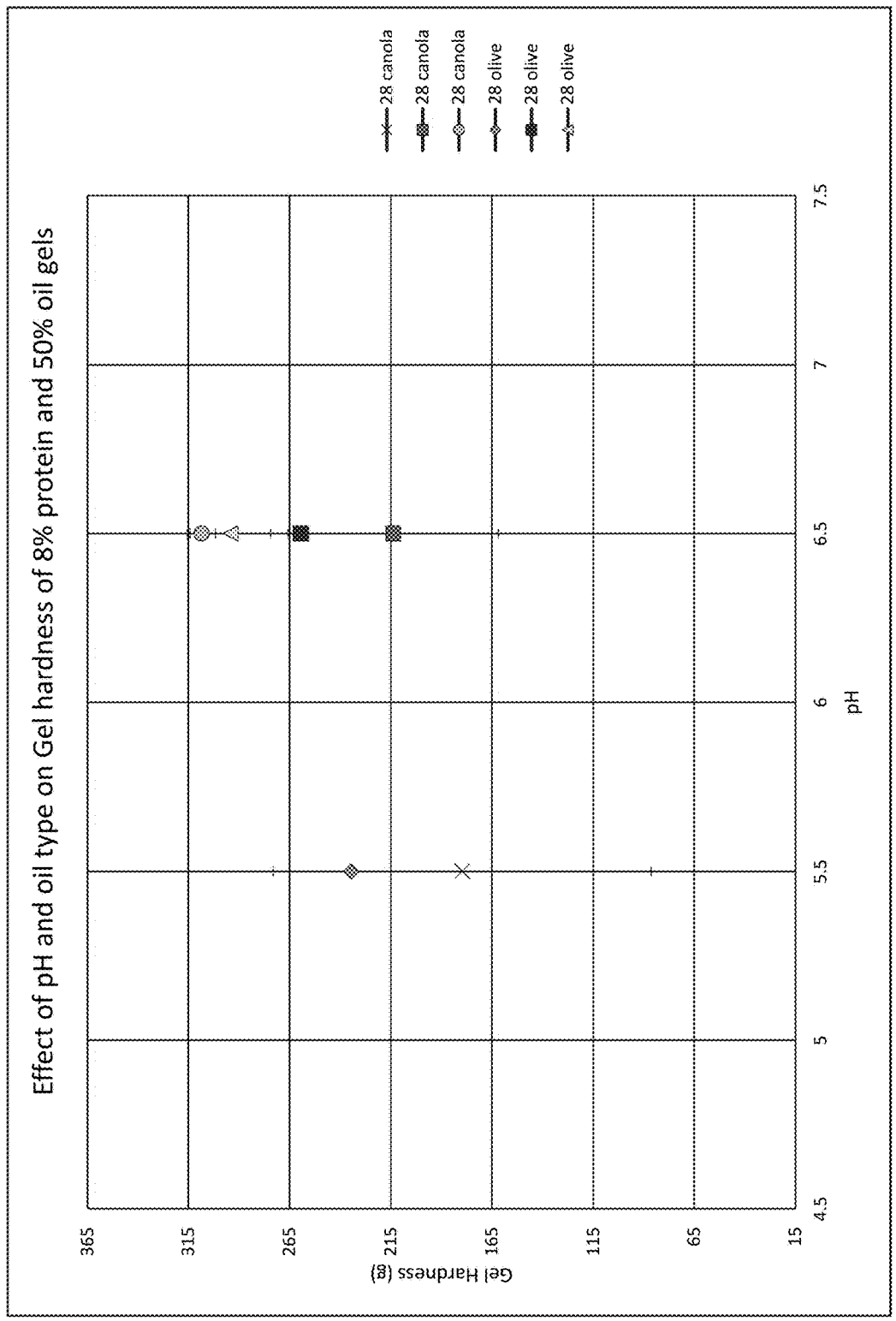
FIG. 12 depicts the effect of pH and oil type on gel hardness of gels containing an exemplary non-naturally occurring polypeptide of the disclosure.

Viscosity of solutions of a polypeptide of SEQ ID NO: 2 at 20% w/w solutions were also determined at 25° C., and results are depicted in FIG. 11.

8% w/w protein solution (containing a polypeptide of SEQ ID NO: 2) at pH 5.5 and 100 u transglutaminase enzyme was homogenized with 50% w/w oil at 26000 rpm with Polytron for 1 minute on ice. 4 g of mixture was deposited into each well of a 12-well cell plate and incubated for 2 hours at 50° C. Gels were heated to 100° C. for 10 minutes to inactivate the enzyme. Gels were cooled at ambient temperature and stored at 4° C. overnight. A polypeptide of SEQ ID NO:2 stabilized high oil emulsion during crosslinking reaction to form protein oil gel. Results are depicted in FIG.

Example 8. Polypeptide Sequence Confirmation of Products and Lack of Hydroxyproline Residues Mass spectrometry was used to confirm the sequence of a polypeptide of SEQ ID NO: 2 produced by methods according to this disclosure. Table 8 and Table 9 provide the results of peptide mapping of this polypeptide.

TABLE 8

Peptide mapping of the polypeptide of SEQ ID NO: 2. Table 8 discloses SEQ ID NOS: 35-77, respectively, in order of appearance.

| Label | Sequence | Range | | Calculated Mass (Da) | Observed Mass (Da) | Mass Error (Da) | Retention Time (min) | Intensity (counts) |
|---|---|---|---|---|---|---|---|---|
| T1-Mox | DTGFPGMPGR | 1 | 10 | 1049.4601 | 1049.4598 | -0.000216 | 7.49 | 84,835.78 |
| T1-2-clipD | DTGFPGMPGRSGD | 1 | 13 | 1292.5455 | 1292.5471 | 0.001373 | 9.13 | 126,314.00 |
| T1-2 | DTGFPGMPGRSGDPGR | 1 | 16 | 1602.7209 | 1602.7206 | -0.00029 | 8.12 | 577,210.30 |
| T1-3 | DTGFPGMPGRSGDPGRSGK | 1 | 19 | 1874.8694 | 1874.8634 | -0.005825 | 7.19 | 1,090,023.00 |
| T1-4 | DTGFPGMPGRSGDPGRSGKDGLPGSPGFK | 1 | 29 | 2830.3457 | 2830.3513 | 0.005645 | 8.6 | 6,936.58 |
| T1-clipT | TGFPGMPGR | 2 | 10 | 918.43817 | 918.43848 | 0.000225 | 8.38 | 4,768.16 |
| T1-3-clipG | GFPGMPGRSGDPGRSGK | 3 | 19 | 1658.7947 | 1658.7977 | 0.003076 | 7.19 | 228,217.00 |
| T1-3-clipP2 | PGMPGRSGDPGRSGK | 5 | 19 | 1454.7048 | 1454.7067 | 0.001883 | 7.19 | 436,082.90 |
| T1-3-clipP1 | PGRSGDPGRSGK | 8 | 19 | 1169.5901 | 1169.5885 | -0.001693 | 7.19 | 25,095.66 |
| T2 | SGDPGR | 11 | 16 | 588.2736 | | Not detected | | |
| T2-4 | SGDPGRSGKDGLPGSPGFK | 11 | 29 | 1814.8911 | 1814.8878 | -0.003236 | 6.62 | 1,121.89 |
| T3 | SGK | 17 | 19 | 291.1663 | | Not detected | | |
| T4 | DGLPGSPGFK | 20 | 29 | 974.4941 | | Not detected | | |
| T4-5-clipE | DGLPGSPGFKGE | 20 | 31 | 1159.5509 | 1159.551 | 3.39E-05 | 8.58 | 3,738.19 |
| T4-5 | DGLPGSPGFKGEVGQPGSPGLEGHR | 20 | 44 | 2431.188 | 2431.197 | 0.008649 | 8.48 | 112,201.00 |
| T4-6 | DGLPGSPGFKGEVGQPGSPGLEGHRGEPGIPGIPGNQGAK | 20 | 59 | 3803.8979 | 3803.9045 | 0.00648 | 9.39 | 441,091.10 |
| T4-7 | DGLPGSPGFKGEVGQPGSPGLEGHRGEPGIPGIPGNQGAKGQK | 20 | 62 | 4117.0728 | 4117.0747 | 0.002786 | 8.83 | 114,096.20 |
| T4-6-clipG | GLPGSPGFKGEVGQPGSPGLEGHRGEPGIPGIPGNQGAK | 21 | 59 | 3688.8711 | 3688.8735 | 0.002824 | 9.01 | 60,853.30 |
| T4-5-clipP | PGSPGFKGEVGQPGSPGLEGHR | 23 | 44 | 2146.0557 | 2146.0562 | 0.000427 | 8.47 | 14,717.96 |
| T5 | GEVGQPGSPGLEGHR | 30 | 44 | 1476.7189 | | Not detected | | |
| T5-6 | GEVGQPGSPGLEGHRGEPGIPGIPGNQGAK | 30 | 59 | 2848.4216 | 2848.4216 | -5.61E-05 | 8.28 | 71,435.91 |
| T5-7 | GEVGQPGSPGLEGHRGEPGIPGIPGNQGAKGQK | 30 | 62 | 3161.5967 | 3161.5986 | 0.00197 | 7.68 | 14,067.67 |
| T5-6-clipR | RGEPGIPGIPGNQGAK | 44 | 59 | 1546.8215 | 1546.822 | 0.00052 | 7.68 | 3,424.51 |
| T6 | GEPGIPGIPGNQGAK | 45 | 59 | 1391.7277 | | Not detected | | |
| T6-7 | GEPGIPGIPGNQGAKGQK | 45 | 62 | 1703.8955 | 1703.8969 | 0.001454 | 7.58 | 13,208.12 |
| T6-8 | GEPGIPGIPGNQGAKGQKGEIGPPGLPGAK | 45 | 74 | 2777.4824 | 2777.48 | -0.002657 | 9.09 | 24,234.60 |
| T6-9 | GEPGIPGIPGNQGAKGQKGEIGPPGLPGAKGSPGETGLMGPEGSFGLPGAPGPK | 45 | 98 | 4955.5239 | 4955.5317 | 0.008078 | 10.72 | 9,805.94 |
| T6-7-clipP | PGNQGAKGQK | 53 | 62 | 983.51483 | 983.51324 | -0.001589 | 8.83 | 4,871.83 |
| T6-8-clipP | PGNQGAKGQKGEIGPPGLPGAK | 53 | 74 | 2057.1018 | 2057.1055 | 0.003865 | 9.41 | 1,757.15 |
| T7 | GQK | 60 | 62 | 332.1928 | | Not detected | | |
| T7-8-Met1 | GQKGEIGPPGLPGAK | 60 | 74 | 1418.7882 | 1418.79 | 0.002054 | 8.04 | 3,103.51 |
| T7-8-clipK | KGEIGPPGLPGAK | 62 | 74 | 1219.6925 | 1219.691 | -0.001366 | 7.46 | 11,881.92 |
| T8 | GEIGPPGLPGAK | 63 | 74 | 1092.6047 | | Not detected | | |
| T8-11 | GEIGPPGLPGAKGSPGETGLMGPEGSFGLPGAPGPKGDKGEPGLQGKPGSSGAK | 63 | 116 | 4920.4717 | 4920.4771 | 0.005323 | 9.79 | 81,370.18 |

TABLE 8-continued

Peptide mapping of the polypeptide of SEQ ID NO: 2. Table 8 discloses SEQ ID NOS: 35-77, respectively, in order of appearance.

| Label | Sequence | Range | Calculated Mass (Da) | Observed Mass (Da) | Mass Error (Da) | Retention Time (min) | Intensity (counts) |
|---|---|---|---|---|---|---|---|
| T8-clipI | IGPPGLPGAK | 65 74 | 905.53345 | 905.53308 | -0.00042 | 8.71 | 28,037.06 |
| T9-cation | GSPGETGLMGPEGSFGLPGAPGPK | 75 98 | 2234.0081 | 2233.9998 | -0.008257 | 11.12 | 48,341.35 |
| T9 | GSPGETGLMGPEGSFGLPGAPGPK | 75 98 | 2197.0593 | | Not detected | | |
| T9-10-clipD | GSPGETGLMGPEGSFGLPGAPGPKGD | 75 100 | 2368.1006 | 2368.1003 | -0.000254 | 11.24 | 10,231.43 |
| T9-10 | GSPGETGLMGPEGSFGLPGAPGPKGDK | 75 101 | 2496.1956 | 2496.1887 | -0.006757 | 10.11 | 99,126.63 |
| T9-clipT | TGLMGPEGSFGLPGAPGPK | 80 98 | 1768.8818 | 1768.88 | -0.001801 | 11.1 | 5,679.79 |
| T9-clipG | GLMGPEGSFGLPGAPGPK | 81 98 | 1667.8341 | 1667.8339 | -0.00031 | 11.1 | 1,873.69 |
| T9-clipS | SFGLPGAPGPK | 88 98 | 1026.5498 | 1026.5485 | -0.00134 | 8.97 | 904.06 |
| T10-11 | GDKGEPGLQGKPGSSGAK | 99 116 | 1668.8431 | 1668.8383 | -0.004932 | 5.46 | 475,309.00 |
| T11-11-clipK | KGEPGLQGKPGSSGAK | 101 116 | 1496.7947 | 1496.7939 | -0.000828 | 5.39 | 5,921.06 |
| T11 | GEPGLQGKPGSSGAK | 102 116 | 1369.707 | | Not detected | | |

TABLE 9

Peptide mapping of the polypeptide of SEQ ID NO: 2. Table 9 discloses SEQ ID NOS: 78-112, respectively, in order of appearance.

| Label | Sequence | Range | Calculated Mass (Da) | Observed Mass (Da) | Mass Error (Da) | Retention Time (min) | Intensity (counts) |
|---|---|---|---|---|---|---|---|
| T11-13 | GEPGLQGKPGSSGAKGEPGGPGAPGEPGYPGIPGTQGIKGDK | 102 143 | 3839.908 | 3839.9158 | 0.007516 | 7.99 | 15,528.34 |
| T12 | GEPGGPGAPGEPGYPGIPGTQGIK | 117 140 | 2189.0752 | 2189.0723 | -0.003083 | 9.65 | 145,576.30 |
| T12-13 | GEPGGPGAPGEPGYPGIPGTQGIKGDK | 117 143 | 2489.2188 | 2489.219 | 0.000101 | 8.74 | 45,482.75 |
| T12-14-clipP4 | PGEPGYPGIPGTQGIKGDKGSQGESGIQGR | 125 154 | 2923.4424 | 2923.4473 | 0.005102 | 7.56 | 18,260.02 |
| T12-14-clipP3 | PGYPGIPGTQGIKGDKGSQGESGIQGR | 128 154 | 2640.3257 | 2640.3262 | 0.000495 | 7.58 | 16,118.65 |
| T12-14-clipP2 | PGIPGTQGIKGDKGSQGESGIQGR | 131 154 | 2323.188 | 2323.1851 | -0.0029 | 8.33 | 16,247.45 |
| T12-14-clipP1 | PGTQGIKGDKGSQGESGIQGR | 134 154 | 2056.0298 | 2056.0305 | 0.000825 | 7.56 | 24,994.64 |
| T12-15-clipP | PGTQGIKGDKGSQGESGIQGRK | 134 155 | 2056.0298 | 2056.0308 | 0.00072 | 8.33 | 13,644.56 |
| T13 | GDK | 141 143 | 319.1612 | | Not detected | | |
| T13-14 | GDKGSQGESGIQGR | 141 154 | 1374.6488 | 1374.6508 | 0.001875 | 5.23 | 66,051.58 |
| T13-15 | GDKGSQGESGIQGRK | 141 155 | 1374.6488 | 1374.6508 | 0.001875 | 5.23 | 66,051.58 |
| T13-16 | GDKGSQGESGIQGRKGEK | 141 158 | 1816.9027 | 1816.899 | -0.00382 | 2.88 | 2,494.46 |
| T13-17 | GDKGSQGESGIQGRKGEKGR | 141 160 | 2030.0253 | 2030.022 | -0.003288 | 2.72 | 2,147.75 |
| T13-14-clipK | KGSQGESGIQGR | 143 154 | 1202.6003 | 1202.5985 | -0.00199 | 3.44 | 2,745.49 |
| T14 | GSQGESGIQGR | 144 154 | 1075.5126 | | Not detected | | |
| T14-15 | GSQGESGIQGRK | 144 155 | 1202.6003 | 1202.5985 | -0.00199 | 3.44 | 2,745.49 |
| T14-16 | GSQGESGIQGRKGEK | 144 158 | 1516.7594 | 1516.7587 | -0.000831 | 3.02 | 1,968.24 |
| T14-17 | GSQGESGIQGRKGEKGR | 144 160 | 1729.882 | 1729.8776 | -0.00443 | 2.79 | 2,134.92 |
| T15 | K | 155 155 | 147.1128 | | Not detected | | |
| T15-18 | KGEKGRQGNPGLQGTEGLR | 155 173 | 1981.0453 | 1981.0386 | -0.006898 | 5.56 | 19,503.56 |

TABLE 9-continued

Peptide mapping of the polypeptide of SEQ ID NO: 2. Table 9 discloses SEQ ID NOS: 78-112, respectively, in order of appearance.

| Label | Sequence | Range | Calculated Mass (Da) | Observed Mass (Da) | Mass Error (Da) | Retention Time (min) | Intensity (counts) |
|---|---|---|---|---|---|---|---|
| T15-19 | KGEKGRQGNPGLQGTEGLRGEQGEK | 155 179 | 2609.3269 | 2609.3267 | −0.000342 | 5.51 | 112,503.40 |
| T16-18 | GEKGRQGNPGLQGTEGLR | 156 173 | 1852.9503 | 1852.9458 | −0.004281 | 5.76 | 1,739.51 |
| T16-20 | GEKGRQGNPGLQGTEGLRGEQGEKGEK | 156 182 | 2795.3911 | 2795.3877 | −0.0033 | 5.51 | 8,967.10 |
| T17 | GR | 159 160 | 232.1404 | Not detected | | | |
| T17-18-clipL | GRQGNPGLQGTEGL | 159 172 | 1382.6902 | 1382.6887 | −0.001582 | 7.58 | 12,756.85 |
| T17-18 | GRQGNPGLQGTEGLR | 159 173 | 1538.7914 | 1538.7919 | 0.000687 | 6.31 | 25,249.43 |
| T17-19 | GRQGNPGLQGTEGLRGEQGEK | 159 179 | 2167.073 | 2167.0701 | −0.002904 | 5.83 | 106,768.80 |
| T17-20 | GRQGNPGLQGTEGLRGEQGEKGEK | 159 182 | 2481.2319 | 2481.2329 | 0.000921 | 5.59 | 36,064.79 |
| T17-21-clipD | GRQGNPGLQGTEGLRGEQGEKGEKGD | 159 184 | 2653.2805 | 2653.2791 | −0.001494 | 5.66 | 10,397.58 |
| T18 | QGNPGLQGTEGLR | 161 173 | 1326.676 | Not detected | | | |
| T18-19 | QGNPGLQGTEGLRGEQGEK | 161 179 | 1936.9238 | 1936.9227 | −0.001056 | 7.68 | 14,110.98 |
| T18-20 | QGNPGLQGTEGLRGEQGEKGEK | 161 182 | 2268.1094 | 2268.1101 | 0.000698 | 5.98 | 60,817.64 |
| T18-21-clipD | QGNPGLQGTEGLRGEQGEKGEKGD | 161 184 | 2440.158 | 2440.1602 | 0.002185 | 6.14 | 17,499.44 |
| T18-21-clipR | RGEQGEKGEKGDPGIR | 173 188 | 1711.8601 | 1711.8606 | 9.05E−05 | 5.06 | 7,889.07 |
| T19 | GEQGEK | 174 179 | 647.2995 | Not detected | | | |
| T19-21 | GEQGEKGEKGDPGIR | 174 188 | 1555.759 | 1555.7548 | −0.00416 | 5.3 | 24,352.07 |
| T20 | GEK | 180 182 | 333.1768 | Not detected | | | |
| T20-21 | GEKGDPGIR | 180 188 | 927.47742 | 927.47589 | −0.001604 | 5.25 | 156,253.20 |
| T21 | GDPGIR | 183 188 | 614.3256 | Not detected | | | |

Analysis was also performed to evaluate any amino acid or peptide modifications present in the produced polypeptide of SEQ ID NO: 2. (Table 10). In a few instances, additional confirmatory analyses were performed to differential methionine oxidation from the presence of hydroxyproline residues. For example, based upon the fragmentation results from MS/MS scans, the tryptic peptide T1 (sequence DTGFPGMPGR (SEQ ID NO: 35)) was shown to contain a methionine oxidation rather than a proline hydroxylation. Based on such results, it was conclusively determined that tryptic peptide 1 (T1) has oxidation at methionine position 7 and no evidence of hydroxyproline at position 5 or 8. Similarly, where there is another methionine in position 83 in tryptic peptide 9 (T9), there were no detectable levels of methionine oxidation, hydroxyproline in positions 77, 85, 92, 95, and 97, or hydroxylysine at position 98 of the polypeptide. Accordingly, the truncated collagen polypeptides of the present disclosure also differ from naturally occurring collagen polypeptides in their lack of hydroxyproline residues.

TABLE 10

Analysis of amino acid and peptide modifications of the polypeptide of SEQ ID NO: 2.

| Modifications | Label | Sequence | Intensity (counts) | Relative Instensity (%) |
|---|---|---|---|---|
| Oxidation Met, Missed Cleavages, N and C terminal Clips | T1 | Oxidation (M) | 84,835.78 | 3.29 |
| | | Clippped (T) | 4,768.16 | 0.18 |
| | T1-2 | Missed Cleavage, Clippped (D) | 126,314.00 | 4.90 |
| | | Missed Cleavage | 577,210.30 | 22.38 |
| | T1-3 | 2 Missed Cleavages | 1,090,023.00 | 42.26 |
| | | 2 Missed Cleavages, Clipped (G) | 228,217.00 | 8.85 |
| | | 2 Missed Cleavages, Clipped (P1) | 436,082.90 | 16.91 |
| | | 2 Missed Cleavages, Clipped (P2) | 25,095.66 | 0.97 |
| | T1-4 | 3 Missed Cleavages | 6,936.58 | 0.27 |

TABLE 10-continued

Analysis of amino acid and peptide modifications of the polypeptide of SEQ ID NO: 2.

| Modifications | Label | Sequence | Intensity (counts) | Relative Instensity (%) |
|---|---|---|---|---|
| Missed Cleavages, N and C Terminal Clips | T4 | Unmodified | 233,635.20 | 23.83 |
| | T4-5 | Missed Cleavgae, Clipped (E) | 3,738.19 | 0.38 |
| | | Missed Cleavage | 112,201.00 | 11.45 |
| | T4-6 | 2 Missed Cleavages | 441,091.10 | 44.99 |
| | | 2 Missed Cleavages, Clipped (P) | 14,717.96 | 1.50 |
| | T4-7 | 3 Missed Cleavages | 114,096.20 | 11.64 |
| | | 3 Missed Cleavages, Clipped (G) | 60,853.30 | 6.21 |
| Missed Cleavages, N Terminal Clip | T5 | Unmodified | 4,628.28 | 1.63 |
| | T5-6 | Missed Cleavage | 71,435.91 | 25.11 |
| | | Missed Cleavage, Clipped (R) | 3,424.51 | 1.20 |
| | T6 | Unmodified | 177,768.80 | 62.48 |
| | T5-7 | 2 Missed Cleavages | 14,067.67 | 4.94 |
| | T6-7 | Missed Cleavage | 13,208.12 | 4.64 |
| Missed Clevages, N Terminal Clips, Methyl Ile, Dehydrated Gln | T6-8 | 2 Missed Cleavages | 24,234.60 | 26.78 |
| | T6-9 | 3 Missed Cleavages | 9,805.94 | 10.83 |
| | T7-8 | Missed Cleavage, Clipped (P) | 4,871.83 | 5.38 |
| | | Missed Cleavage, Methyl (I) | 3,103.51 | 3.43 |
| | | Missed Cleavage, Clipped (K) | 11,881.92 | 13.13 |
| | T7-9 | 2 Missed Cleavages, Clipped (P) | 1,757.15 | 1.94 |
| | T8 | Dehydrated (E) | 6,818.71 | 7.53 |
| | | Clipped (I) | 28,037.06 | 30.98 |
| Cation K, Missed Cleavgaes, N Terminal Clips | T9 | Cation K | 48,341.35 | 19.07 |
| | | Clipped (T) | 5,679.79 | 2.24 |
| | | Clipped (G) | 1,873.69 | 0.74 |
| | | Clipped (S) | 904.06 | 0.36 |
| | T9-10 | Missed Cleavage | 99,126.63 | 39.11 |
| | | Missed Cleavage, Clipped (D) | 10,231.43 | 4.04 |
| | T10-11 | Missed Cleavage, Clipped (K) | 5,921.06 | 2.34 |
| | T8-11 | 3 Missed Cleavages | 81,370.18 | 32.11 |
| Missed Cleavages | T11 | Unmodified | 40,875.16 | 72.47 |
| | T11-13 | 2 Missed Cleavages | 15,528.34 | 27.53 |
| Missed Cleavages, N Terminal Clips | T12 | Unmodified | 145,576.30 | 51.93 |
| | T12-13 | Missed Cleavage | 45,482.75 | 16.23 |
| | T12-14 | 2 Missed Cleavages, Clipped (P4) | 18,260.02 | 6.51 |
| | | 2 Missed Cleavages, Clipped (P3) | 16,118.65 | 5.75 |
| | | 2 Missed Cleavages, Clipped (P2) | 16,247.45 | 5.80 |
| | | 2 Missed Cleavages, | 24,994.64 | 8.92 |
| | T12-15 | 3 Missed Cleavages, Clipped (P) | 13,644.56 | 4.87 |
| Missed Cleavages | T13-14 | Missed Cleavage | 66,051.58 | 36.91 |
| | T13-16 | 3 Missed Cleavages | 2,494.46 | 1.39 |
| | T13-17 | 4 Missed Cleavages | 2,147.75 | 1.20 |
| | T14 | Unmodified | 101,400.00 | 56.67 |
| | T14-15 | Missed Cleavages | 2,745.49 | 1.53 |
| | T14-17 | 3 Missed Cleavages | 2,134.92 | 1.19 |
| | T14-16 | 2 Missed Cleavages | 1,968.24 | 1.10 |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the embodiments of the disclosure. It is intended that the following claims define the scope of the disclosure and that methods and structures within the scope of these claims and their equivalents be covered thereby.

What is claimed is:

1. A non-naturally occurring polypeptide comprising an amino acid sequence having at least 80% sequence identity to a truncate of SEQ ID NO: 31, wherein the truncate of SEQ ID NO: 31 has an N-terminal truncation of 50 amino acids to 650 amino acids, a C-terminal truncation of 50 amino acids to 250 amino acids, or both the N-terminal truncation and the C-terminal truncation, relative to SEQ ID NO: 31.

2. The non-naturally occurring polypeptide of claim 1, comprising an amino acid sequence having at least 90% sequence identity to the truncate of SEQ ID NO: 31.

3. The non-naturally occurring polypeptide of claim 1, comprising an amino acid sequence having at least 95% sequence identity to the truncate of SEQ ID NO: 31.

4. The non-naturally occurring polypeptide of claim 1, comprising the amino acid sequence of the truncate of SEQ ID NO: 31.

5. The non-naturally occurring polypeptide of claim 1, wherein the truncate of SEQ ID NO: 31 comprises the N-terminal truncation.

6. The non-naturally occurring polypeptide of claim 1, wherein the truncate of SEQ ID NO: 31 comprises the C-terminal truncation.

7. The non-naturally occurring polypeptide of claim 1, wherein the non-naturally occurring polypeptide does not comprise one or more of: a laminin G domain, a Von Willebrand factor type A (vWA) domain, and a fibrillar collagen C-terminal domain.

8. The non-naturally occurring polypeptide of claim 1, wherein the non-naturally occurring polypeptide comprises one or more collagen triple helix repeats.

9. The non-naturally occurring polypeptide of claim 1, wherein the non-naturally occurring polypeptide is 50 amino acids to 250 amino acids in length.

10. The non-naturally occurring polypeptide of claim 1, comprising the amino acid sequence of SEQ ID NO: 2 or SEQ ID NO: 6.

11. The non-naturally occurring polypeptide of claim 1, consisting of the amino acid sequence of SEQ ID NO: 2 or SEQ ID NO: 6.

12. The non-naturally occurring polypeptide of claim 1, comprising or consisting of an amino acid sequence having at least 80% sequence identity to SEQ ID NO: 2 or SEQ ID NO: 6.

13. The non-naturally occurring polypeptide of claim 1, wherein the non-naturally occurring polypeptide is monomeric.

14. The non-naturally occurring polypeptide of claim 1, wherein the non-naturally occurring polypeptide does not form a stable triple helix structure of a naturally occurring collagen.

15. The non-naturally occurring polypeptide of claim 1, wherein fewer than 10% of prolines present in the non-naturally occurring polypeptide are hydroxylated.

16. The non-naturally occurring polypeptide of claim 1, wherein the non-naturally occurring polypeptide comprises less than 5 wt. % glycosylation.

17. A composition comprising the non-naturally occurring polypeptide of claim 1, wherein the composition is a product formulated for consumption by an individual.

18. The composition of claim 17, wherein the product is a food, a beverage, or a nutraceutical supplement, and wherein the non-naturally occurring polypeptide is an ingredient present in the product in a concentration of at least 0.1% w/w.

19. The composition of claim 17, wherein the product is a powder, and wherein the non-naturally occurring polypeptide is at least 50% w/w of the powder.

20. The composition of claim 17, wherein the product is a nutritive polypeptide product formulated as a food, a beverage, a medical food, a supplement, a pharmaceutical, or any combination thereof.

21. The composition of claim 17, wherein the product provides a dosage of from 1 g to 5 g of the non-naturally occurring polypeptide.

22. The composition of claim 17, wherein the product provides a dosage of from 2 g to 10 g of the non-naturally occurring polypeptide.

23. A composition comprising the non-naturally occurring polypeptide of claim 1, wherein the composition is a food ingredient.

24. The composition of claim 23, further comprising at least one of a carbohydrate, a lipid, a supplemental mineral, a supplemental vitamin, an excipient, a buffering agent, a flavoring agent, a sweetener, or a coloring agent.

25. A method of improving the appearance of the skin, the hair, and/or the nails of a subject, and/or improving bone, muscle, and/or joint health in the subject, the method comprising: administering to the subject a composition of claim 17.

26. The method of claim 25, wherein the administering comprises orally administering to the subject.

27. A method of improving gut health, altering or improving the microbiome, or altering and/or reducing inflammation or tissue repair in a subject, the method comprising administering to the subject a composition of claim 17.

28. The method of claim 27, wherein the administering comprises orally administering to the subject.

29. A recombinant cell containing therein at least one copy of a heterologous nucleic acid sequence encoding a non-naturally occurring polypeptide of claim 1.

30. The recombinant cell of claim 29, wherein the recombinant cell lacks an enzyme that hydroxylates one or more amino acids of the non-naturally occurring polypeptide, wherein the enzyme is selected from the group consisting of: prolyl 4-hydroxylase, prolyl 3-hydroxylase, and both.

* * * * *

SEQUENCE LISTING

```
<160> NUMBER OF SEQ ID NOS: 112

<210> SEQ ID NO 1
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gataccggtt ttccgggtat gcctggtcgt agcggtgatc cgggtcgtag cggtaaagat      60
```

```
ggtctgcctg gtagcccggg ttttaaaggt gaagttggtc agccaggtag ccctggtctg    120
gaaggtcatc gtggtgaacc gggtattcca ggtattccgg gtaatcaggg tgcaaaaggt    180
cagaaaggcg aaattggtcc tccgggtctg ccaggtgcca aggttctccc ggtgaaacc     240 ggtctgatgg gtcctgaagg tagctttggc ctgcctggtg caccgggtcc gaaaggtgac    300
aaaggtgaac tggtctgcag ggtaaaccg ggtagcagcg gtgcaaaagg cgaaccaggt     360
ggtccgggtg ctccgggtga accaggctat ccgggtattc tggtactca gggtattaaa     420 ggcgataaag gtagccaggg tgaaagcggt attcagggtc gtaagggtga aaaaggccgt    480
cagggtaatc aggcctgca gggcaccgaa ggtctgcgtg gcgaacaggg cgaaaaaggt     540
gagaagggtg acccaggcat tcgt                                          564
```

<210> SEQ ID NO 2
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Asp Thr Gly Phe Pro Gly Met Pro Gly Arg Ser Gly Asp Pro Gly Arg
1               5                   10                  15
Ser Gly Lys Asp Gly Leu Pro Gly Ser Pro Gly Phe Lys Gly Glu Val
            20                  25                  30
Gly Gln Pro Gly Ser Pro Gly Leu Glu Gly His Arg Gly Glu Pro Gly
        35                  40                  45
Ile Pro Gly Ile Pro Gly Asn Gln Gly Ala Lys Gly Gln Lys Gly Glu
    50                  55                  60
Ile Gly Pro Pro Gly Leu Pro Gly Ala Lys Gly Ser Pro Gly Glu Thr
65                  70                  75                  80
Gly Leu Met Gly Pro Glu Gly Ser Phe Gly Leu Pro Gly Ala Pro Gly
                85                  90                  95
Pro Lys Gly Asp Lys Gly Glu Pro Gly Leu Gln Gly Lys Pro Gly Ser
            100                 105                 110
Ser Gly Ala Lys Gly Glu Pro Gly Pro Gly Ala Pro Gly Glu Pro
        115                 120                 125
Gly Tyr Pro Gly Ile Pro Gly Thr Gln Gly Ile Lys Gly Asp Lys Gly
    130                 135                 140
Ser Gln Gly Glu Ser Gly Ile Gln Gly Arg Lys Gly Glu Lys Gly Arg
145                 150                 155                 160
Gln Gly Asn Pro Gly Leu Gln Gly Thr Glu Gly Leu Arg Gly Glu Gln
                165                 170                 175
Gly Glu Lys Gly Glu Lys Gly Asp Pro Gly Ile Arg
            180                 185
```

<210> SEQ ID NO 3
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
gatactggtt tccggggat gcctgggcgc tcaggtgatc cggggcgtag tggaaaagac     60
ggtctgccgg ggtccccggg ctttaagggt gaggtgggtc agcccggtag tccaggttta   120
```

```
gaaggtcacc gcggagagcc cgggattcca ggcattcctg caaccaggg tgccaaggga      180 cagaaaggcg aaattggtcc gcccggccta ccgggcgcga aaggttctcc tggtgaaacc      240
ggtctcatgg gtccggaagg tagcttcggc ctgcccggcg cacctggtcc gaagggcgat      300
aagggggagc ctgggctgca agtaaaccg ggtagttctg cgccaaagg tgaacccggc      360 ggtcccggtg cgccagggga accaggttat cctggtattc ctggaaccca aggaattaaa      420
ggtgacaaag gctcacaggg cgaaagtggt atacagggtc gcaagggcga aaaggacgt       480 cagggcaatc caggcctgca gggtactgaa ggcctgcgtg agaacaggg tgagaaaggt      540 gaaaaggag atcctggtat tcgc                                              564
```

<210> SEQ ID NO 4
<211> LENGTH: 188
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Asp Thr Gly Phe Pro Gly Met Pro Gly Arg Ser Gly Asp Pro Gly Arg
1               5                   10                  15

Ser Gly Lys Asp Gly Leu Pro Gly Ser Pro Gly Phe Lys Gly Glu Val
            20                  25                  30

Gly Gln Pro Gly Ser Pro Gly Leu Glu Gly His Arg Gly Glu Pro Gly
        35                  40                  45

Ile Pro Gly Ile Pro Gly Asn Gln Gly Ala Lys Gly Gln Lys Gly Glu
    50                  55                  60

Ile Gly Pro Pro Gly Leu Pro Gly Ala Lys Gly Ser Pro Gly Glu Thr
65                  70                  75                  80

Gly Leu Met Gly Pro Glu Gly Ser Phe Gly Leu Pro Gly Ala Pro Gly
                85                  90                  95

Pro Lys Gly Asp Lys Gly Glu Pro Gly Leu Gln Gly Lys Pro Gly Ser
            100                 105                 110

Ser Gly Ala Lys Gly Glu Pro Gly Pro Gly Ala Pro Gly Glu Pro
        115                 120                 125

Gly Tyr Pro Gly Ile Pro Gly Thr Gln Gly Ile Lys Gly Asp Lys Gly
    130                 135                 140

Ser Gln Gly Glu Ser Gly Ile Gln Gly Arg Lys Gly Glu Lys Gly Arg
145                 150                 155                 160

Gln Gly Asn Pro Gly Leu Gln Gly Thr Glu Gly Leu Arg Gly Glu Gln
                165                 170                 175

Gly Glu Lys Gly Glu Lys Gly Asp Pro Gly Ile Arg
            180                 185
```

<210> SEQ ID NO 5
<211> LENGTH: 633
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
gatactggtt tccgggggat gcctgggcgc tcaggtgatc cggggcgtag tggaaaagac      60
ggtctgccgg ggtccccggg ctttaaggt gaggtgggtc agcccggtag tccaggttta     120
```

```
gaaggtcacc gcggagagcc cgggattcca ggcattcctg caaccaggg tgccaaggga    180 cagaaaggcg aaattggtcc gcccggccta ccgggcgcga aggttctcc tggtgaaacc    240 ggtctcatgg gtccggaagg tagcttcggc ctgcccggcg cacctggtcc gaagggcgat   300 aaggggagc ctgggctgca aggtaaaccg gtagttctg cgccaaagg tgaacccggc      360 ggtcccggtg cgccagggga accaggttat cctggtattc ctggaaccca aggaattaaa   420
ggtgacaaag gctcacaggg cgaaagtggt atacagggtc gcaagggcga aaaggacgt    480 cagggcaatc caggcctgca gggtactgaa ggcctgcgtg agaacaggg tgagaaggt     540 gaaaaggag atcctggtat tcgcggcatt aacggtcaaa agggtgaaag tgggatacaa    600
ggtcttgtcg gtccgcccgg agttagaggc cag                                633
```

<210> SEQ ID NO 6
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Thr Gly Phe Pro Gly Met Pro Gly Arg Ser Gly Asp Pro Gly Arg
1               5                   10                  15

Ser Gly Lys Asp Gly Leu Pro Gly Ser Pro Gly Phe Lys Gly Glu Val
            20                  25                  30

Gly Gln Pro Gly Ser Pro Gly Leu Glu Gly His Arg Gly Glu Pro Gly
        35                  40                  45

Ile Pro Gly Ile Pro Gly Asn Gln Gly Ala Lys Gly Gln Lys Gly Glu
    50                  55                  60

Ile Gly Pro Pro Gly Leu Pro Gly Ala Lys Gly Ser Pro Gly Glu Thr
65                  70                  75                  80

Gly Leu Met Gly Pro Glu Gly Ser Phe Gly Leu Pro Gly Ala Pro Gly
                85                  90                  95

Pro Lys Gly Asp Lys Gly Glu Pro Gly Leu Gln Gly Lys Pro Gly Ser
            100                 105                 110

Ser Gly Ala Lys Gly Glu Pro Gly Gly Pro Gly Ala Pro Gly Glu Pro
        115                 120                 125

Gly Tyr Pro Gly Ile Pro Gly Thr Gln Gly Ile Lys Gly Asp Lys Gly
    130                 135                 140

Ser Gln Gly Glu Ser Gly Ile Gln Gly Arg Lys Gly Glu Lys Gly Arg
145                 150                 155                 160

Gln Gly Asn Pro Gly Leu Gln Gly Thr Glu Gly Leu Arg Gly Glu Gln
                165                 170                 175

Gly Glu Lys Gly Glu Lys Gly Asp Pro Gly Ile Arg Gly Ile Asn Gly
            180                 185                 190

Gln Lys Gly Glu Ser Gly Ile Gln Gly Leu Val Gly Pro Pro Gly Val
        195                 200                 205

Arg Gly Gln
    210
```

<210> SEQ ID NO 7
<211> LENGTH: 596
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 7

```
gtctgcaggg tatgcctggt gaacgtggtg caagcggtat tgccggtgca aaaggtgatc    60
gtggtgatgt tggtgaaaaa ggtccggaag gtgccagcgg taaagatggt agccgtggtc   120
tgaccggtcc gattggtccg cctggtccgg caggtccgaa tggcgaaaaa ggtgaaagcg   180
gtccgagcgg tcctccgggt gcagcaggta ctcgtggtgc accgggtgat cgcggtgaaa   240
atggtccacc gggtcctgcc ggttttgcag gtccgccagg tgcagatggt cagcctggtg   300
ccaaaggcga acaaggcgaa ggtggtcaga aggtgatgc aggcgctccg ggtccgcagg   360
gtccttctgg tgcacctggt cctcagggtc cgaccggtgt ttctggtccg aaaggcgcac   420
gtggtgccca gggtccacct ggtgcgaccg gttttcctgg cgcagcaggt cgtgttggtc   480
ctccaggtcc taatggtaat ccgggtccaa gcgttcctgc aggtagcgca ggcaaagatg   540
gtcctaaagg tgtacgcggt gatgctggtc ctcctggccg tgccggtgat gccggt       596
```

<210> SEQ ID NO 8
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gly Leu Gln Gly Met Pro Gly Glu Arg Gly Ala Ser Gly Ile Ala Gly
1               5                   10                  15

Ala Lys Gly Asp Arg Gly Asp Val Gly Glu Lys Gly Pro Glu Gly Ala
            20                  25                  30

Ser Gly Lys Asp Gly Ser Arg Gly Leu Thr Gly Pro Ile Gly Pro Pro
        35                  40                  45

Gly Pro Ala Gly Pro Asn Gly Glu Lys Gly Glu Ser Gly Pro Ser Gly
    50                  55                  60

Pro Pro Gly Ala Ala Gly Thr Arg Gly Ala Pro Gly Asp Arg Gly Glu
65                  70                  75                  80

Asn Gly Pro Pro Gly Pro Ala Gly Phe Ala Gly Pro Pro Gly Ala Asp
                85                  90                  95

Gly Gln Pro Gly Ala Lys Gly Glu Gln Gly Glu Gly Gly Gln Lys Gly
            100                 105                 110

Asp Ala Gly Ala Pro Gly Pro Gln Gly Pro Ser Gly Ala Pro Gly Pro
        115                 120                 125

Gln Gly Pro Thr Gly Val Ser Gly Pro Lys Gly Ala Arg Gly Ala Gln
    130                 135                 140

Gly Pro Pro Gly Ala Thr Gly Phe Pro Gly Ala Ala Gly Arg Val Gly
145                 150                 155                 160

Pro Pro Gly Pro Asn Gly Asn Pro Gly Pro Ser Gly Pro Ala Gly Ser
                165                 170                 175

Ala Gly Lys Asp Gly Pro Lys Gly Val Arg Gly Asp Ala Gly Pro Pro
            180                 185                 190

Gly Arg Ala Gly Asp Ala Gly
        195
```

<210> SEQ ID NO 9
<211> LENGTH: 57
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 9
atgaaaaaga tttggctggc gctggctggt ttagttttag cgtttagcgc atcggcg      57

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Lys Lys Ile Trp Leu Ala Leu Ala Gly Leu Val Leu Ala Phe Ser
1               5                   10                  15

Ala Ser Ala

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atgaaaaaag gtttcatgct gtttcaccctc ctcgctgcgt tctctggttt cgcgcaggct   60

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Lys Lys Gly Phe Met Leu Phe Thr Leu Leu Ala Ala Phe Ser Gly
1               5                   10                  15

Phe Ala Gln Ala
            20

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgatgatca ccctgcgtaa actgccgctg gctgttgctg ttgctgctgg tgttatgtct   60
gctcaggcta tggct                                                   75

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

-continued

```
Met Met Ile Thr Leu Arg Lys Leu Pro Leu Ala Val Ala Val Ala Ala
1               5                   10                  15

Gly Val Met Ser Ala Gln Ala Met Ala
            20                  25
```

<210> SEQ ID NO 15
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
atgaaaaaaa ccgctatcgc tatcgctgtt gctctggctg gtttcgctac cgttgctcag    60
gct    63

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

```
Met Lys Lys Thr Ala Ile Ala Ile Ala Val Ala Leu Ala Gly Phe Ala
1               5                   10                  15

Thr Val Ala Gln Ala
            20
```

<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17
atgaaagtta aagttctgtc tctgctggtt ccggctctgc tggttgctgg tgctgctaac    60
gct    63

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Met Lys Val Lys Val Leu Ser Leu Leu Val Pro Ala Leu Leu Val Ala
1               5                   10                  15

Gly Ala Ala Asn Ala
            20
```

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 19
atgaaaaaaa acatcctgtc tctgtctatg gttgctctgt ctctgtctct ggctctgggt    60
tctgtttctg ttaccgct                                                  78

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Lys Lys Asn Ile Leu Ser Leu Ser Met Val Ala Leu Ser Leu Ser
1               5                   10                  15

Leu Ala Leu Gly Ser Val Ser Val Thr Ala
            20                  25

<210> SEQ ID NO 21
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgctgaacc cgaaagttgc ttacatggtt tggatgacct gcctgggtct gaccctgccg    60
tctcaggct                                                            69

<210> SEQ ID NO 22
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Leu Asn Pro Lys Val Ala Tyr Met Val Trp Met Thr Cys Leu Gly
1               5                   10                  15

Leu Thr Leu Pro Ser Gln Ala
            20

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atgaaacagg ctctgcgtgt agcgttcggt ttcctgatac tgtgggcttc tgttctgcac    60
gct                                                                  63

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 24

Met Lys Gln Ala Leu Arg Val Ala Phe Gly Phe Leu Ile Leu Trp Ala
1               5                   10                  15

Ser Val Leu His Ala
            20

<210> SEQ ID NO 25
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ggtctgcagg gtatgccggg tgaacgtggt gccagcggta ttgcaggtgc caaaggtgat     60
cgtggtgatg ttggtgaaaa aggtccggaa ggtgcaagcg gtaaagatgg tagccgtggt    120
ctgaccggtc cgattggtcc gccgggtccg gccggtccga atggtgaaaa aggtgaaagc    180
ggtccgagcg gtccgccggg tgcagccggt acccgtggtg caccgggtga tcgtggtgaa    240
aatggtccgc cgggtccggc cggttttgca ggtccgccgg gtgccgatgg tcagccgggt    300
gcaaaaggtg aacagggtga aggtggtcag aaaggtgatg ccggtgcacc gggtccgcag    360
ggtccgagcg gtgccccggg tccgcagggt ccgaccggtg ttagcggtcc gaaaggtgca    420
cgtggtgccc agggtccgcc gggtgcaacc ggttttccgg gtgccgcagg tcgtgttggt    480
ccgccgggtc cgaatggtaa tccgggtccg agcggtccgg caggtagcgc cggtaaagat    540
ggtccgaaag gtgttcgtgg tgatgcaggt ccgccgggtc gtgccggtga tgcaggttaa    600

<210> SEQ ID NO 26
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ggcctgcaag gcatgccagg cgagcgcggc gcgtctggca tcgcgggcgc gaagggcgac     60
cgcggcgacg tgggcgagaa gggccctgag ggcgcgtccg gcaaggacgg ctctcgcggc    120
ctgacaggcc caatcggccc tccaggccct gcgggcccaa acggcgagaa gggcgagtcc    180
ggcccttctg gcccacctgg cgcggcgggc acacgcggcg cgccaggcga ccgcggcgag    240
aacggccctc caggccctgc gggcttcgcg ggcccacctg gcgcggacgg ccaaccaggc    300
gcgaagggcg agcaaggcga gggcggccaa aagggcgacg cgggcgcgcc tggcccacaa    360
ggcccttctg gcgcgccagg ccctcaaggc ccaacaggcg tgtccggccc taagggcgcg    420
cgcggcgcgc aaggcccacc tggcgcgaca ggcttcccag gcgcggcggg ccgcgtgggc    480
cctccaggcc ctaacggcaa cccaggccct tctggcccag cgggctccgc gggcaaggac    540
ggccctaagg gcgtgcgcgg cgacgcgggc ccacctggcc gcgcgggcga cgcgggctga    600

<210> SEQ ID NO 27
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
ggtttgcaag gtatgccagg ggaacggggt gcgtccggga tagccggggc aaaaggtgat      60
cgaggcgatg taggagaaaa aggcccagaa ggggcgtcag gtaaggacgg atctcgcggc     120
ttgacgggac ctatcgggcc tccaggtccc gccggccta atggggaaaa aggcgagagt      180
gggccgtctg gtccgccgg cgccgctggc acacgtggag cgccgggcga tcgtggtgag      240
aacggaccac cgggtcctgc tggttttgcg ggacctccgg gagcagacgg ccagccgggc     300
gctaaaggtg aacagggtga aggtggccaa aaggcgatg caggcgcacc gggtccgcag      360
ggcccttcag gtgcaccggg tccacagggc ccaactggcg tttcagggcc gaaaggcgca     420
agaggtgctc agggtccgcc cggggcaact gggtttcctg gagcggccgg ccgtgttgga     480
cctccgggc cgaacggaaa ccctggaccg tctggaccag ccggttcagc gggtaaggat      540
ggtcctaagg gtgtaagggg tgacgcaggt ccccctggac gtgcagggga tgcggggtag    600
```

<210> SEQ ID NO 28
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28

```
gggttacaag gtatgccggg agaacgtgga gcgtcaggaa ttgctggggc caaaggtgat      60
cgtggtgatg ttggcgagaa agggcccgaa ggcgcatctg gtaaagatgg ctcacgcggg     120
ttaactggac caatcggacc accaggcccc gctgggccta atggtgaaaa gggtgaaagt      180
ggcccttctg gacccccagg agccgccggt acacgtggag cgccaggcga tcgtggcgaa     240
aacggaccgc ccggacctgc aggttttgcg ggacccctg gagcagacgg ccaaccagga     300
gcaaaaggtg agcaaggtga aggtggacaa aagggagatg ccggagcgcc aggcccccaa     360
ggcccatcag gagctccagg acctcaaggt ccaactggtg tatcagggcc taagggtgcg     420
cgcggcgctc aaggaccgcc tggcgcaact ggctttccgg gagctgctgg tcgtgtgggc     480
ccgcctggcc caaacggaaa tccaggccct tcaggcccgg cgggctcagc cggaaaagac     540
ggtccgaagg gagtccgtgg agatgcggga ccgccaggac gcgctggcga tgcaggctaa    600
```

<210> SEQ ID NO 29
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
ggtttacagg gaatgccagg ggaacgcggc gcctcaggga ttgccggtgc taaaggagat      60
cgtggcgacg tgggtgaaaa gggtcccgag ggagcatcag gtaaggatgg ttcccgtggt     120
ttgacgggac ctattggacc tccgggtcct gcaggtccga acggcgaaaa gggggaaagc     180
gggcctagtg gtccacccgg cgccgcaggt accgtggtg cccaggcga ccgcggggag      240
aatggaccgc ctggccctgc cggttttgcg ggtcctccag gagccgatgg gcagcccggt     300
gcaaaaggag agcagggaga gggaggtcaa aagggagatg ccggcgcccc gggccctcag     360
ggaccaagcg gtgcgccagg cccccagggt cctacgggtg ttagcgggcc gaaaggcgca     420
cgcggagcgc agggcccacc tggtgcaaca ggcttcccag gagctgcggg gcgcgtcgga     480
```

-continued cctccgggac ccaatggaaa cccaggtccg tcagggccgg caggctccgc agggaaagat    540
ggtcccaaag gcgtgcgtgg agacgcaggg ccccccggac gcgccggcga tgcgggataa    600

<210> SEQ ID NO 30
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gatactggtt tcccggggat gcctgggcgc tcaggtgatc cggggcgtag tggaaaagac     60
ggtctgccgg ggtccccggg ctttaagggt gaggtgggtc agcccggtag tccaggttta    120
gaaggtcacc gcggagagcc cgggattcca ggcattcctg caaccaggg tgccaaggga    180 cagaaaggcg aaattggtcc gcccggccta ccgggcgcga aaggttctcc tggtgaaacc    240
ggtctcatgg gtccggaagg tagcttcggc ctgcccggcg cacctggtcc gaagggcgat    300 aaggggagc ctgggctgca aggtaaaccg gtagttctg cgccaaagg tgaacccggc    360 ggtcccggtg cgccagggga accaggttat cctggtattc ctggaaccca aggaattaaa    420
ggtgacaaag gctcacaggg cgaaagtggt atacagggtc gcaagggcga aaaaggacgt    480
cagggcaatc caggcctgca gggtactgaa ggcctgcgtg gagaacaggg tgagaaaggt    540 gaaaaggag atcctggtat tcgc    564

<210> SEQ ID NO 31
<211> LENGTH: 957
<212> TYPE: PRT
<213> ORGANISM: Gallus gallus

<400> SEQUENCE: 31

Met Ala Gln Leu Leu Arg Leu Phe Gln Thr Leu Leu Ile Leu Leu Leu
1               5                   10                  15

Arg Asp Tyr Ile Ser Ala Glu Asp Gly Glu Thr Arg Ala Ser Cys Arg
            20                  25                  30

Thr Ala Pro Ala Asp Leu Val Phe Ile Leu Asp Gly Ser Tyr Ser Val
        35                  40                  45

Gly Pro Glu Asn Phe Glu Ile Ile Lys Ser Trp Leu Val Asn Ile Thr
    50                  55                  60

Arg Asn Phe Asp Ile Gly Pro Lys Phe Ile Gln Val Gly Val Val Gln
65                  70                  75                  80

Tyr Ser Asp Tyr Pro Val Leu Glu Ile Pro Leu Gly Thr His Glu Ser
                85                  90                  95

Thr Glu Asn Leu Ile Lys Glu Met Glu Ser Ile His Tyr Leu Gly Gly
            100                 105                 110

Asn Thr Lys Thr Gly Arg Ala Ile Gln Phe Ala Tyr Asp His Leu Phe
        115                 120                 125

Ala Lys Ser Ser Arg Phe Leu Thr Lys Ile Ala Val Val Leu Thr Asp
    130                 135                 140

Gly Lys Ser Gln Asp Glu Val Lys Asp Val Ala Glu Ala Arg Lys
145                 150                 155                 160

Asn Lys Ile Thr Leu Phe Ala Ile Gly Val Gly Ser Glu Ile Glu Glu
                165                 170                 175

Asp Glu Leu Lys Ala Ile Ala Asn Lys Pro Ser Ser Thr Tyr Val Phe
            180                 185                 190

```
Tyr Val Glu Asp Tyr Ile Ala Ile Ser Arg Ile Lys Glu Val Ile Lys
            195                 200                 205

Gln Lys Leu Cys Glu Glu Ser Val Cys Pro Thr Arg Ile Pro Val Ala
        210                 215                 220

Ala Arg Asp Glu Lys Gly Phe Asp Ile Leu Val Gly Leu Gly Val Lys
225                 230                 235                 240

Lys Arg Val Lys Lys Arg Ile Gln Ile Pro Thr Thr Asn Ala Lys Ala
                245                 250                 255

Tyr Glu Val Thr Ser Arg Val Asp Leu Ser Glu Leu Thr Arg Asn Val
            260                 265                 270

Phe Pro Glu Gly Leu Pro Pro Ser Tyr Val Phe Val Ser Thr Gln Arg
        275                 280                 285

Phe Lys Val Lys Lys Thr Trp Asp Leu Trp Arg Val Leu Ser Leu Asp
        290                 295                 300

Lys Arg Pro Gln Ile Ala Val Thr Ile Asn Gly Glu Glu Lys Thr Leu
305                 310                 315                 320

Ser Phe Thr Thr Thr Ser Leu Ile Asn Gly Thr Gln Val Ile Thr Phe
                325                 330                 335

Ala Ala Pro Arg Val Lys Thr Leu Phe Asp Glu Gly Trp His Gln Ile
            340                 345                 350

Arg Leu Leu Val Thr Glu Asp Phe Val Thr Leu Tyr Ile Asp Asp Gln
        355                 360                 365

Glu Ile Glu Thr Lys Pro Leu His Pro Val Leu Gly Ile Tyr Ile Ser
        370                 375                 380

Gly Leu Thr Gln Ile Gly Lys Tyr Ser Gly Lys Glu Thr Val Gln
385                 390                 395                 400

Phe Asp Ile Gln Lys Leu Arg Ile Tyr Cys Asp Pro Glu Gln Asn Asn
                405                 410                 415

Arg Glu Thr Val Cys Glu Ile Pro Gly Phe Asn Gly Glu Cys Met Asn
            420                 425                 430

Gly Pro Ser Asp Val Gly Ser Thr Pro Ala Pro Cys Ile Cys Pro Pro
        435                 440                 445

Gly Lys Gln Gly Pro Pro Gly Pro Lys Gly Asp Pro Gly Gln Pro Gly
        450                 455                 460

Asn His Gly Tyr Pro Gly Gln Pro Gly Pro Asp Gly Lys Pro Gly Tyr
465                 470                 475                 480

Gln Gly Ser Ala Gly Thr Pro Gly Ile Pro Gly Thr Pro Gly Val Gln
                485                 490                 495

Gly Pro Arg Gly Leu Pro Gly Ile Lys Gly Glu Pro Gly Lys Asp Gly
            500                 505                 510

Thr Lys Gly Asp Arg Gly Leu Pro Gly Phe Pro Gly Leu His Gly Met
        515                 520                 525

Pro Ala Pro Lys Gly Glu Arg Gly Pro Lys Gly Asp Gln Gly Val Pro
530                 535                 540

Gly Ile Tyr Gly Lys Lys Gly Ser Lys Gly Glu Lys Gly Asp Thr Gly
545                 550                 555                 560

Phe Pro Gly Met Pro Gly Arg Ser Gly Asp Pro Gly Arg Ser Gly Lys
                565                 570                 575

Asp Gly Leu Pro Gly Ser Pro Gly Phe Lys Gly Glu Val Gly Gln Pro
            580                 585                 590

Gly Ser Pro Gly Leu Glu Gly His Arg Gly Glu Pro Gly Ile Pro Gly
        595                 600                 605
```

```
Ile Pro Gly Asn Gln Gly Ala Lys Gly Gln Lys Gly Glu Ile Gly Pro
    610                 615                 620
Pro Gly Leu Pro Gly Ala Lys Gly Ser Pro Gly Glu Thr Gly Leu Met
625                 630                 635                 640
Gly Pro Glu Gly Ser Phe Gly Leu Pro Gly Ala Pro Gly Pro Lys Gly
                645                 650                 655
Asp Lys Gly Glu Pro Gly Leu Gln Gly Lys Pro Gly Ser Ser Gly Ala
                660                 665                 670
Lys Gly Glu Pro Gly Gly Pro Gly Ala Pro Gly Glu Pro Gly Tyr Pro
    675                 680                 685
Gly Ile Pro Gly Thr Gln Gly Ile Lys Gly Asp Lys Gly Ser Gln Gly
    690                 695                 700
Glu Ser Gly Ile Gln Gly Arg Lys Gly Glu Lys Gly Arg Gln Gly Asn
705                 710                 715                 720
Pro Gly Leu Gln Gly Thr Glu Gly Leu Arg Gly Gln Gly Glu Lys
                725                 730                 735
Gly Glu Lys Gly Asp Pro Gly Ile Arg Gly Ile Asn Gly Gln Lys Gly
                740                 745                 750
Glu Ser Gly Ile Gln Gly Leu Val Gly Pro Pro Gly Val Arg Gly Gln
    755                 760                 765
Pro Gly Asp Arg Gly Pro Pro Gly Pro Pro Gly Ser Asp Gly Lys Pro
    770                 775                 780
Ala Arg Glu Phe Ser Glu Glu Phe Ile Arg Gln Val Cys Ser Asp Val
785                 790                 795                 800
Leu Arg Thr Gln Leu Pro Val Ile Leu Gln Ser Gly Arg Leu Gln Asn
                805                 810                 815
Cys Asn His Cys Gln Ser Gln Ser Ala Ser Pro Gly Leu Pro Gly Pro
                820                 825                 830
Pro Gly Pro Arg Gly Pro Glu Gly Pro Arg Gly Phe Pro Gly Leu Pro
    835                 840                 845
Gly Asn Asp Gly Val Pro Gly Leu Thr Gly Ile Pro Gly Arg Pro Gly
    850                 855                 860
Ala Arg Gly Thr Arg Gly Leu Pro Gly Lys Asn Gly Ala Lys Gly Asn
865                 870                 875                 880
Gln Gly Ile Gly Val Pro Gly Ile Gln Gly Pro Pro Gly Pro Pro Gly
                885                 890                 895
Pro Glu Gly Pro Pro Gly Met Ser Lys Glu Gly Arg Pro Gly Glu Arg
                900                 905                 910
Gly Gln Pro Gly Lys Asp Gly Asp Arg Gly Ser Pro Gly Met Pro Gly
    915                 920                 925
Pro Val Gly Pro Pro Gly Ile Cys Asp Pro Ser Leu Cys Phe Ser Val
    930                 935                 940
Ile Val Gly Arg Asp Pro Phe Arg Lys Gly Pro Asn Tyr
945                 950                 955

<210> SEQ ID NO 32
<211> LENGTH: 1420
<212> TYPE: PRT
<213> ORGANISM: Acipenser schrenckii

<400> SEQUENCE: 32

Met Phe Ser Phe Val Asp Ser Arg Thr Val Leu Leu Leu Ala Ala Ile
1               5                   10                  15
Gln Leu Cys Leu Leu Ala Val Val Lys Cys Gln Asp Val Glu Val Gln
                20                  25                  30
```

-continued

Gln Pro Gly Arg Lys Gly Gln Lys Gly Glu Pro Gly Asp Ile Thr Asp
          35                  40                  45

Val Val Gly Pro Arg Gly Pro Gly Gly Pro Met Gly Pro Pro Gly Glu
    50                  55                  60

Gln Gly Pro Arg Gly Glu Arg Gly Asp Lys Gly Asp Lys Gly Gly Pro
65                  70                  75                  80

Gly Pro Arg Gly Arg Asp Gly Glu Pro Gly Thr Pro Gly Asn Pro Gly
              85                  90                  95

Pro Pro Gly Pro Pro Gly Pro Asn Gly Pro Pro Gly Leu Gly Gly Asn
              100                 105                 110

Phe Ala Ala Gln Met Ala Gly Gly Phe Asp Glu Lys Ala Gly Gly Ala
              115                 120                 125

Gln Met Gly Val Met Gln Gly Pro Met Gly Pro Met Gly Pro Arg Gly
        130                 135                 140

Pro Pro Gly Pro Thr Gly Ala Pro Gly Pro Gln Gly Phe Gln Gly Asn
145                 150                 155                 160

Pro Gly Glu Pro Gly Glu Pro Gly Ala Ala Gly Pro Leu Gly Pro Arg
                165                 170                 175

Gly Pro Pro Gly Pro Ser Gly Lys Pro Gly Glu Asp Gly Glu Ala Gly
              180                 185                 190

Lys Pro Gly Lys Ser Gly Glu Arg Gly Ser Pro Gly Pro Gln Gly Ala
        195                 200                 205

Arg Gly Phe Pro Gly Thr Pro Gly Leu Pro Gly Ile Lys Gly His Arg
    210                 215                 220

Gly Tyr Pro Gly Leu Asp Gly Ala Lys Gly Glu Ala Gly Ala Ala Gly
225                 230                 235                 240

Ser Lys Gly Glu Ala Gly Ser Ser Gly Glu Asn Gly Ala Pro Gly Pro
                245                 250                 255

Met Gly Pro Arg Gly Leu Pro Gly Glu Arg Gly Arg Asn Gly Pro Ser
              260                 265                 270

Gly Ala Ala Gly Ala Arg Gly Asn Asp Gly Leu Pro Gly Pro Ala Gly
        275                 280                 285

Pro Pro Gly Pro Val Gly Pro Ala Gly Ala Pro Gly Phe Pro Gly Ser
290                 295                 300

Pro Gly Ser Lys Gly Glu Ala Gly Pro Thr Gly Ala Arg Gly Pro Glu
305                 310                 315                 320

Gly Ala Gln Gly Pro Arg Gly Glu Ser Gly Thr Pro Gly Ser Pro Gly
                325                 330                 335

Pro Ser Gly Ala Ser Gly Asn Pro Gly Thr Asp Gly Ile Pro Gly Ala
              340                 345                 350

Lys Gly Ser Ala Gly Ala Pro Gly Ile Ala Gly Ala Pro Gly Phe Pro
        355                 360                 365

Gly Pro Arg Gly Pro Pro Gly Pro Gln Gly Ala Thr Gly Pro Leu Gly
    370                 375                 380

Pro Lys Gly Gln Gln Gly Asp Pro Gly Ile Pro Gly Phe Lys Gly Glu
385                 390                 395                 400

His Gly Pro Lys Gly Glu His Gly Pro Ala Gly Pro Gln Gly Ala Pro
                405                 410                 415

Gly Pro Ala Gly Glu Glu Gly Lys Arg Gly Ala Arg Gly Glu Pro Gly
              420                 425                 430

Ala Ala Gly Pro Leu Gly Pro Pro Gly Glu Arg Gly Ala Pro Gly Asn
        435                 440                 445

Arg Gly Phe Pro Gly Gln Asp Gly Leu Ala Gly Pro Lys Gly Ala Pro
450                 455                 460

Gly Glu Arg Gly Gln Pro Gly Val Gly Pro Lys Gly Ala Asn Gly
465                 470                 475                 480

Asp Pro Gly Arg Pro Gly Glu Pro Gly Leu Pro Gly Ala Arg Gly Leu
            485                 490                 495

Thr Gly Arg Pro Gly Asp Ala Gly Pro Gln Gly Lys Gly Gly Pro Ser
        500                 505                 510

Gly Ala Ala Gly Glu Asp Gly Arg Pro Gly Pro Pro Gly Pro Gln Gly
            515                 520                 525

Ala Arg Gly Gln Pro Gly Val Met Gly Phe Pro Gly Pro Lys Gly Ala
530                 535                 540

Asn Gly Glu Pro Gly Lys Ala Gly Glu Lys Gly Leu Val Gly Pro Pro
545                 550                 555                 560

Gly Leu Arg Gly Leu Ser Gly Lys Asp Gly Glu Thr Gly Ala Ala Gly
            565                 570                 575

Pro Pro Gly Pro Ser Gly Pro Ala Gly Glu Arg Gly Glu Gln Gly Pro
        580                 585                 590

Pro Gly Pro Ser Gly Phe Gln Gly Leu Pro Gly Pro Pro Gly Pro Pro
    595                 600                 605

Gly Glu Gly Gly Lys Pro Gly Asp Gln Gly Val Pro Gly Glu Ala Gly
610                 615                 620

Ala Ala Gly Arg Ala Gly Pro Arg Gly Glu Arg Gly Phe Pro Gly Glu
625                 630                 635                 640

Arg Gly Ser Pro Gly Ala Gln Gly Leu Gln Gly Pro Arg Gly Leu Pro
            645                 650                 655

Gly Thr Pro Gly Thr Asp Gly Pro Lys Gly Ala Thr Gly Pro Ser Gly
        660                 665                 670

Ala Leu Gly Ala Gln Gly Pro Pro Gly Leu Gln Gly Met Pro Gly Glu
            675                 680                 685

Arg Gly Ala Ser Gly Ile Ala Gly Ala Lys Gly Asp Arg Gly Asp Val
690                 695                 700

Gly Glu Lys Gly Pro Glu Gly Ala Ser Gly Lys Asp Gly Ser Arg Gly
705                 710                 715                 720

Leu Thr Gly Pro Ile Gly Pro Pro Gly Pro Ala Gly Pro Asn Gly Glu
            725                 730                 735

Lys Gly Glu Ser Gly Pro Ser Gly Pro Pro Gly Ala Ala Gly Thr Arg
        740                 745                 750

Gly Ala Pro Gly Asp Arg Gly Glu Asn Gly Pro Pro Gly Pro Ala Gly
            755                 760                 765

Phe Ala Gly Pro Pro Gly Ala Asp Gly Gln Pro Gly Ala Lys Gly Glu
770                 775                 780

Gln Gly Glu Gly Gly Gln Lys Gly Asp Ala Gly Ala Pro Gly Pro Gln
785                 790                 795                 800

Gly Pro Ser Gly Ala Pro Gly Pro Gln Gly Pro Thr Gly Val Ser Gly
            805                 810                 815

Pro Lys Gly Ala Arg Gly Ala Gln Gly Pro Pro Gly Ala Thr Gly Phe
        820                 825                 830

Pro Gly Ala Ala Gly Arg Val Gly Pro Pro Gly Pro Asn Gly Asn Pro
            835                 840                 845

Gly Pro Ser Gly Pro Ala Gly Ser Ala Gly Lys Asp Gly Pro Lys Gly
        850                 855                 860

Val Arg Gly Asp Ala Gly Pro Pro Gly Arg Ala Gly Asp Ala Gly Leu

-continued

```
              865                 870                 875                 880
        Gln Gly Ala Ala Gly Pro Pro Gly Glu Lys Gly Glu Pro Gly Glu Asp
                        885                 890                 895
        Gly Pro Pro Gly Pro Asp Gly Pro Ser Gly Pro Gln Gly Leu Gly Gly
                    900                 905                 910
        Asn Arg Gly Ile Val Gly Leu Pro Gly Gln Arg Gly Glu Arg Gly Phe
                    915                 920                 925
        Pro Gly Leu Pro Gly Pro Ser Gly Glu Pro Gly Lys Gln Gly Ala Pro
        930                 935                 940
        Gly Gly Ala Gly Asp Arg Gly Pro Gly Pro Val Gly Pro Pro Gly
        945                 950                 955                 960
        Leu Ser Gly Pro Ser Gly Glu Pro Gly Arg Glu Gly Asn Pro Gly Ser
                        965                 970                 975
        Asp Gly Pro Pro Gly Arg Asp Gly Ser Ala Gly Ile Lys Gly Asp Arg
                    980                 985                 990
        Gly Gln Thr Gly Pro Ala Gly Ala  Pro Gly Ala Pro Gly  Ala Pro Gly
                    995                 1000                1005
        Ser Pro  Gly Pro Val Gly Pro  Thr Gly Lys Gln Gly  Asp Arg Gly
        1010                1015                1020
        Glu Ser  Gly Ala Gln Gly Pro  Ala Gly Pro Ser Gly  Pro Ala Gly
        1025                1030                1035
        Ala Arg  Gly Met Ala Gly Pro  Gln Gly Pro Arg Gly  Asp Lys Gly
        1040                1045                1050
        Glu Ala  Gly Glu Thr Gly Glu  Arg Gly Gln Lys Gly  His Arg Gly
        1055                1060                1065
        Phe Thr  Gly Leu Gln Gly Leu  Pro Gly Pro Pro Gly  Thr Ala Gly
        1070                1075                1080
        Asp Gln  Gly Ala Ala Gly Pro  Ala Gly Pro Thr Gly  Ala Arg Gly
        1085                1090                1095
        Pro Pro  Gly Pro Val Gly Pro  His Gly Lys Asp Gly  Ser Asn Gly
        1100                1105                1110
        Gln Pro  Gly Pro Ile Gly Pro  Pro Gly Pro Arg Gly  Arg Ser Gly
        1115                1120                1125
        Glu Val  Gly Pro Ala Gly Pro  Pro Gly Asn Ala Gly  Pro Pro Gly
        1130                1135                1140
        Pro Pro  Gly Pro Pro Gly Pro  Gly Ile Asp Met Ser  Ala Phe Ala
        1145                1150                1155
        Gly Leu  Ala Ala Pro Glu Lys  Ala Pro Asp Pro Met  Arg Tyr Met
        1160                1165                1170
        Arg Ala  Asp Glu Ala Ser Ser  Ser Leu Arg Gln His  Asp Ala Glu
        1175                1180                1185
        Val Asp  Ala Thr Leu Lys Ser  Ile Asn Asn Gln Ile  Glu Asn Ile
        1190                1195                1200
        Arg Ser  Pro Glu Gly Ser Lys  Lys Asn Pro Ala Arg  Thr Cys Arg
        1205                1210                1215
        Asp Leu  Lys Leu Cys His Pro  Asp Trp Lys Ser Gly  Asp Tyr Trp
        1220                1225                1230
        Ile Asp  Pro Asn Gln Gly Cys  Ala Val Asp Ala Ile  Lys Val Phe
        1235                1240                1245
        Cys Asn  Met Glu Ser Gly Glu  Thr Cys Val Tyr Pro  Asn Pro Ala
        1250                1255                1260
        Ser Ile  Pro Arg Lys Asn Trp  Trp Thr Ser Lys Ser  Ala Asp Cys
        1265                1270                1275
```

```
Lys His Val Trp Phe Gly Glu Thr Met Asn Gly Gly Phe His Phe
    1280            1285            1290

Ser Tyr Gly Asp Asp Ser Leu Ala Pro Asn Thr Ala Ser Ile Gln
    1295            1300            1305

Met Thr Phe Leu Arg Leu Leu Ser Thr Glu Ala Ser Gln Asn Leu
    1310            1315            1320

Thr Tyr His Cys Lys Asn Ser Ile Ala Tyr Met Asp Gln Ser Ala
    1325            1330            1335

Gly Asn Leu Lys Lys Ala Val Leu Leu Gln Gly Ser Asn Asp Val
    1340            1345            1350

Glu Ile Arg Ala Glu Gly Asn Ser Arg Phe Thr Tyr Asn Val Leu
    1355            1360            1365

Glu Asp Gly Cys Thr Lys His Thr Asp Arg Trp Gly Lys Thr Val
    1370            1375            1380

Ile Glu Tyr Lys Ser Gln Lys Thr Ser Arg Leu Pro Ile Val Asp
    1385            1390            1395

Ile Ala Pro Leu Asp Ile Gly Gly Ser Asp Gln Glu Phe Gly Val
    1400            1405            1410

Asp Ile Gly Pro Val Cys Tyr
    1415            1420

<210> SEQ ID NO 33
<211> LENGTH: 213
<212> TYPE: PRT
<213> ORGANISM: Gallus gallus

<400> SEQUENCE: 33

Asp Thr Gly Phe Pro Gly Met Pro Gly Arg Ser Gly Asp Pro Gly Arg
1               5                   10                  15

Ser Gly Lys Asp Gly Leu Pro Gly Ser Pro Gly Phe Lys Gly Glu Val
                20                  25                  30

Gly Gln Pro Gly Ser Pro Gly Leu Glu Gly His Arg Gly Glu Pro Gly
            35                  40                  45

Ile Pro Gly Ile Pro Gly Asn Gln Gly Ala Lys Gly Gln Lys Gly Glu
        50                  55                  60

Ile Gly Pro Pro Gly Leu Pro Gly Ala Lys Gly Ser Pro Gly Glu Thr
65                  70                  75                  80

Gly Leu Met Gly Pro Glu Gly Ser Phe Gly Leu Pro Gly Ala Pro Gly
                85                  90                  95

Pro Lys Gly Asp Lys Gly Glu Pro Gly Leu Gln Gly Lys Pro Gly Ser
                100                 105                 110

Ser Gly Ala Lys Gly Glu Pro Gly Pro Gly Ala Pro Gly Glu Pro
            115                 120                 125

Gly Tyr Pro Gly Ile Pro Gly Thr Gln Gly Ile Lys Gly Asp Lys Gly
        130                 135                 140

Ser Gln Gly Glu Ser Gly Ile Gln Gly Arg Lys Gly Glu Lys Gly Arg
145                 150                 155                 160

Gln Gly Asn Pro Gly Leu Gln Gly Thr Glu Gly Leu Arg Gly Glu Gln
                165                 170                 175

Gly Glu Lys Gly Glu Lys Gly Asp Pro Gly Ile Arg Gly Ile Asn Gly
                180                 185                 190

Gln Lys Gly Glu Ser Gly Ile Gln Gly Leu Val Gly Pro Pro Gly Val
            195                 200                 205

Arg Gly Gln Pro Gly
```

<210> SEQ ID NO 34
<211> LENGTH: 199
<212> TYPE: PRT
<213> ORGANISM: Acipenser schrenckii

<400> SEQUENCE: 34

Gly Leu Gln Gly Met Pro Gly Glu Arg Gly Ala Ser Gly Ile Ala Gly
1               5                   10                  15

Ala Lys Gly Asp Arg Gly Asp Val Gly Glu Lys Gly Pro Glu Gly Ala
            20                  25                  30

Ser Gly Lys Asp Gly Ser Arg Gly Leu Thr Gly Pro Ile Gly Pro Pro
        35                  40                  45

Gly Pro Ala Gly Pro Asn Gly Glu Lys Gly Glu Ser Gly Pro Ser Gly
    50                  55                  60

Pro Pro Gly Ala Ala Gly Thr Arg Gly Ala Pro Gly Asp Arg Gly Glu
65                  70                  75                  80

Asn Gly Pro Pro Gly Pro Ala Gly Phe Ala Gly Pro Pro Gly Ala Asp
                85                  90                  95

Gly Gln Pro Gly Ala Lys Gly Glu Gln Gly Glu Gly Gln Lys Gly
            100                 105                 110

Asp Ala Gly Ala Pro Gly Pro Gln Gly Pro Ser Gly Ala Pro Gly Pro
        115                 120                 125

Gln Gly Pro Thr Gly Val Ser Gly Pro Lys Gly Ala Arg Gly Ala Gln
    130                 135                 140

Gly Pro Pro Gly Ala Thr Gly Phe Pro Gly Ala Ala Gly Arg Val Gly
145                 150                 155                 160

Pro Pro Gly Pro Asn Gly Asn Pro Gly Pro Ser Gly Pro Ala Gly Ser
                165                 170                 175

Ala Gly Lys Asp Gly Pro Lys Gly Val Arg Gly Asp Ala Gly Pro Pro
            180                 185                 190

Gly Arg Ala Gly Asp Ala Gly
        195

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Thr Gly Phe Pro Gly Met Pro Gly Arg
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Thr Gly Phe Pro Gly Met Pro Gly Arg Ser Gly Asp
1               5                   10

<210> SEQ ID NO 37

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Thr Gly Phe Pro Gly Met Pro Gly Arg Ser Gly Asp Pro Gly Arg
1               5                   10                  15

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Thr Gly Phe Pro Gly Met Pro Gly Arg Ser Gly Asp Pro Gly Arg
1               5                   10                  15

Ser Gly Lys

<210> SEQ ID NO 39
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Thr Gly Phe Pro Gly Met Pro Gly Arg Ser Gly Asp Pro Gly Arg
1               5                   10                  15

Ser Gly Lys Asp Gly Leu Pro Gly Ser Pro Gly Phe Lys
            20                  25

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Gly Phe Pro Gly Met Pro Gly Arg
1               5

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Phe Pro Gly Met Pro Gly Arg Ser Gly Asp Pro Gly Arg Ser Gly
1               5                   10                  15

Lys

<210> SEQ ID NO 42
<211> LENGTH: 15
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 42

Pro Gly Met Pro Gly Arg Ser Gly Asp Pro Gly Arg Ser Gly Lys
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Gly Arg Ser Gly Asp Pro Gly Arg Ser Gly Lys
1               5                   10

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Gly Asp Pro Gly Arg
1               5

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Gly Asp Pro Gly Arg Ser Gly Lys Asp Gly Leu Pro Gly Ser Pro
1               5                   10                  15

Gly Phe Lys

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Gly Leu Pro Gly Ser Pro Gly Phe Lys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Asp Gly Leu Pro Gly Ser Pro Gly Phe Lys Gly Glu
1               5                   10
```

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Asp Gly Leu Pro Gly Ser Pro Gly Phe Lys Gly Glu Val Gly Gln Pro
1               5                   10                  15

Gly Ser Pro Gly Leu Glu Gly His Arg
            20                  25
```

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Asp Gly Leu Pro Gly Ser Pro Gly Phe Lys Gly Glu Val Gly Gln Pro
1               5                   10                  15

Gly Ser Pro Gly Leu Glu Gly His Arg Gly Glu Pro Gly Ile Pro Gly
            20                  25                  30

Ile Pro Gly Asn Gln Gly Ala Lys
            35                  40
```

<210> SEQ ID NO 50
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Gly Leu Pro Gly Ser Pro Gly Phe Lys Gly Glu Val Gly Gln Pro
1               5                   10                  15

Gly Ser Pro Gly Leu Glu Gly His Arg Gly Glu Pro Gly Ile Pro Gly
            20                  25                  30

Ile Pro Gly Asn Gln Gly Ala Lys Gly Gln Lys
            35                  40
```

<210> SEQ ID NO 51
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gly Leu Pro Gly Ser Pro Gly Phe Lys Gly Glu Val Gly Gln Pro Gly
1               5                   10                  15

Ser Pro Gly Leu Glu Gly His Arg Gly Glu Pro Gly Ile Pro Gly Ile
            20                  25                  30

Pro Gly Asn Gln Gly Ala Lys
            35
```

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Ser Pro Gly Phe Lys Gly Glu Val Gly Gln Pro Gly Ser Pro
1               5                   10                  15

Gly Leu Glu Gly His Arg
            20

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Glu Val Gly Gln Pro Gly Ser Pro Gly Leu Glu Gly His Arg
1               5                   10                  15

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Glu Val Gly Gln Pro Gly Ser Pro Gly Leu Glu Gly His Arg Gly
1               5                   10                  15

Glu Pro Gly Ile Pro Gly Ile Pro Gly Asn Gln Gly Ala Lys
            20                  25                  30

<210> SEQ ID NO 55
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Glu Val Gly Gln Pro Gly Ser Pro Gly Leu Glu Gly His Arg Gly
1               5                   10                  15

Glu Pro Gly Ile Pro Gly Ile Pro Gly Asn Gln Gly Ala Lys Gly Gln
            20                  25                  30

Lys

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Arg Gly Glu Pro Gly Ile Pro Gly Ile Pro Gly Asn Gln Gly Ala Lys
 1               5                  10                  15
```

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Gly Glu Pro Gly Ile Pro Gly Ile Pro Gly Asn Gln Gly Ala Lys
 1               5                  10                  15
```

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Gly Glu Pro Gly Ile Pro Gly Ile Pro Gly Asn Gln Gly Ala Lys Gly
 1               5                  10                  15

Gln Lys
```

<210> SEQ ID NO 59
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gly Glu Pro Gly Ile Pro Gly Ile Pro Gly Asn Gln Gly Ala Lys Gly
 1               5                  10                  15

Gln Lys Gly Glu Ile Gly Pro Pro Gly Leu Pro Gly Ala Lys
            20                  25                  30
```

<210> SEQ ID NO 60
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Gly Glu Pro Gly Ile Pro Gly Ile Pro Gly Asn Gln Gly Ala Lys Gly
 1               5                  10                  15

Gln Lys Gly Glu Ile Gly Pro Pro Gly Leu Pro Gly Ala Lys Gly Ser
            20                  25                  30

Pro Gly Glu Thr Gly Leu Met Gly Pro Glu Gly Ser Phe Gly Leu Pro
        35                  40                  45

Gly Ala Pro Gly Pro Lys
    50
```

<210> SEQ ID NO 61
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 61

Pro Gly Asn Gln Gly Ala Lys Gly Gln Lys
1               5                   10

<210> SEQ ID NO 62
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Gly Asn Gln Gly Ala Lys Gly Gln Lys Gly Glu Ile Gly Pro Pro
1               5                   10                  15

Gly Leu Pro Gly Ala Lys
            20

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gln Lys Gly Glu Ile Gly Pro Pro Gly Leu Pro Gly Ala Lys
1               5                   10                  15

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Lys Gly Glu Ile Gly Pro Pro Gly Leu Pro Gly Ala Lys
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Glu Ile Gly Pro Pro Gly Leu Pro Gly Ala Lys
1               5                   10

<210> SEQ ID NO 66
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gly Glu Ile Gly Pro Pro Gly Leu Pro Gly Ala Lys Gly Ser Pro Gly

```
                1               5                  10                  15
Glu Thr Gly Leu Met Gly Pro Glu Gly Ser Phe Gly Leu Pro Gly Ala
                    20                  25                  30

Pro Gly Pro Lys Gly Asp Lys Gly Glu Pro Gly Leu Gln Gly Lys Pro
            35                  40                  45

Gly Ser Ser Gly Ala Lys
        50

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Gly Pro Pro Gly Leu Pro Gly Ala Lys
1               5                   10

<210> SEQ ID NO 68
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Pro Gly Glu Thr Gly Leu Met Gly Pro Glu Gly Ser Phe Gly
1               5                   10                  15

Leu Pro Gly Ala Pro Gly Pro Lys
            20

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Ser Pro Gly Glu Thr Gly Leu Met Gly Pro Glu Gly Ser Phe Gly
1               5                   10                  15

Leu Pro Gly Ala Pro Gly Pro Lys
            20

<210> SEQ ID NO 70
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Pro Gly Glu Thr Gly Leu Met Gly Pro Glu Gly Ser Phe Gly
1               5                   10                  15

Leu Pro Gly Ala Pro Gly Pro Lys Gly Asp
            20                  25

<210> SEQ ID NO 71
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Pro Gly Glu Thr Gly Leu Met Gly Pro Glu Gly Ser Phe Gly
1               5                   10                  15

Leu Pro Gly Ala Pro Gly Pro Lys Gly Asp Lys
            20                  25

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Gly Leu Met Gly Pro Glu Gly Ser Phe Gly Leu Pro Gly Ala Pro
1               5                   10                  15

Gly Pro Lys

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Met Gly Pro Glu Gly Ser Phe Gly Leu Pro Gly Ala Pro Gly
1               5                   10                  15

Pro Lys

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Phe Gly Leu Pro Gly Ala Pro Gly Pro Lys
1               5                   10

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Asp Lys Gly Glu Pro Gly Leu Gln Gly Lys Pro Gly Ser Ser Gly
1               5                   10                  15

Ala Lys

<210> SEQ ID NO 76
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys Gly Glu Pro Gly Leu Gln Gly Lys Pro Gly Ser Ser Gly Ala Lys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Glu Pro Gly Leu Gln Gly Lys Pro Gly Ser Ser Gly Ala Lys
1               5                   10                  15

<210> SEQ ID NO 78
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gly Glu Pro Gly Leu Gln Gly Lys Pro Gly Ser Ser Gly Ala Lys Gly
1               5                   10                  15

Glu Pro Gly Gly Pro Gly Ala Pro Gly Glu Pro Gly Tyr Pro Gly Ile
            20                  25                  30

Pro Gly Thr Gln Gly Ile Lys Gly Asp Lys
        35                  40

<210> SEQ ID NO 79
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Glu Pro Gly Gly Pro Gly Ala Pro Gly Glu Pro Gly Tyr Pro Gly
1               5                   10                  15

Ile Pro Gly Thr Gln Gly Ile Lys
            20

<210> SEQ ID NO 80
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Glu Pro Gly Gly Pro Gly Ala Pro Gly Glu Pro Gly Tyr Pro Gly
1               5                   10                  15

Ile Pro Gly Thr Gln Gly Ile Lys Gly Asp Lys
            20                  25
```

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 81

Pro Gly Glu Pro Gly Tyr Pro Gly Ile Pro Gly Thr Gln Gly Ile Lys
1               5                   10                  15

Gly Asp Lys Gly Ser Gln Gly Glu Ser Gly Ile Gln Gly Arg
            20                  25                  30

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 82

Pro Gly Tyr Pro Gly Ile Pro Gly Thr Gln Gly Ile Lys Gly Asp Lys
1               5                   10                  15

Gly Ser Gln Gly Glu Ser Gly Ile Gln Gly Arg
            20                  25

<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 83

Pro Gly Ile Pro Gly Thr Gln Gly Ile Lys Gly Asp Lys Gly Ser Gln
1               5                   10                  15

Gly Glu Ser Gly Ile Gln Gly Arg
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 84

Pro Gly Thr Gln Gly Ile Lys Gly Asp Lys Gly Ser Gln Gly Glu Ser
1               5                   10                  15

Gly Ile Gln Gly Arg
            20

<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 85

```
Pro Gly Thr Gln Gly Ile Lys Gly Asp Lys Gly Ser Gln Gly Glu Ser
1               5                   10                  15

Gly Ile Gln Gly Arg Lys
            20
```

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

```
Gly Asp Lys Gly Ser Gln Gly Glu Ser Gly Ile Gln Gly Arg
1               5                   10
```

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

```
Gly Asp Lys Gly Ser Gln Gly Glu Ser Gly Ile Gln Gly Arg Lys
1               5                   10                  15
```

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

```
Gly Asp Lys Gly Ser Gln Gly Glu Ser Gly Ile Gln Gly Arg Lys Gly
1               5                   10                  15

Glu Lys
```

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

```
Gly Asp Lys Gly Ser Gln Gly Glu Ser Gly Ile Gln Gly Arg Lys Gly
1               5                   10                  15

Glu Lys Gly Arg
            20
```

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Lys Gly Ser Gln Gly Glu Ser Gly Ile Gln Gly Arg
```

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Gln Gly Glu Ser Gly Ile Gln Gly Arg
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gln Gly Glu Ser Gly Ile Gln Gly Arg Lys
1               5                   10

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Gln Gly Glu Ser Gly Ile Gln Gly Arg Lys Gly Glu Lys
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Gln Gly Glu Ser Gly Ile Gln Gly Arg Lys Gly Glu Lys Gly
1               5                   10                  15

Arg

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Gly Glu Lys Gly Arg Gln Gly Asn Pro Gly Leu Gln Gly Thr Glu
1               5                   10                  15

Gly Leu Arg

<210> SEQ ID NO 96
<211> LENGTH: 25

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Gly Glu Lys Gly Arg Gln Gly Asn Pro Gly Leu Gln Gly Thr Glu
1               5                   10                  15

Gly Leu Arg Gly Glu Gln Gly Glu Lys
            20                  25

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Glu Lys Gly Arg Gln Gly Asn Pro Gly Leu Gln Gly Thr Glu Gly
1               5                   10                  15

Leu Arg

<210> SEQ ID NO 98
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Glu Lys Gly Arg Gln Gly Asn Pro Gly Leu Gln Gly Thr Glu Gly
1               5                   10                  15

Leu Arg Gly Glu Gln Gly Glu Lys Gly Glu Lys
            20                  25

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Arg Gln Gly Asn Pro Gly Leu Gln Gly Thr Glu Gly Leu
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Arg Gln Gly Asn Pro Gly Leu Gln Gly Thr Glu Gly Leu Arg
1               5                   10                  15

<210> SEQ ID NO 101
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 101

Gly Arg Gln Gly Asn Pro Gly Leu Gln Gly Thr Glu Gly Leu Arg Gly
1               5                   10                  15

Glu Gln Gly Glu Lys
            20

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Arg Gln Gly Asn Pro Gly Leu Gln Gly Thr Glu Gly Leu Arg Gly
1               5                   10                  15

Glu Gln Gly Glu Lys Gly Glu Lys
            20

<210> SEQ ID NO 103
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Arg Gln Gly Asn Pro Gly Leu Gln Gly Thr Glu Gly Leu Arg Gly
1               5                   10                  15

Glu Gln Gly Glu Lys Gly Glu Lys Gly Asp
            20                  25

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gly Asn Pro Gly Leu Gln Gly Thr Glu Gly Leu Arg
1               5                   10

<210> SEQ ID NO 105
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gly Asn Pro Gly Leu Gln Gly Thr Glu Gly Leu Arg Gly Glu Gln
1               5                   10                  15

Gly Glu Lys

<210> SEQ ID NO 106
```

<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gln Gly Asn Pro Gly Leu Gln Gly Thr Glu Gly Leu Arg Gly Glu Gln
1               5                   10                  15

Gly Glu Lys Gly Glu Lys
            20

<210> SEQ ID NO 107
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Gly Asn Pro Gly Leu Gln Gly Thr Glu Gly Leu Arg Gly Glu Gln
1               5                   10                  15

Gly Glu Lys Gly Glu Lys Gly Asp
            20

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Gly Glu Gln Gly Glu Lys Gly Glu Lys Gly Asp Pro Gly Ile Arg
1               5                   10                  15

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Glu Gln Gly Glu Lys
1               5

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Glu Gln Gly Glu Lys Gly Glu Lys Gly Asp Pro Gly Ile Arg
1               5                   10                  15

<210> SEQ ID NO 111
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 111

Gly Glu Lys Gly Asp Pro Gly Ile Arg
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Asp Pro Gly Ile Arg
1               5
```